US012692473B2

(12) United States Patent (10) Patent No.: US 12,692,473 B2
Miyagishima et al. (45) Date of Patent: Jul. 28, 2026

(54) MICROALGAE AND USE FOR SAME

(71) Applicant: JAPAN SCIENCE AND TECHNOLOGY AGENCY, Saitama (JP)

(72) Inventors: Shin-Ya Miyagishima, Shizuoka (JP); Shunsuke Hirooka, Shizuoka (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 0 days.

(21) Appl. No.: 19/182,315

(22) Filed: Apr. 17, 2025

(65) Prior Publication Data

US 2025/0243449 A1 Jul. 31, 2025

Related U.S. Application Data

(62) Division of application No. 16/766,946, filed as application No. PCT/JP2018/043696 on Nov. 28, 2018, now Pat. No. 12,286,616.

(30) Foreign Application Priority Data

Nov. 28, 2017 (JP) ................................. 2017-228394
Nov. 28, 2017 (JP) ................................. 2017-228396
May 28, 2018 (JP) ................................. 2018-101753
Sep. 21, 2018 (JP) ................................. 2018-177416

(51) Int. Cl.
| | |
|---|---|
| *C12N 1/12* | (2026.01) |
| *A23K 10/16* | (2016.01) |
| *A23L 17/60* | (2016.01) |
| *A23L 33/105* | (2016.01) |
| *A61K 8/9717* | (2017.01) |
| *C12N 1/06* | (2006.01) |
| *C12N 15/74* | (2006.01) |

(52) U.S. Cl.
CPC .............. *C12N 1/12* (2013.01); *A23K 10/16* (2016.05); *A23L 17/60* (2016.08); *A23L 33/105* (2016.08); *A61K 8/9717* (2017.08); *C12N 1/06* (2013.01); *C12N 15/74* (2013.01); *A23V 2002/00* (2013.01)

(58) Field of Classification Search
CPC combination set(s) only.
See application file for complete search history.

(56) References Cited

U.S. PATENT DOCUMENTS

| | | |
|---|---|---|
| 2014/0308310 A1 | 10/2014 | Köhler et al. |
| 2017/0037360 A1 | 2/2017 | Suzuki et al. |
| 2018/0274002 A1 | 9/2018 | Cagnac et al. |

FOREIGN PATENT DOCUMENTS

| | | |
|---|---|---|
| JP | 3459275 B2 | 10/2003 |
| JP | 2014524248 A | 9/2014 |
| JP | 2015-192598 | * 11/2015 |
| JP | 2015192598 A | 11/2015 |
| JP | 2017-123816 | * 7/2017 |
| JP | 2017123816 A | 7/2017 |
| WO | 92/22648 A1 | 12/1992 |
| WO | 2013/023873 A1 | 2/2013 |
| WO | 2015159959 A1 | 10/2015 |
| WO | 2017050917 A | 3/2017 |

OTHER PUBLICATIONS

Eren et al. (Submitted Oct. 24, 2016. Accession No. KY0334311).*
Yoon et al (Galdieria maxima strain Ippas P507 ribulose-1 ,5-bisphosphate carboxylase/oxygenase large subunit (rbcL) gene, partial cds; chloroplast, Database GenBank, Accession No. AY391370. 1, Jul. 26, 2016).*
Office Action for European Application 18884061.5 mailed Sep. 4, 2025.
Vona Vincenza et al: "Growth, photosynthesis, respiration, and intracellular free amino acid profiles in the unicellular alga Cyanidium caldarium . Effect of nutrient limitation and resupply", Physiologia Plantarum., vol. 85, No. 4, Aug. 1, 1992 (Aug. 1, 1992), pp. 652-658, XP093306124, DK, ISSN: 0031-9317, DOI: 10.1111 /j.1399-3054.1992.tb04768.x.
Sloth J K et al: "Accumulation of phycocyanin in heterotrophic and mixotrophic cultures of the acidophilic red alga Galdieria sulphuraria", Enzyme and Microbial Technology, Stoneham, MA, US, vol. 38, No. 1-2, Jan. 3, 2006 (Jan. 3, 2006), pp. 168-175, XP025094927, ISSN: 0141-0229, DOI: 10.1016/J.ENZMICTEC.2005.05.010.
Chinese Office Action for Application No. 2018/800761988, mailed Jun. 30, 2023 (with English Translation).
Extended European Search Report in related, co-pending EP Application No. 18884061.5, mailed Jul. 20, 2021.
Database UniProx, May 1, 2013, RecName: Full=Glutamate decarboxylase {EC0:0000256:ARBA:ARBA00012421. EC0:0000256:RuleBase:RU361171}; EC=4. 1. 1. 15 {EC0:0000256:ARBA:ARBA00012421. EC0:0000256: RuleBase:RU361171};. XP002803587. retrieved from EBI accession No. UNIPROT:M1VFU6 Database accession No. M1VFU6 * sequence *& Motomichi Matsuzaki et al: "Genome sequence of the ultrasmall unicellular red alga Cyanidioschyzon merolae IOD". Nature.vol. 428. No. 6983.Apr. 8, 2004 (Apr. 8, 2004). pp. 653-657.
Osami Misumi, et al., "Genome Analysis and Its Significant in Four Unicellular Algae, Cynidioschyzon Merola, Ostreococcus Tauri, Chlamydomonas Reinhardtii, and Thalassiosira Pseudonana", Nournal of Plant Research, Springer-Verlag, vol. 121, No. 1, Dec. 12, 2007, pp. 3-17.
Rahman, et al., "Thermostable Phycocyanin from the Red Microalga Cynidioschyzon Merolae, a New Natural Blue Food Colorant", Journal of Applied Phycology, Nov. 21, 2016, XP55324295, NL, ISSN: 0921-8971.

(Continued)

*Primary Examiner* — Jennifer E Graser

(74) *Attorney, Agent, or Firm* — Thomas I Horstemeyer, LLP

(57) ABSTRACT

Provided is an alga belonging to Cyanidiophyceae having a diploid cell and a haploid cell form. Also provided is a nutrient composition containing an alga belonging to Cyanidiophyceae or an extract thereof.

7 Claims, 17 Drawing Sheets

Specification includes a Sequence Listing.

(56) References Cited

OTHER PUBLICATIONS

Atsunobu Kondo et al., Phylogenetic analysis of cyanidian algae (Cyanidiales, Rhodophyta), using 18S rRNA gene sequences, The Japanese Journal of Phycology 2004, vol. 52, pp. 195-199.

Cozzolino S. et al., Molecular variation in Galdieria sulphuraria (Galdieri) Merola and its bearing on taxonomy, Hydrobiologia, 433, 2000, pp. 145-151.

Fujiwara T et al., A nitrogen source-dependent inducible and repressible gene expression system in the red alga Cyanidioschyzon merolae, Frontiers in Plant Science, Aug. 2015, vol. 6: 657.

Fujiwara T et al., Gene Targeting in the Red Alga Cyanidioschyzon merolae: Singleand Multi-Copy Insertion Using Authentic and Chimeric Selection Markers, PLOS ONE, Sep. 2013, vol. 8(9): e73608.

International Search Report in co-pending, related PCT Application No. PCT/JP2018/043696, mailed Mar. 5, 2019.

Minoda A et al., Improvement of Culture Conditions and Evidence for Nuclear Transformation by Homologous Recombination in a Red Alga, Cyanidioschyzon merolae 10D, Plant Cell Physiol., Jun. 2004, vol. 45 No. 6, pp. 667-671.

Misumi O et al., Cyanidioschyzon merolae Genome. A Tool for Facilitating Comparable Studies on Organelle Biogenesis in Photosynthetic Eukaryotes, Plant Physiology, Feb. 2005, vol. 137, pp. 567-585.

Office Action re JP Application No. 2019-557254, mailed Apr. 7, 2020.

Pinto, G., Cyanidiophyceae: Looking Back—Looking Forward, J. Seckbach (ed.), Algae and Cyanobacteria in Extreme Environments, 2007, Springer, pp. 389-397.

Shunsuke Hirooka et al., Cultivation of Acidophilic Algae Galdieria sulphuraria and Pseudochlorella sp. YKT1 in Media Derived from Acidic Hot Springs, Frontiers in microbiology, vol. 7, Dec. 20, 2016, pp. 1-11.

Yoon, H. S. et al., Galdieria maxima strain Ippas P507 ribulose-1,5-bisphosphate carboxylase/oxygenase large subunit (rbcL) gene, partial cds; chloroplast, Database GenBank, Accession No. AY391370. 1, Jul. 26, 2016.

Chinese Office Action for Application No. 2018/800761988, mailed Jun. 28, 2023 (with English Translation).

Office Action in related Korean Application No. 10/2020/7018058, mailed Oct. 23, 2023.

Yuki Kasai, et al., Construction of a self-cloning system in the unicellular green alga Pseudochoricystis ellipsoidea, Biotechnology of Biofuels (2015 (8:94, pp. 1-12).

GenBankAccession No. 063676 (Oct. 16, 1997).

Ohta et al (J. Plant Fes. 1997. 110: 235-245).

GenBankAccession No. D63676 (Oct. 16, 1997).

Office Action for U.S. Appl. No. 19/182,345 mailed Dec. 10, 2025.

Mikayama et al., "Molecular cloning and functional expression of a cDNA encoding glycosylation-inhibiting factor", (Nov. 1993. Proc.Natl.Acad.Sci. USA, vol. 90 : 10056-10060).

* cited by examiner

GAD-HA, 66 kDa (error bar = standard deviation: *n*=3)

HKN1_allele 1                    SEQ ID NO:12
HKN1_allele 2                    SEQ ID NO:13
HKN1 CHYZON-LIKE
_allele 1                        SEQ ID NO:14

FIG. 9

Galdieria sulphuraria SAG108.79

Galdieria partita NBRC 102759

APCC PROMOTER
(CMO250C 5' UTR)

β-TUBULIN
3' UTR

CPCC PROMOTER
(CMP166C 5' UTR)

Ubiquitin
3' UTR

TOCOPHEROL
CYCLASE
(CML326C)

3×HA
tag $URA_{Cm-Cm}$

HOMOGENTISATE
PHYTYLTRANSFERASE
(CMN202C)

3×FLAG
tag

TC-HA
GFP VE

HPT-FLAG
GFP VE (kDa)

— 100

— 75

— 50

— 37

— 25

MICROALGAE AND USE FOR SAME

CROSS-REFERENCE TO RELATED APPLICATIONS

This application is a divisional application of U.S. Non-provisional application Ser. No. 16/766,946 filed on Oct. 27, 2020, which is a US national phase application of International Application No. PCT/JP2018/043696 filed on Nov. 28, 2018, which claims the benefit of and priority to (1) Japanese Patent Application No. 2017-228396 filed on Nov. 28, 2017, (2) Japanese Patent Application No. 2017-228394 filed on Nov. 28, 2017, (3) Japanese Patent Application No. 2018-177416 filed on Sep. 21, 2018, and (4) Japanese Patent Application No. 2018-101753 filed on May 28, 2018, the contents of which are incorporated by reference herein in their entireties.

STATEMENT REGARDING DEPOSIT OF BIOLOGICAL MATERIALS

The algal strains YFU3 (FERM BP-22334) and HKN1 (FERMP BP-22333) referenced herein were deposited on May 30, 2017 at the Research Organization of Information and Systems National Institute of Genetics, Yata1111, Mishima, Shizuoka 411-8540, JAPAN.

CROSS REFERENCE TO SEQUENCE LISTING

The genetic components described herein are referred to by sequence identifier numbers (SEQ ID NO). The sequence listing in written computer readable format (CRF) as an xml file named "51966-1060_Sequence_Listing.xml" created on Apr. 17, 2025, and having a size of 88,922 bytes, is incorporated by reference in its entirety.

TECHNICAL FIELD

The present invention relates to novel microalgae and use for the same. More specifically, the present invention relates to novel microalgae, a method for producing the microalgae as haploids, and the like. The present invention also relates to a nutrient composition and a method for producing a nutrient.

The present application claims priorities based on Japanese Patent Application Nos. 2017-228394 and 2017-228396 filed in Japan on Nov. 28, 2017, Japanese Patent Application No. 2018-101753 filed in Japan on May 28, 2018, and Japanese Patent Application No. 2018-177416 filed in Japan on Sep. 21, 2018, the contents of which are incorporated herein by reference.

BACKGROUND ART

Microalgae have a carbon dioxide fixation capacity higher than that of terrestrial plants and do not compete with agricultural products for their growing places. Therefore, some species of the microalgae are cultured in large quantities and used industrially as feed, functional foods, cosmetic materials, and the like.

In a case where the microalgae are used industrially, in view of costs and the like, microalgae that can be cultured outdoors in large quantities are desirable. However, the microalgae that can be cultured outdoors in large quantities need to meet requirements such as being resistant to environmental changes (light, temperature, and the like), being cultivable under conditions where other organisms cannot survive, and being able to grow to high density. Accordingly, hitherto, only a few species such as *Chlorella, Euglena, Dunaliella*, and *Spirulina* have been practically used in industry.

One of the characteristic of the aforementioned species of algae is that they can be cultured in an environment, such as an environment with a high salt concentration, high pH, and low pH, where other organisms are difficult to grow. These species of algae are rich in amino acids and vitamins and are used as raw materials for functional foods or supplements.

Meanwhile, the algae belonging to Cyanidiophyceae, which are unicellular primitive red algae, grow preferentially in acidic hot springs containing sulfuric acid. Cyanidiophyceae includes Cyanidioschyzon, Cyanidium, and Galdieria (Non-Patent Document 1). As haploid algae, only Cyanidioschyzon merolae is known (Non-Patent Document 2). Cyanidioschyzon merolae has no rigid cell wall (Non-Patent Documents 1 and 2).

Cyanidioschyzon merolae is constituted with a very simple set of cell organelles, and the genome sequence thereof has been completely decoded. Therefore, Cyanidioschyzon merolae is used as a model organism for basic research on photosynthetic organisms, and the development of techniques for modifying the gene thereof is also making progress (Non-Patent Documents 3 and 4).

CITATION LIST

Non-Patent Literature

[Non-Patent Document 1]
Pinto, G. (2007) Cyanidiophyceae: looking back-looking forward, In: J. Seckbach (ed.) Algae and Cyanobacteria in Extreme Environments.Springer, Dordrecht, The Netherlands, pp. 389-397.
[Non-Patent Document 2]
Misumi O et al. (2005) Cyanidioschyzon merolae Genome. A Tool for Facilitating Comparable Studies on Organelle Biogenesis in Photosynthetic Eukaryotes. Plant Physiol. 137 (2): 567-585.
[Non-Patent Document 3]
Fujiwara T et al. (2013) Gene targeting in the red alga Cyanidioschyzon merolae: single- and multi-copy insertion using authentic and chimeric selection markers. PLOS ONE. September 5; 8 (9): e73608.
[Non-Patent Document 4]
Fujiwara T et al. (2015) A nitrogen source-dependent inducible and repressible gene expression system in the red alga Cyanidioschyzon merolae. Front Plant Sci. August 26; 6: 657.

SUMMARY OF INVENTION

Technical Problem

As described above, hitherto, microalgae practically used in industry have been limited to several species of algae.

Therefore, an object of the present invention is to provide novel microalgae that can be used industrially and a method of using the novel microalgae. Another object of the present invention is to provide a nutrient composition using microalgae rich in nutrients, and a method for producing a nutrient using the microalgae.

Still another object of the present invention is to provide a method for preparing haploid cells from diploid algal cells, haploid cells prepared by the method, and a haploid algal cell population obtained by culturing the haploid cells.

Yet another object of the present invention is to provide a method for preparing diploid cells from haploid algal cells, diploid cells prepared by the method, and a diploid algal cell population obtained by culturing the diploid cells.

Another object of the present invention is to provide algal cells transformed by self-cloning or multiple self-cloning by using haploid algal cells.

Solution to Problem

The inventors of the present invention have found that among the algae belonging to Cyanidiophyceae, there are a generation of haploid cells and a generation of diploid cells. Furthermore, the inventors have found that among the algae belonging to Cyanidiophyceae, those having a rigid cell wall are diploid cells, and found a method for inducing cells having no rigid cell wall from the diploid cells having a rigid cell wall. Furthermore, the inventors have found that the cells having no rigid cell wall obtained by the above method are haploid cells. In addition, the inventors have found that the algae belonging to Cyanidiophyceae are rich in nutrients such as amino acids and vitamins. Based on these findings, the inventors of the present invention have accomplished the following invention.

The present invention includes the following aspects.

(1) An Alga belonging to Cyanidiophyceae having a diploid cell form and a haploid cell form.

(1-2) A cell population of the alga according to (1), consisting of a cell population of the diploid cell form, in which the alga belonging to Cyanidiophyceae.

(1-3) A cell population of the alga according to (1), consisting of a cell population of the haploid cell form, in which the alga belonging to Cyanidiophyceae.

(1-4) A cell population of the alga according to (1), in which the alga belong to Cyanidiophyceae, and a cell population of the diploid cell form and a cell population of the haploid cell form are mixed together.

(2) The alga according to (1), in which the haploid cell form is ruptured under a condition of pH 7.

(3) The alga according to (1) or (2), in which a base sequence of a ribulose 1,5-bisphosphate carboxylase/oxygenase large subunit gene has identity equal to or higher than 90% with a base sequence shown in SEQ ID NO: 1 or 2.

(4) The alga according to (3), which is selected from the group consisting of Cyanidium sp. YFU3 (FERM BP-22334), Cyanidium sp. HKN1 (FERM BP-22333), and a mutant of these.

(5) The alga according to any one of (1) to (4), which is a transformant.

(6) The alga according to (5), in which the transformant is prepared by self-cloning.

(7) The alga according to any one of (1) to (6), which is the haploid cell form.

(8) A method for producing a haploid alga, including (a) step of culturing a diploid cell (alga) of the alga according to any one of (1) to (6), and (b) step of isolating a haploid cell (alga) that are generated during the culturing.

(9) The method for producing a haploid alga according to (8), in which the culturing in the step (a) is performed under a condition of temperature of 30° C. to 50° C., pH of 1.0 to 5.0, and $CO_2$ concentration of 1% to 3%.

(10) An alga culture containing the alga according to any one of (1) to (7), wherein a ratio of the number of haploid cells of the alga to the total number of cells of alga contained in the alga culture is 70% to 100%.

(11) A drying and swelling treatment product, which is obtained by subjecting the alga according to any one of (1) to (7) to a drying and swelling treatment.

The present invention also includes the following aspects.

(12) A method for producing a nutrient, including (a) step of disrupting a cell of the alga according to any one of (1) to (7) so as to obtain a cell disruption product, and (b) step of separating a nutrient from the cell disruption product.

(13) The method for producing a nutrient according to (12), in which the nutrient is at least one nutrient selected from the group consisting of amino acids, vitamins, proteins, lipids, and dietary fiber.

(14) The method for producing a nutrient according to (13), in which the amino acids are at least one kind of amino acid selected from the group consisting of isoleucine, leucine, lysine, methionine, cystine, phenylalanine, tyrosine, threonine, tryptophan, valine, arginine, histidine, alanine, aspartic acid, glutamic acid, glycine, proline, serine, and γ-aminobutyric acid.

(15) The method for producing a nutrient according to (13), in which the vitamins are at least one kind of vitamin selected from the group consisting of vitamin A, β-carotene, vitamin C, vitamin E, vitamin $K_1$, and vitamin $K_2$.

(16) The method for producing a nutrient according to any one of (12) to (15), in which the disrupting of a cell in the step (a) is performed by at least one kind of treatment selected from the group consisting of a neutralization treatment, a hypotonic treatment, and a freeze-thaw treatment.

(17) The method for producing a nutrient according to any one of (12) to (16), further including a step of subjecting the alga according to any one of (1) to (7) to a low-temperature treatment at a temperature of 0° C. to 5° C. before the step (a).

(18) A nutrient composition containing the alga according to any one of (1) to (7) or an extract thereof.

(19) A food containing the nutrient composition according to (18).

(20) The food according to (19), which is a functional food or a dietary supplement.

(21) A feed or a pet food containing the nutrient composition according to (18).

(22) A cosmetic containing the nutrient composition according to (18).

(23) A nutritional supplement containing the alga according to any one of (1) to (7) or an extract thereof.

(24) A food containing the nutritional supplement according to (23).

(25) The food according to (24), which is a functional food or a nutritional supplement.

(26) A feed or a pet food containing the nutritional supplement according to (23).

(27) A cosmetic containing the nutritional supplement according to (23).

(28) A composition for supplying a nutrient, containing the nutritional supplement according to (23).

(29) The composition for supplying a nutrient according to (28), which is a food.

(30) The composition for supplying a nutrient according to (29), which is a functional food or a dietary supplement.

(31) The composition for supplying a nutrient according to (28), which is a feed or a pet food.

(32) The composition for supplying a nutrient according to (28), which is a cosmetic.

(33) A nutrient composition containing the alga culture according to (10) or an extract thereof.

(34) A food containing the nutrient composition according to (33).

(35) The food according to (34), which is a functional food or a dietary supplement.

(36) A feed or a pet food containing the nutrient composition according to (33).

(37) A cosmetic containing the nutrient composition according to (33).

(38) A nutritional supplement containing the alga culture according to (10) or an extract thereof.

(39) A food containing the nutritional supplement according to (38).

(40) The food according to (39), which is a functional food or a nutritional supplement.

(41) A feed or a pet food containing the nutritional supplement according to (38).

(42) A cosmetic containing the nutritional supplement according to (38).

(43) A composition for supplying a nutrient, containing the nutritional supplement according to (38).

(44) The composition for supplying a nutrient according to (43), which is a food.

(45) The composition for supplying a nutrient according to (44), which is a functional food or a dietary supplement.

(46) The composition for supplying a nutrient according to (43), which is a feed or a pet food.

(47) The composition for supplying a nutrient according to (43), which is a cosmetic.

(48) A method for producing a nutrient, including (a) step of collecting an alga from the alga culture according to (10), (b) step of disrupting a cell of the alga so as to obtain a cell disruption product, and (c) step of separating at least one kind of nutrient from the cell disruption product.

(49) The method for producing a nutrient according to (48), in which the nutrient is at least one kind of nutrient selected from the group consisting of amino acids, vitamins, proteins, lipids, and dietary fiber.

(50) The method for producing a nutrient according to (49), in which the amino acids are at least one kind of amino acid selected from the group consisting of isoleucine, leucine, lysine, methionine, cystine, phenylalanine, tyrosine, threonine, tryptophan, valine, arginine, histidine, alanine, aspartic acid, glutamic acid, glycine, proline, serine, and γ-aminobutyric acid.

(51) The method for producing a nutrient according to (49), in which the vitamins are at least one kind of vitamin selected from the group consisting of vitamin A, β-carotene, vitamin C, vitamin E, vitamin $K_1$, and vitamin $K_2$.

(52) The method for producing a nutrient according to any one of (48) to (51), in which the disrupting of a cell in the step (a) is performed by at least one kind of treatment selected from the group consisting of a neutralization treatment, a hypotonic treatment, a freeze-thaw treatment, and a drying and swelling treatment.

The present invention also includes the following aspects.

(53) A nutrient composition containing an alga belonging to Cyanidiophyceae or an extract thereof.

(54) The nutrient composition according to (53), in which the alga is a haploid alga.

(55) The nutrient composition according to (53) or (54), in which the alga undergoes cell rupture under a condition of pH 7.

(56) The nutrient composition according to any one of (53) to (55), in which the alga belongs to Cyanidioschyzon.

(57) The nutrient composition according to any one of (53) to (56), in which the alga is a transformant having an increased intracellular content of at least one kind of nutrient.

(58) The nutrient composition according to (57), in which the transformant is prepared by self-cloning.

(59) The nutrient composition according to any one of (53) to (58), containing at least one kind of nutrient selected from the group consisting of amino acids, vitamins, proteins, lipids, and dietary fiber.

(60) A food containing the nutrient composition according to any one of (53) to (59).

(61) The food according to (60), which is a functional food or a dietary supplement.

(62) A feed or a pet food containing the nutrient composition according to any one of (53) to (59).

(63) A cosmetic containing the nutrient composition according to any one of (53) to (59).

(64) A method for producing a nutrient, including (a) step of disrupting a cell of an alga belonging to Cyanidiophyceae so as to obtain a cell disruption product, and (b) step of separating at least one kind of nutrient from the cell disruption product.

(65) The method for producing a nutrient according to (64), in which the nutrient is at least one kind of nutrient selected from the group consisting of amino acids, vitamins, proteins, lipids, and dietary fiber.

(66) The method for producing a nutrient according to (65), in which the amino acids are at least one kind of amino acid selected from the group consisting of isoleucine, leucine, lysine, methionine, cystine, phenylalanine, tyrosine, threonine, tryptophan, valine, arginine, histidine, alanine, aspartic acid, glutamic acid, glycine, proline, serine, and γ-aminobutyric acid.

(67) The method for producing a nutrient according to (65), in which the vitamins are at least one kind of vitamin selected from the group consisting of vitamin A, β-carotene, vitamin $B_1$, vitamin $B_2$, vitamin $B_6$, vitamin C, vitamin E, vitamin $K_1$, vitamin $K_2$, niacin, inositol, folic acid, and biotin.

(68) The method for producing a nutrient according to any one of (64) to (67), in which the alga is a haploid alga.

(69) The method for producing a nutrient according to any one of (64) to (68), in which a cell of the alga is ruptured under a condition of pH 7.

(70) The method for producing a nutrient according to any one of (64) to (69), in which the alga belong to Cyanidioschyzon.

(80) The method for producing a nutrient according to any one of (64) to (70), in which the alga is a transformant having an increased intracellular content of at least one kind of nutrient.

(81) The method for producing a nutrient according to (80), in which the transformant is prepared by self-cloning.

(82) The method for producing a nutrient according to any one of (64) to (81), in which the disrupting of a cell in the step (a) is performed by at least one kind of treatment selected from the group consisting of a neutralization treatment, a hypotonic treatment, a freeze-thaw treatment, and a drying and swelling treatment.

The present invention also includes the following aspects.

(83) A nutritional supplement containing an alga belonging to Cyanidiophyceae or an extract thereof.

(84) The nutritional supplement according to (83), in which the alga is a haploid alga.

(85) The nutritional supplement according to (83) or (84), in which a cell of the alga is ruptured under a condition of pH 7.

(86) The nutritional supplement according to any one of (83) to (85), in which the alga belong to Cyanidioschyzon.

(87) The nutritional supplement according to any one of (83) to (86), in which the alga is a transformant having an increased intracellular content of at least one kind of nutrient.

(88) The nutritional supplement according to (87), in which the transformant is prepared by self-cloning.

(89) The nutritional supplement according to any one of (83) to (88), which is for supplying at least one kind of nutrient selected from the group consisting of amino acids, vitamins, proteins, lipids, and dietary fiber.

(90) A food containing the nutritional supplement according to any one of (83) to (89).

(91) The food according to (90), which is a functional food or a dietary supplement.

(92) A feed or a pet food containing the nutritional supplement according to any one of (83) to (89).

(93) A cosmetic containing the nutritional supplement according to any one of (83) to (89).

(94) A composition for supplying a nutrient, containing the nutritional supplement according to any one of (83) to (89).

(95) The composition for supplying a nutrient according to (94), which is a food.

(96) The composition for supplying a nutrient according to (95), which is a functional food or a dietary supplement.

(97) The composition for supplying a nutrient according to (94), which is a feed or a pet food.

(98) The composition for supplying a nutrient according to (94), which is a cosmetic.

(99) The composition for supplying a nutrient according to any one of (94) to (98), which is for supplying at least one kind of nutrient selected from the group consisting of amino acids, vitamins, proteins, lipids, and dietary fiber.

The present invention also includes the following aspects.

(100) A method for producing a diploid alga, including (a) step of mixing together two or more kinds of haploid cells of the alga according to any one of (1) to (6) and culturing the mixture, and (b) step of isolating a diploid cell generated during the culturing.

(101) The method for producing a diploid alga according to (100), in which the alga is selected from the group consisting of Cyanidium sp. YFU3 (FERM BP-22334), Cyanidium sp. HKN1 (FERM BP-22333), Cyanidioschyzon merolae, and mutants of these.

(102) A diploid cell of Cyanidium sp. YFU3 (FERM BP-22334) or a mutant thereof.

(103) A diploid cell of a Cyanidium sp. HKN1 (FERM BP-22333) or a mutant thereof.

(104) A diploid cell of Cyanidioschyzon merolae.

(105) The method for producing a haploid alga according to (8), in which the alga is selected from the group consisting of alga belonging to Galdieria and alga belonging to Cyanidium.

(106) A haploid cell of alga belonging to Galdieria.

(107) The haploid cell according to (106), in which the alga belonging to Galdieria are Galdieria sulphuraria or Galdieria partita.

(108) A haploid cell of an alga belonging to Cyanidium.

(109) The haploid cell according to (108), in which the alga belonging to Cyanidium are Cyanidium sp. YFU3 (FERM BP-22334) or Cyanidium sp. HKN1 (FERM BP-22333).

Advantageous Effects of Invention

According to the present invention, there are provided novel microalgae which can be industrially used and a method of using the microalgae. Furthermore, according to the present invention, there are provided a nutrient composition using microalgae rich in nutrients, and a method for producing a nutrient by using the microalgae.

In addition, according to the present invention, there are provided a method for preparing haploid cells from diploid algal cells, haploid cells prepared by the method, and a haploid algal cell population obtained by culturing the haploid cells.

Moreover, according to the present invention, there are provided a method for preparing diploid cells from haploid algal cells, diploid cells prepared by the method, and a diploid algal cell population obtained by culturing the diploid cells.

The present invention also provides algal cells transformed by self-cloning or multiple self-cloning by using haploid algal cells.

BRIEF DESCRIPTION OF DRAWINGS

FIG. 9 shows the results of agarose electrophoresis in which YFU3 (haploid), HKN1 (haploid), and Cyanidioschyzon merolae are compared with each other in terms of the size of ribosomal DNA ITS1.

DESCRIPTION OF EMBODIMENTS

[Algae Belonging to Cyanidiophyceae]

Figure 1A:
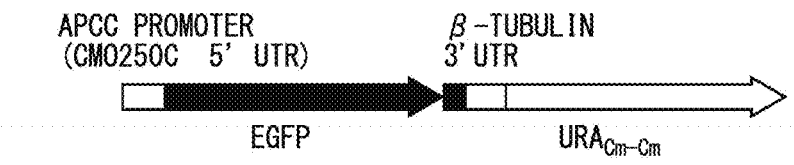
FIG. 1A shows the construct of a fragment for transformation (EGFP/URA$_{Cm-Cm}$ fragment) used in Example 2.

As shown in Examples which will be described later, it has been found that the algae belonging to Cyanidiophyceae are rich in nutrients such as amino acids, vitamins, proteins, lipids, and dietary fiber. Therefore, the present invention provides a nutrient composition, a nutritional supplement, a food, a feed, a pet food, a pet food, a cosmetic, and the like using the algae belonging to Cyanidiophyceae. Furthermore, the present invention provides a method for producing a nutrient using the algae belonging to Cyanidiophyceae.

Taxonomically, Cyanidiophyceae is classified into Rhodophyta, Cyanidiophyceae. Currently, three genera of Cyanidioschyzon, Cyanidium, and Galdieria are classified into Cyanidiophyceae. In the nutrient composition according to an embodiment of the present invention and the like may use algae belonging to any of the above genera.

Whether or not certain algae belong to Cyanidiophyceae can be determined, for example, by phylogenetic analysis using the base sequence of an 18S rRNA gene or a chloroplast rbcL gene. The phylogenetic analysis may be performed by a known method.

In the present specification, "haploid cell form" means that the cell as an observation target has one set of genetic information, and "diploid cell form" means that the cell as an observation target has two sets of genetic information.

Whether a certain cell is haploid or diploid can be determined by measuring the content of DNA in the cell, and also can be determined by a next-generation sequencer which will be described later.

In the present specification, "having a diploid cell form and a haploid cell form" means that a cell of an alga belonging to Cyanidiophyceae collected from nature is the haploid cell form in a case, and is the diploid cell form in another case, and also means that the cell of an alga belonging to Cyanidiophyceae which is unknown hitherto and created by the method of the present invention is the haploid cell form in a case and is the diploid cell form in another case.

In the present specification, "cell population of diploid cell form" and "cell population of haploid cell form" may be a clonal cell population or a non-clonal cell population.

Among the algae belonging to Cyanidiophyceae, Cyanidioschyzon merolae is known to have no rigid cell wall. Most of the algae belonging to Cyanidiophyceae other than Cyanidioschyzon merolae have been found as algal cells having a rigid cell wall. As shown in Examples which will be described later, it has been confirmed that these cells having a rigid cell wall are diploids. However, by the method according to an embodiment of the present invention that will be described later, it is possible to create a haploid cell form of algal cells, and many of the created haploid algal cells do not have a rigid cell wall. The haploid cell form of algal cells that do not have a rigid cell wall can be disrupted by a relatively mild treatment such as a neutralization treatment, a hypotonic treatment, or a freeze-thaw treatment. In the present specification, "having no rigid cell wall" means that a cell is ruptured by any of the following cell rupturing treatments (A) to (C).

(A) Algal cells are suspended in an isotonic solution at pH 7 and left for one week or longer.

(B) Algal cells are suspended in distilled water and left for 1 minute or longer.

(C) Algal cells are subjected to a drying treatment and suspended in an isotonic solution at pH 7.

In the above (A) to (C), in a case where the algal cells are cultured cells, the medium may be removed by centrifugation or the like before each treatment is performed, and the algal cells may be washed with an isotonic solution or the like.

In the above (A) and (C), examples of the isotonic solution include a pH 7 buffer containing 10% sucrose and 20 mM HEPES.

In the above (C), examples of the drying treatment include drying in a refrigerator (4° C.), freeze-drying, and the like. For the drying treatment, the precipitate of algal cells collected by centrifugation is used. In a case where the cells are dried in a refrigerator, the drying treatment time depends on the amount of algal cells, and is, for example, 3 days or longer.

Whether or not the cells rupture has occurred can be determined by performing centrifugation (1,500×g, 3 minutes) on the algal cell suspension after the cell rupturing treatments (A) to (C) described above, and calculating a ratio of the mass of proteins in the centrifugal supernatant to the total mass of proteins in the algal cell suspension. Specifically, in a case where a rupture rate determined by the following equation is equal to or higher than 20%, it can be determined that cell rupture has occurred.

$$\text{Rupture rate} = \frac{\text{Protein content in centrifugal supernatant (mass g)}}{\text{Total protein content in algal suspension (mass g)}} \times 100(\%) \qquad \text{[Equation 1]}$$

Alternatively, in a case where the algal cells in the algal cell suspension are observed using an optical microscope (for example, at a magnification of 600×), and the ratio of ruptured cells to the total number of the algal cells is found to be about equal to or higher than 10% and preferably about equal to or higher than 20%, it may be determined that cell rupture has occurred.

In the cell rupturing treatments (A) to (C) described above, an isotonic solution at pH 7 can be used. Accordingly, it can be said that the cells ruptured by any of the cell rupturing treatments (A) to (C) are cells that are ruptured under the condition of pH 7.

Not only the algae belonging to Cyanidioschyzon, but also the algae that undergo cell rupture under the condition of pH 7 are preferable because it is easy to extract nutrients from such algae. In addition, such algae also have an advantage that even though the algal cells are added as themselves to a nutritional supplement or the like which will be described later, the nutrients in the algal cells are easily absorbed after the intake of the nutritional supplement. Therefore, in the nutrient composition according to the present embodiment, the alga, which belongs to Cyanidiophyceae and undergo cell rupture under the condition of pH 7, can be suitably used.

Whether or not certain alga undergoes cell rupture under the condition of pH 7 can be determined by immersing the algal cell in a buffer at pH 7 or the like, observing the cell for about 10 to 30 minutes, and checking whether or not the algal cells are ruptured.

In a case where the algal cell has no a rigid cell wall, by the observation using an optical microscope (for example, at a magnification of 600×), generally, a cell wall is not observed.

Generally, Cyanidioschyzon merolae does not undergo cell rupture even being subjected to a mild hypotonic treatment under the condition of pH equal to or lower than 6. Therefore, whether or not cell rupture occurs due to the mild hypotonic treatment under the condition of pH equal to or lower than 6 does not exert an influence on determining whether or not the alga has a rigid cell wall.

Among the algae belonging to Cyanidiophyceae, the algae belonging to Cyanidioschyzon, particularly, Cyanidioschyzon merolae, is characterized by being a haploid. Furthermore, these algae have no rigid cell wall. Accordingly, the algae belonging to Cyanidioschyzon, particularly, Cyanidioschyzon merolae, can be relatively easily transformed using gene recombination techniques. For example, as shown in Examples which will be described later, by using a gene recombination technique, it is possible to prepare a transformant having an increased intracellular content of a nutrient.

Not only the algae belonging to Cyanidioschyzon, particularly, Cyanidioschyzon merolae, but also haploid algae are preferable because these algae can be relatively easily transformed. For example, the haploid cells of algae, which belong to Cyanidiophyceae having a diploid cell form and a haploid cell form which will be described later, is preferable because these algae can be relatively easily transformed. Therefore, in the nutrient composition and the like according to the embodiment of the present invention, the haploid algae belonging to Cyanidiophyceae can be suitably used.

Whether certain algae are haploid can be determined by checking the number of copies of the same loci. That is, in a case where the copy number of the same loci is 1, the algae are determined to be haploid.

Furthermore, for example, whether certain algae are haploid can also be determined using a next-generation sequencer or the like. For example, whole genome sequence reads are acquired by a next-generation sequencer or the like, the sequence reads are assembled, and then the sequence reads are mapped for the sequence obtained by the assembling. In diploids, the difference in base between alleles are found in various regions on the genome. However, in haploids, because only one allele is present, no such regions are found.

Furthermore, in a case where certain algae are homodiploid, whether the algae are haploid or diploid can be determined by measuring the DNA content in the cells. The DNA content in haploid cells is one half of the DNA content in diploid cells.

Examples of the haploid algae, which belong to Cyanidiophyceae and undergo cell rupture under the condition of pH 7, include algae belonging to Cyanidioschyzon. Currently, only one species of Cyanidioschyzon merolae is classified into Cyanidioschyzon. Therefore, Cyanidioschyzon merolae is a suitable example of algae used in the nutrient composition or the like according to the embodiment of the present invention.

In addition, not only the haploid of algae belonging to Cyanidioschyzon other than Cyanidioschyzon merolae that is obtained by the present invention and is unknown hitherto, but also the haploid of algae belonging to Galdieria and the haploid of algae belonging to Cyanidium are suitable examples as well.

The algae belonging to Cyanidiophyceae can grow to high density (about 30 g/L) under high temperature (30° C. to 55° C.) and acidic (pH 0.1 to 3.0) conditions. Under such a high-temperature and acidic environment, other organisms are difficult to grow. Therefore, the algae belonging to Cyanidiophyceae are suitable for being cultured outdoors in large quantities.

In addition, the algae belonging to Cyanidiophyceae can grow not only under high-temperature and acidic conditions but also under a relatively wide range of environmental conditions such as a medium-temperature environment (15° C. to 30° C.) and a neutral environment (about pH 6). Therefore, the culture conditions can be changed according to the region and the season. In this respect, the algae belonging to Cyanidiophyceae are also suitable for being cultured outdoors in large quantities.

Furthermore, the algae belonging to Cyanidiophyceae exhibits high salt tolerance and can grow under high salt (300 mM NaCl) conditions. In addition, the range of optical intensity at which the algae can grow is wide. The algae can grow to high density in a range of 5 to 1,500 mol/m$^2$s, and can grow under strong light.

As will be shown in Examples which will be described later, the algae belonging to Cyanidiophyceae are rich in nutrients such as amino acids, vitamins, proteins, lipids, and dietary fiber. Particularly, it has been confirmed that the algae belonging to Cyanidiophyceae contain amino acids and vitamins at a higher concentration compared to the conventionally used algae (*Chlorella, Euglena*, and *Spirulina*). Furthermore, the composition of components of the algae is also specific. Therefore, by using the algae belonging to Cyanidiophyceae, it is possible to manufacture a nutrient composition, a nutritional supplement, and the like rich in nutrients selected from the group consisting of amino acids, vitamins, proteins, lipids, and dietary fiber, particularly, nutrients such as amino acids or vitamins.

In the present specification, "amino acids" mean organic compounds having an amino group and a carboxy group.

Examples of the amino acids contained in the algae belonging to Cyanidiophyceae include isoleucine, leucine, lysine, methionine, cystine, phenylalanine, tyrosine, threonine, tryptophan, valine, arginine, histidine, alanine, aspartic acid, glutamic acid, glycine, proline, serine, γ-aminobutyric acid, and the like. One of the characteristics of the algae belonging to Cyanidiophyceae is that the total amino acid content thereof is higher than that of the conventionally used algae. Furthermore, the content of each of the amino acids in the algae belonging to Cyanidiophyceae tends to be high overall.

For example, the total content of amino acids in the algae belonging to Cyanidiophyceae is 60 to 80 g/100 g based on dry weight. Furthermore, algae belonging to Cyanidiophyceae are also characterized by containing γ-aminobutyric acid. For example, the content of γ-aminobutyric acid in the algae belonging to Cyanidiophyceae is 0.1 to 0.3 g/100 g based on dry weight. In the present specification, "total amino acid content" means a value obtained by adding up the contents of isoleucine, leucine, lysine, methionine, cystine, phenylalanine, tyrosine, threonine, tryptophan, valine, arginine, histidine, alanine, aspartic acid, glutamic acid, glycine, proline, and serine.

In the present specification, "vitamins" mean organic compounds other than carbohydrates, proteins, and lipids among nutrients necessary for the survival of an organism.

Examples of the vitamins contained in the algae belonging to Cyanidiophyceae include vitamin A, β-carotene, vitamin $B_1$, vitamin $B_2$, vitamin $B_6$, vitamin C, vitamin E, vitamin $K_1$, vitamin $K_2$, niacin, inositol, folic acid, biotin, and the like. One of the characteristics of the algae belonging to Cyanidiophyceae is that the content of β-carotene, vitamin C, vitamin E, vitamin $K_1$, vitamin $K_2$, and folic acid among the above vitamins is particularly higher in the algae than in the conventionally used algae.

Regarding the content of each of the vitamins in the algae belonging to Cyanidiophyceae, for example, the content of β-carotene is 200 to 250 mg/100 g based on dry weight, the content of vitamin C is 40 to 70 mg/100 g based on dry weight, the content of vitamin E is 150 to 180 mg/100 g based on dry weight, the content of vitamin $K_1$ is 3,000 to 5,000 μg/100 g based on dry weight, the content of vitamin $K_2$ is 4,000 to 7,000 μg/100 g based on dry weight, and the content of folic acid is 3,500 to 6,500 μg/100 g based on dry weight.

In a case where a human being or a non-human animal ingests algae which have no rigid cell wall among the algae belonging to Cyanidiophyceae, the nutrients described above can be efficiently absorbed into the body of the human being or the non-human animal. Furthermore, in a case where an extract containing the nutrients is prepared from the algae belonging to Cyanidiophyceae, from the algae which have no rigid cell wall, the extract can be prepared by a simple operation such as the cell rupturing treatments (A) to (C) described above.

The algae belonging to Cyanidiophyceae can preferentially grow in an acidic environment of sulfuric acid such as an acidic hot spring containing sulfuric acid. Therefore, the algae can be obtained by being isolated from the acidic hot spring containing sulfuric acid and the like. In addition, the algae belonging to Cyanidiophyceae may be obtained from a culture collection and the like. For example, Cyanidioschyzon merolae can be obtained from the National Institute for Environmental Studies MICROBIAL CULTURE COL-LECTION (16-2 Onogawa, Tsukuba-shi, Ibaraki prefecture, Japan), American Type Culture Collection (ATCC; 10801 University Boulevard Manassas, VA 20110 USA), and the like.

The algae belonging to Cyanidiophyceae can be cultured using a medium for culturing microalgae. The medium is not particularly limited, and examples thereof include an inorganic salt medium containing a nitrogen source, a phosphorus source, trace elements (such as zinc, boron, cobalt, copper, manganese, molybdenum, and iron), and the like. Examples of the nitrogen source include an ammonium salt, a nitrate, and a nitrite, and the like. Examples of the phosphorus source include a phosphate and the like. Examples of the aforementioned medium include a 2× Allen medium (Allen M B. Arch. Microbiol. 1959 32: 270-277.), an M-Allen medium (Minoda A et al. Plant Cell Physiol. 2004 45: 667-71)), an MA2 medium (Ohnuma M et al. Plant Cell Physiol. 2008 January; 49 (1): 117-20.), a modified M-Allen medium, and the like.

As described above, the algae belonging to Cyanidiophyceae can be grown to high density under a relatively wide range of culture conditions. The pH condition can be, for example, pH 1.0 to 6.0, and is preferably pH 1.0 to 5.0. In a case where the algae are cultured outdoors, in order to prevent the growth of other organisms, it is preferable to culture the algae under conditions with a high acidity. The pH of such conditions is, for example, 1.0 to 3.0.

The temperature condition can be, for example, 15° C. to 50° C., and is preferably 30° C. to 50° C. In a case where the algae are cultured outdoors, in order to prevent the growth of other organisms, it is preferable to culture the algae at a high temperature. The temperature of such condition is, for example, 35° C. to 50° C.

The light intensity can be, for example, 5 to 2,000 mol/m²s, and is preferably 5 to 1,500 mol/m²s. In a case where the algae are cultured outdoors, the algae may be cultured under sunlight. In a case where the algae are cultured indoors, the algae may be cultured under continuous light or go through a light-dark cycle (10L:14D or the like).

By being collected through a known method such as centrifugation or filtration and subjected to washing, drying, and the like as appropriate, the algae belonging to Cyanidiophyceae grown by culturing can be used in the nutritional supplement of the present embodiment.

The algae belonging to Cyanidiophyceae are not limited to those isolated from the natural world, and may be algae obtained by the mutation of natural algae belonging to Cyanidiophyceae. The mutation may be spontaneous mutation or induced mutation. For example, Cyanidioschyzon merolae isolated from the natural world is haploid cells. As the genome size of Cyanidioschyzon merolae is small (about 16 Mbp) and the genomic sequence thereof has been completely decoded (Matsuzaki M et al., Nature. 2004 Apr. 8; 428 (6983): 653-7.), Cyanidioschyzon merolae can be easily genetically modified. Therefore, a transformant produced by genetically modifying Cyanidioschyzon merolae is a suitable example of the algae belonging to Cyanidiophyceae. In addition, not only Cyanidioschyzon merolae, but also the transformant of the algae belonging to Cyanidiophyceae may be used in the nutrient composition and the like according to the embodiment of the present invention as algae belonging to Cyanidiophyceae, as long as the transformant can be genetically modified. For example, as will be described later, although the algae belonging to Galdieria and the algae belonging to Cyanidium isolated from nature are diploid cells having a rigid cell wall, these can be made into haploid cells by the method of the present invention. Therefore, these algae have a haploid cell form and a diploid cell form. Cells in any form may be used as a cell population. Among those haploid algal cells, the cells that do not have a rigid cell wall just as Cyanidioschyzon merolae can be easily genetically modified. Accordingly, the transformant, which is obtained by genetically modifying haploid cells of the algae belonging to Galdieria or Cyanidium or cells having no rigid cell wall, is also a suitable example of the algae belonging to Cyanidiophyceae. More specifically, in addition to Cyanidioschyzon merolae, it is preferable to use haploids of Galdieria, haploids of Cyanidium, haploids of Cyanidioschyzon other than Cyanidioschyzon merolae, and haploids of Cyanidium. Furthermore, it is more preferable to use the cells which do not have a rigid cell wall among the above. Moreover, diploids belonging to Cyanidiophyceae which do not have a rigid cell wall are also preferable.

The transformant of the algae belonging to Cyanidiophyceae is not particularly limited, and examples thereof include a transformant having an increased intracellular content of at least one kind of nutrient. As the nutrient of which the intracellular content is to be increased, for example, at least one kind of nutrient selected from the group consisting of amino acids, vitamins, proteins, lipids, and dietary fiber is suitable. That is, for example, a transformant of the algae belonging to Cyanidiophyceae is preferable, which has a higher intracellular content of at least one kind of nutrient selected from the group consisting of amino acids, vitamins, proteins, lipids, and dietary fiber compared to a wild-type strain. In the present specification, "wild-type strain" means an original cell that is a target of transformation but has not yet been transformed.

Among the above nutrients, at least one kind of nutrient selected from the group consisting of amino acids and vitamins is preferable. Such transformant has a higher intracellular content of a specific nutrient compared to the wild-type strain. Therefore, by using the transformant, it is possible to prepare a nutrient composition, a nutritional supplement, and the like rich in the nutrient. The method for increasing the intracellular content of the nutrient is not particularly limited.

For example, the algae may be genetically modified such that the expression amount of an enzyme catalyzing any of the reactions in the synthesis pathway of the nutrient of interest is increased. As the genetic modification method for increasing the expression amount of the enzyme, known methods can be used without particular limitation. Examples of such a method include a method of introducing a gene encoding the enzyme (hereinafter, referred to as "enzyme gene"), a method of introducing a gene encoding a factor that promotes the expression of the enzyme gene, and a method of disrupting a gene encoding a factor that inhibits the expression of the enzyme gene, and the like. In a case where the enzyme gene is introduced into an algal cell, instead of a promoter sequence of the enzyme gene, a promoter of a gene expressed in large amounts in the algal cell into which the gene will be introduced may be used. The enzyme is not particularly limited as long as it is an enzyme that catalyzes any of the reactions in the synthesis pathway of the nutrient of interest. Examples of the enzyme include a synthase of the nutrient of interest, a synthase of a precursor of the nutrient of interest, and the like. "Precursor of the nutrient" may be any of the compounds that are generated at the stage before the nutrient is synthesized in the synthesis pathway of the nutrient of interest.

The method for increasing the intracellular content of a nutrient may be, for example, genetic modification for reducing the expression amount of a factor (hereinafter, referred to as "inhibitory factor") that inhibits any of the reactions in the synthesis pathway of the nutrient of interest. As the method for reducing the expression amount of the inhibitory factor, known methods can be used without particular limitation. Examples of such a method include a method of disrupting a gene encoding the inhibitory factor, a method of introducing a gene encoding a factor that inhibits the expression of a gene encoding the inhibitory factor, a method of disrupting a gene encoding a factor that promotes the expression of a gene encoding the inhibitory factor, and the like.

For example, glutamate decarboxylase is a synthase of γ-aminobutyric acid. Therefore, by genetically modifying the algae belonging to Cyanidiophyceae such that the expression amount of the glutamate decarboxylase is increased, it is possible to obtain a transformant having an increased intracellular content of γ-aminobutyric acid. Homogentisate phytyltransferase and tocopherol cyclase are enzymes that catalyze reactions in a vitamin E biosynthesis pathway. That is, the homogentisate phytyltransferase is an enzyme that synthesizes 2-methyl-6-phytylbenzoquinone, and the tocopherol cyclase is an enzyme that synthesizes γ-tocotrienol. Therefore, by genetically modifying the algae belonging to Cyanidiophyceae such that the expression amount of either or both of the enzyme genes described above, it is possible to obtain a transformant having an increased intracellular content of vitamin E. In order to increase the intracellular content of vitamin E, the expression amount of an enzyme that catalyzes another reaction in the vitamin E biosynthesis pathway may be increased. Similarly, for other nutrients, by increasing the expression amount of an enzyme that catalyzes any of the reactions in the biosynthetic pathway of the nutrient of interest (preferably, a rate-limiting reaction in the biosynthetic pathway), the intracellular content of the nutrient can be increased.

The sequence information of these synthetic enzyme genes can be obtained from a known sequence database such as GenBank. The sequence of the glutamate decarboxylase gene (CMF072C) of Cyanidioschyzon merolae is shown in SEQ ID NO: 3, and the amino acid sequence thereof is shown in SEQ ID NO: 4.

The sequence of the homogentisate phytyltransferase gene (CMN202C) of Cyanidioschyzon merolae is shown in SEQ ID NO: 5, and the amino acid sequence thereof is shown in SEQ ID NO: 6. The sequence of the tocopherol cyclase gene (CML326C) of Cyanidioschyzon merolae is shown in SEQ ID NO: 7, and the amino acid sequence thereof is shown in SEQ ID NO: 8.

For example, by introducing a synthetic enzyme gene (for example, the glutamate decarboxylase gene) of the aforementioned nutrient into the algae belonging to Cyanidiophyceae, it is possible to obtain a transformant having an increased intracellular content of the nutrient. The promoter used for the gene to be introduced may be the promoter of the synthetic enzyme gene or the promoter of another gene. In a case where the promoter of another gene is used, a promoter of a gene that is expressed in large amounts in the algal cell into which the gene is to be introduced is preferable. In the case of Cyanidioschyzon merolae, examples of such a promoter include a promoter of APCC (CMO250C) (for example, −600 to −1; "−1" indicates a nucleotide immediately before the start codon), and a promoter of CPCC (CMP166C), a promoter of Catalase (CMI050C), and the like.

The sequence information of these promoters can be obtained from a known sequence database such as GenBank. The promoter sequence of APCC of Cyanidioschyzon merolae is shown in SEQ ID NO: 9, the promoter sequence of CPCC (CMP166C) of Cyanidioschyzon merolae is shown in SEQ ID NO: 10, and the promoter sequence of Catalase (CMI050C) of Cyanidioschyzon merolae is shown in SEQ ID NO: 11.

Among the algae belonging to Cyanidiophyceae, Cyanidioschyzon merolae is algae capable of self-cloning (Fujiwara et al., PLoS One. 2013 Sep. 5; 8 (9): e73608). "Self-cloning" refers to a gene recombination technique only using, as nucleic acids to be introduced into a cell, (1) a nucleic acid of an organism that taxonomically belongs to the same species as the organism from which the cell is derived, and (2) a nucleic acid of an organism belonging to a species that exchanges nucleic acids with a taxonomic species, to which the organism as an origin of the cell belongs, under the natural conditions. The transformants prepared by self-cloning are excluded from the organisms to be subjected to genetic modification listed in the Cartagena Protocol. Therefore, the transformants can also be cultured outdoors. Accordingly, the transformant of the algae belonging to Cyanidiophyceae that is generated by self-cloning is suitable as algae used in the nutritional supplement of the present embodiment. Particularly, the transformant of Cyanidioschyzon merolae that is generated by self-cloning is preferable.

The method for performing self-cloning in Cyanidioschyzon merolae is not particularly limited, and examples thereof include a method using a URA5.3 gene (CMK046C) as a selection marker. Cyanidioschyzon merolae includes Cyanidioschyzon merolae M4 (Minoda et al., Plant Cell Physiol. 2004 June; 45 (6): 667-71.) which is a uracil auxotrophic mutant. Cyanidioschyzon merolae M4 has a mutation in the URA5.3 gene and cannot synthesize uracil. Accordingly, Cyanidioschyzon merolae M4 cannot grow in a uracil-free medium. Therefore, self-cloning can be performed using Cyanidioschyzon merolae M4 as a parent strain and using the URA5.3 gene of a wild-type strain as a selection marker. More specifically, an arbitrary gene set of Cyanidioschyzon merolae is linked to a URA5.3 gene set of a wild-type strain of Cyanidioschyzon merolae (for example, a 10D strain), and the resulting gene is introduced into Cyanidioschyzon merolae M4. Thereafter, by culturing the cells in a uracil-free medium, it is possible to obtain cells into which an arbitrary gene set has been introduced. "Gene set" described above means a set in which an arbitrary promoter, ORF of a target gene, and arbitrary 3'UTR are linked to each other. The 3'UTR is not particularly limited, and may be 3'UTR of a target gene or 3'UTR of another gene. As the 3'UTR, for example, 3'UTR of P-tubulin is frequently used. The selection marker is not limited to the URA5.3 gene, and may be a gene related to other types of auxotrophy.

In a case where the genetic modification is performed using the auxotrophy-related gene as a selection marker as described above, by knocking out the auxotrophy-related gene introduced into the algal cells, genetic modification can be performed again by using the same auxotrophy-related gene as a selection marker. That is, it is possible to perform multiple self-cloning. As the method for knocking out the auxotrophy-related gene introduced as a selection marker, known knockout techniques may be used without particular limitation. Examples of the knockout techniques include homologous recombination, a gene editing technique, and the like.

For example, as described above, in Cyanidioschyzon merolae, self-cloning can be performed using the URA5.3 gene (CMK46C) as a selection marker and Cyanidioschyzon merolae M4 as a parent strain. Untransformed cells cannot grow in a uracil-free medium. Therefore, after the transformation, by culturing the cells in a uracil-free medium, it is possible to select transformants. Furthermore, in a case where self-cloning is performed, by a known knockout technique such as homologous recombination, the URA5.3 gene is knocked out. For example, the introduced URA5.3 gene may be totally or partially deleted, or a point mutation may be introduced into the URA5.3 gene. By being cultured in a medium containing uracil and 5-fluoroorotic acid (5-FOA), the URA5.3 gene knockout strain can be selected. This is because in a strain that normally expresses the URA5.3 gene, 5-FOA is converted into toxic 5-fluorouracil by the gene product of the URA5.3 gene. In a case where the URA5.3 knockout strain obtained as above is used as a parent strain, self-cloning can be performed again by using the URA5.3 gene as a selection marker. By repeating the same operation, it is possible to perform self-cloning a desired number of times.

As the method for introducing an arbitrary nucleic acid into the algae belonging to Cyanidiophyceae, known methods can be used without particular limitation. Examples thereof include a polyethylene glycol method, a lipofection method, a microinjection method, a DEAE dextran method, a gene gun method, an electroporation method, a calcium phosphate method, and the like.

In a case where the algae belonging to Cyanidiophyceae are subjected to transformation, the nucleic acid to be introduced may be inserted into any of a nuclear genome, a chloroplast genome, and a mitochondrial genome. In a case where the nucleic acid to be introduced is inserted into the genome, the nucleic acid may be inserted into a specific position in the genome or randomly inserted into the genome.

As the method for inserting the nucleic acid to be introduced into a specific position in the genome, homologous recombination can be used. For example, for Cyanidioschyzon merolae, because the entire genome sequence thereof has been completely mapped (Matsuzaki M et al., Nature. 2004 Apr. 8; 428 (6983): 653-7.), the nucleic acid to be introduced can be inserted into a desired position on the genome. There is no particular limitation on the transgene insertion position in Cyanidioschyzon merolae. Examples of the insertion position include, for example, a region between CMD184C and CMD185C.

Specifically, as mutants of the algae belonging to Cyanidiophyceae, for example, the following (1) to (18) are preferable, but are not limited thereto.

(1) A transformant of the algae belonging to Cyanidiophyceae, in which the intracellular content of at least one kind of nutrient selected from the group consisting of y-aminobutyric acid and vitamin E is higher than that in a wild-type strain.

(2) The transformant of the algae belonging to Cyanidiophyceae according to (1), in which an expression amount of a glutamate decarboxylase gene is larger than in a wild-type strain.

(3) The transformant of the algae belonging to Cyanidiophyceae according to (2), into which a nucleic acid containing a glutamate decarboxylase gene has been introduced in an expressible form.

(4) The transformant of the algae belonging to Cyanidiophyceae according to (3), in which the nucleic acid contains a promoter that functions in the cells of the algae belonging to Cyanidiophyceae and a glutamate decarboxylase gene that is operably linked to the promoter.

(5) The transformant of the algae belonging to Cyanidiophyceae according to (1), in which an expression amount of at least one kind of gene selected from the group consisting of a homogentisate phytyltransferase gene and a tocopherol cyclase gene is larger than in a wild-type strain.

(6) The transformant of the algae belonging to Cyanidiophyceae according to (5), into which a nucleic acid including at least one kind of gene selected from the group consisting of a homogentisate phytyltransferase gene and a tocopherol cyclase gene has been introduced in an expressible form.

(7) The transformant of the algae belonging to Cyanidiophyceae according to (6), in which the nucleic acid includes a promoter that functions in the cells of the algae belonging to Cyanidiophyceae and a homogentisate phytyltransferase gene operably linked to the promoter.

(8) The transformant of the algae belonging to Cyanidiophyceae according to (6) or (7), in which the nucleic acid includes a promoter that functions in the cells of the algae belonging to Cyanidiophyceae and a tocopherol cyclase gene that is operably linked to the promoter.

(9) The transformant of the algae belonging to Cyanidiophyceae according to any one of (4), (7), and (8), in which the promoter is selected from the group consisting of an APCC promoter, a CPCC promoter, and a Catalase promoter.

(10) The transformant of the algae belonging to Cyanidiophyceae according to any one of (3), (4), and (6) to (9), in which the nucleic acid does not include a base sequence derived from a cell belonging to another taxonomic species.

(11) The transformant of the algae belonging to Cyanidiophyceae according to (10), in which the nucleic acid has been introduced into the cells by using an auxotrophy-related gene as a selection marker.

(12) The transformant of the algae belonging to Cyanidiophyceae according to (10), in which the nucleic acid has been introduced into a knockout cell of the auxotrophy-related gene by using the auxotrophy-related gene as a selection marker.

(13) The transformant of the algae belonging to Cyanidiophyceae according to any one of (1) to (12), in which the algae belonging to Cyanidiophyceae are algae belonging to Cyanidioschyzon.

(14) The transformant of the algae belonging to Cyanidiophyceae according to (13), in which the algae belonging to Cyanidiophyceae are Cyanidioschyzon merolae.

(15) The transformant of the algae belonging to Cyanidiophyceae according to (14), in which the auxotrophic gene is a URA5.3 gene.

(16) The transformant of the algae belonging to Cyanidiophyceae according to any one of (1) to (12), in which the algae belonging to Cyanidiophyceae are haploid cells of algae belonging to Galdieria.

(17) The transformant of the algae belonging to Cyanidiophyceae according to (16), in which the algae belonging to Galdieria are Galdieria sulphuraria or Galdieria partita.

(18) The transformant of the algae belonging to Cyanidiophyceae according to any one of (1) to (12), in which the algae belonging to Cyanidiophyceae are haploid cells of algae belonging to Cyanidium.

In the present specification, "operably linked" means that a first base sequence is disposed sufficiently close to a second base sequence and can exert an influence on the second base sequence or on a region which is under the control of the second base sequence. For example, "gene operably linked to a promoter" means that the gene is linked so as to be expressed under the control of the promoter. "Expressible form" refers to a form where a gene can be transcribed and translated in a cell into which the gene has been introduced.

[Extract of Algae Belonging to Cyanidiophyceae]

An extract of algae according to an embodiment of the present invention refers to a substance extracted from one kind of algae belonging to Cyanidiophyceae. However, the extract may contain a substance extracted from two or more kinds of algae belonging to Cyanidiophyceae or undisrupted cells of Cyanidiophyceae, and an extract and cells of algae that do not belong to Cyanidiophyceae.

In the nutrient composition and the like according to the embodiment of the present invention, the extract of the algae belonging to Cyanidiophyceae may be used instead of or together with the algae belonging to Cyanidiophyceae. The extract of the algae belonging to Cyanidiophyceae can also be rich in nutrients such as amino acids, vitamins, proteins, lipids, and dietary fiber, just as the algae belonging to Cyanidiophyceae. Therefore, the present invention also provides a nutrient composition, a nutritional supplement, a food, a feed or a pet food, a cosmetic, and the like using the extract of the algae belonging to Cyanidiophyceae.

In the present specification, "extract of the algae belonging to Cyanidiophyceae" refers to a substance obtained by extracting intracellular components by performing a physical treatment or a chemical treatment on the cells of the algae belonging to Cyanidiophyceae. For example, the extract of the algae belonging to Cyanidiophyceae may be a cell disruption product obtained by disrupting the cells of the algae belonging to Cyanidiophyceae by a physical treatment or a chemical treatment. In addition, the extract of algae belonging to Cyanidiophyceae may be a substance obtained by concentrating the cell disruption product, a substance obtained by removing solid contents from the cell disruption product, or a substance obtained by removing some components from the cell disruption product.

The method of the physical treatment or the chemical treatment for the cells is not particularly limited, and the methods generally used for cell disruption can be used. Examples of the physical treatment include cell disruption performed by means of glass beads, a mortar, an ultrasonic treatment, a French press, a homogenizer, and the like.

Examples of the chemical treatment include a neutralization treatment, a hypotonic treatment, a freeze-thaw treatment, a dry and swelling treatment, and the like. More specifically, examples thereof include the cell rupturing treatments (A) to (C) described above.

In a case where the cell disruption product is concentrated, the concentration method is not particularly limited, and a generally used concentration method may be used. Examples of the concentration method for the cell disruption product include drying, freeze-drying, drying under reduced pressure, and the like.

In a case where solid contents are removed from the cell disruption product, the solid content-removing method is not particularly limited, and it is possible to use a method that is generally used for removing solid contents and the like.

Examples of the solid content-removing method include filtration, centrifugation, and the like.

In a case where some components are separated from the cell disruption product, the separation method is not particularly limited, and it is possible to use a method generally used for separation, purification, and the like of biochemical substances. Examples of the separation method include salting out, dialysis, solvent extraction, adsorption, column chromatography, ion exchange chromatography, and the like. Each of these methods may be used singly. Alternatively, two or more kinds of treatments may be used in combination. Here, a substance purified into a single component is excluded from "extract of the algae belonging to Cyanidiophyceae". The extract of the algae belonging to Cyanidiophyceae preferably contains 10 or more kinds of cell components of the algae belonging to Cyanidiophyceae, more preferably contains 15 or more kinds of the cell components described above, and even more preferably contains 20 or more kinds of the cell components described above. The extract of the algae belonging to Cyanidiophyceae preferably contains a nutrient selected from the group consisting of amino acids, vitamins, proteins, lipids, and dietary fiber, and more preferably contains a nutrient selected from the group consisting of amino acids and vitamins. Specific examples of the amino acids include isoleucine, leucine, lysine, methionine, cystine, phenylalanine, tyrosine, threonine, tryptophan, valine, arginine, histidine, alanine, aspartic acid, glutamic acid, glycine, proline, serine, $\gamma$-aminobutyric acid, and the like. Specific examples of the vitamins include vitamin A, $\beta$-carotene, vitamin $B_1$, vitamin $B_2$, vitamin $B_6$, vitamin C, vitamin E, vitamin $K_1$, vitamin $K_2$, niacin, inositol, folic acid, biotin, and the like.

[Alga Having a Diploid Cell Form and a Haploid Cell Form]

In one embodiment, the present invention provides an alga which belongs to Cyanidiophyceae and having a diploid cell form and a haploid cell form.

One of the characteristics of the alga of the present embodiment is that the alga belong to Cyanidiophyceae and having diploid cell form and a haploid cell form. Hitherto, it has been known that among the algae belonging to Cyanidiophyceae, the algae belonging to Cyanidioschyzon include haploid algae. However, among the algae belonging to Cyanidiophyceae, no algae have been known so far which have both the diploid cell form and haploid cell form. That is, from nature, Cyanidioschyzon merolae belonging to Cyanidioschyzon which belongs to Cyanidiophyceae has been collected only in the form of haploids. Furthermore, from nature, Galdieria and Cyanidium, which are other algae belonging to Cyanidiophyceae, have been collected only in the form of diploids. The present invention provides algae, which are haploid cells that are created from diploid cells of the algae belonging to Cyanidiophyceae, and algae which are diploid cells generated from two or more haploid cells. In the present specification, the algae described above will be expressed using "having both a diploid cell form and a haploid cell form".

The algae of the present embodiment having both a diploid cell form and a haploid cell form.

In the algae of the present embodiment, the haploid cells are generated by the meiosis of the diploid cells. It is considered that by the mating of two haploid cells, diploid cells may be generated. Therefore, in the algae of the present embodiment, by mating haploid cells having desired traits, diploid cells having the traits of the cells can be prepared.

For example, in a case where the haploid cells are used, it is easier to prepare a transformant by using a gene recombination technique than in a case where the diploid cells are used. Therefore, a method is considered in which a plurality of transformants having any traits are prepared using the haploid cells, and the transformants having any traits are crossing so as to prepare diploids having all the traits of the transformants.

The algae of the present embodiment can grow in a cell population consisting only of haploid cells.

The algae of the present embodiment can grow in a cell population consisting only of diploid cells.

Furthermore, as is evident from Examples which will be described later, it is possible to create haploid cells from diploid cells and to create diploid cells from two or more kinds of haploid cells. In addition, in a case where haploid cells are created from diploid cells or in a case where diploid cells are created from haploid cells, sometimes the haploid cells and the diploid cells are mixed together.

Whether certain algae are diploids or haploids can be determined by the method exemplified in "[Alga belonging to Cyanidiophyceae]" described above.

Furthermore, whether certain algae having both the diploid cell form and a haploid cell form can be determined, for example, by the following method. First, the diploid cells are cultured until they reach a stationary phase, and whether cells in the form different from the diploid appear is checked when culturing is continued in the stationary phase. When the cells in the form different from the diploid appear, the cells are collected, and whether they are haploid cells is checked. In a case where the cells are found to be haploid cells as a result, it is possible to determine that the algae having both a diploid cell form and a haploid cell form.

In the algae of the present embodiment, it is preferable that at least the cells in either of the cell forms do not have a rigid cell wall. The cells having no rigid cell wall can be disrupted by a relatively mild treatment such as a neutralization treatment, a hypotonic treatment, a freeze-thaw treatment, or the like. Whether or not the algae have a rigid cell wall can be determined by the method described in "[Alga belonging to Cyanidiophyceae]" described above.

In the algae of the present embodiment, it is preferable that at least either the diploid cells or the haploid cells do not have a rigid cell wall. It is more preferable that the haploid cells do not have a rigid cell wall. That is, it is preferable that the haploid cells are ruptured by any of the cell rupturing treatments (A) to (C) described above.

In a case where a cell does not have a rigid cell wall, generally, the cell wall is not observed by the observation with an optical microscope (for example, at a magnification of 600×). In the algae of the present embodiment, usually, the diploid cells have a rigid cell wall while the haploid cells do not have a rigid cell wall.

As shown in Examples which will be described later, the algae of the present embodiment are rich in nutrients such as amino acids, vitamins, proteins, lipids, and dietary fiber. Particularly, it has been confirmed that the algae belonging to Cyanidiophyceae contain amino acids and vitamins at a higher concentration compared to the conventionally used algae (*Chlorella, Euglena*, and *Spirulina*). Therefore, the algae of the present embodiment can be used for a method for producing a nutritional supplement or a nutrient which will be described later.

Examples of the amino acids contained in the algae of the present embodiment include isoleucine, leucine, lysine, methionine, cystine, phenylalanine, tyrosine, threonine, tryptophan, valine, arginine, histidine, alanine, aspartic acid, glutamic acid, glycine, glycine, proline, serine, 7-aminobutyric acid, and the like. One of the characteristics of the algae of the present embodiment is that the total amino acid content thereof is higher than that of the conventionally used algae. Furthermore, the content of each of the amino acids in the algae of the present embodiment tends to be high in general.

For example, the total amino acid content in the algae of the present embodiment is preferably equal to or greater than 50 g/100 g based on dry weight. The range of the total amino acid content is, for example, 50 g to 70 g/100 g based on dry weight. In the present specification, "total amino acid content" means a value obtained by adding up the contents of isoleucine, leucine, lysine, methionine, cystine, phenylalanine, tyrosine, threonine, tryptophan, valine, arginine, histidine, alanine, aspartic acid, glutamic acid, glycine, proline, and serine.

The content of isoleucine in the algae of the present embodiment is preferably equal to or greater than 1.5 g/100 g based on dry weight. The range of the content of isoleucine is, for example, 1.5 g to 5 g/100 g based on dry weight.

The content of leucine in the algae of the present embodiment is preferably equal to or greater than 4.5 g/100 g based on dry weight. The range of the content of isoleucine is, for example, 4.5 g to 8 g/100 g based on dry weight.

The content of lysine in the algae of the present embodiment is preferably equal to or greater than 2.5 g/100 g based on dry weight. The range of the content of lysine is, for example, 2.5 g to 6 g/100 g based on dry weight.

The content of methionine in the algae of the present embodiment is preferably equal to or greater than 0.5 g/100 g based on dry weight. The range of the content of methionine is, for example, 0.5 g to 4 g/100 g based on dry weight.

The content of cystine in the algae of the present embodiment is preferably equal to or greater than 0.5 g/100 g based on dry weight. The range of the content of cystine is, for example, 0.5 g to 3 g/100 g based on dry weight.

The content of phenylalanine in the algae of the present embodiment is preferably equal to or greater than 1.5 g/100 g based on dry weight. The range of the content of phenylalanine is, for example, 1.5 g to 5 g/100 g based on dry weight.

The content of tyrosine in the algae of the present embodiment is preferably equal to or greater than 2.0 g/100 g based on dry weight. The range of the content of tyrosine is, for example, 2.0 g to 5 g/100 g based on dry weight.

The content of threonine in the algae of the present embodiment is preferably equal to or greater than 2.0 g/100 g based on dry weight. The range of the content of threonine is, for example, 2.0 g to 5 g/100 g based on dry weight.

The content of tryptophan in the algae of the present embodiment is preferably equal to or greater than 0.5 g/100 g based on dry weight. The range of the content of tryptophan is, for example, 0.5 g to 3 g/100 g based on dry weight.

The content of valine in the algae of the present embodiment is preferably equal to or greater than 2.5 g/100 g based on dry weight. The range of the content of valine is, for example, 2.5 g to 6 g/100 g based on dry weight.

The content of arginine in the algae of the present embodiment is preferably equal to or greater than 4.5 g/100 g based on dry weight. The range of the content of phenylalanine is, for example, 4.5 g to 8 g/100 g based on dry weight.

The content of histidine in the algae of the present embodiment is preferably equal to or greater than 0.5 g/100 g based on dry weight. The range of the content of histidine is, for example, 0.5 g to 3 g/100 g based on dry weight.

The content of alanine in the algae of the present embodiment is preferably equal to or greater than 3.5 g/100 g based on dry weight. The range of the content of alanine is, for example, 3.5 g to 7 g/100 g based on dry weight.

The content of aspartic acid in the algae of the present embodiment is preferably equal to or greater than 4.5 g/100 g based on dry weight. The range of the content of aspartic acid is, for example, 4.5 g to 8 g/100 g based on dry weight.

The content of glutamic acid in the algae of present embodiment is preferably equal to or greater than 5.5 g/100 g based on dry weight. The range of the content of glutamic acid is, for example, 5.5 g to 9 g/100 g based on dry weight.

The content of glycine in the algae of the present embodiment is preferably equal to or greater than 2.0 g/100 g based on dry weight. The range of the content of glycine is, for example, 2.0 g to 5.5 g/100 g based on dry weight.

The content of proline in the algae of the present embodiment is preferably equal to or greater than 1.5 g/100 g based on dry weight. The range of the content of proline is, for example, 1.5 g to 5 g/100 g based on dry weight.

The content of serine in the algae of present embodiment is preferably equal to or greater than 2.0 g/100 g based on dry weight. The range of the content of serine is, for example, 2.0 g to 5 g/100 g based on dry weight.

The content of $\gamma$-aminobutyric acid in the algae of the present embodiment is preferably equal to or greater than 0.05 g/100 g based on dry weight. The range of the content of $\gamma$-aminobutyric acid is, for example, 0.05 g to 0.3 g/100 g based on dry weight.

Examples of the vitamins contained in the algae of the present embodiment include vitamin A, $\beta$-carotene, vitamin C, vitamin E, vitamin $K_1$, vitamin $K_2$, folic acid, and the like.

One of the characteristics of the algae of the present embodiment is that the content of $\beta$-carotene, vitamin C, vitamin E, vitamin $K_1$, vitamin $K_2$, and folic acid is particularly higher in the algae of the present embodiment than in the conventionally used algae.

The content of vitamin A in the algae of the present embodiment is preferably equal to or greater than 8 mg/100 g based on dry weight. The range of the content of vitamin A is, for example, 8 mg to 20 mg/100 g based on dry weight.

The content of $\beta$-carotene in the algae of the present embodiment is preferably equal to or greater than 100 mg/100 g based on dry weight. The range of the content of $\beta$-carotene is, for example, 100 mg to 200 mg/100 g based on dry weight.

The content of vitamin C in the algae of the present embodiment is preferably equal to or greater than 20 mg/100 g based on dry weight. The range of the content of vitamin C is, for example, 20 mg to 50 mg/100 g based on dry weight.

The content of vitamin E in the algae of the present embodiment is preferably equal to or greater than 80 mg/100 g based on dry weight. The range of the content of vitamin E is, for example, 80 mg to 150 mg/100 g dry weight.

The content of vitamin $K_1$ in the algae of the present embodiment is preferably equal to or greater than 4,000 g/100 g based on dry weight. The range of the content of vitamin $K_1$ is, for example, 4,000 g to 8,000 g/100 g based on dry weight.

The content of vitamin $K_2$ in the algae of the present embodiment is preferably equal to or greater than 1,000 g/100 g based on dry weight. The range of the content of vitamin $K_2$ is, for example, 1,000 g to 3,000 g/100 g based on dry weight.

The content of folic acid in the algae of the present embodiment is preferably equal to or greater than 1,500 g/100 g based on dry weight. The range of the content of folic acid is, for example, 1,500 g to 4,000 g/100 g based on dry weight.

The algae of the present embodiment can be cultured using a medium for culturing microalgae. The culturing can be performed in the same manner as in the method described above in "[Alga belonging to Cyanidiophyceae]".

The algae of the present embodiment can also be cultured in a medium using acidic hot spring drainage. "Acidic hot spring drainage" means acidic drainage discharged from hot spring facilities. The acidic hot spring drainage is not particularly limited, and the pH thereof is preferably 1.0 to 4.0 and more preferably 1.0 to 3.0. "Medium using acidic hot spring drainage" means a medium prepared by adding a nitrogen source, a phosphorus source, trace elements, and the like to acidic hot spring drainage. As the medium using acidic hot spring drainage, a medium obtained by adding a nitrogen source to acidic hot spring drainage is preferable, and a medium obtained by adding a nitrogen source and a phosphorus source to acidic hot spring drainage is more preferable (for example, see Hirooka S and Miyagishima S. Y. (2016) Cultivation of Acidophilic Algae *Galdieria sulphuraria* and *Pseudochlorella* sp. YKT1 in Media Derived from Acidic Hot Springs. Front Microbiol. December 20; 7: 2022.). Examples of the nitrogen source include ammonium salts (such as ammonium sulfate), urea, nitrates (such as sodium nitrate), and the like. Among these, ammonium salts and urea are preferable, and ammonium salts are more preferable. The amount of the nitrogen source to be added is, for example, 1 to 50 mM as the amount of nitrogen to be added. The amount of the nitrogen source to be added is preferably 5 to 40 mM and more preferably 10 to 30 mM as the amount of nitrogen to be added. Examples of the phosphorus source include phosphates (such as potassium dihydrogen phosphate). The amount of the phosphorus source to be added is, for example, 0.1 to 10 mM as the amount of phosphorus to be added. The amount of the phosphorus source to be added is preferably 0.5 to 5 mM and more preferably 1 to 3 mM as the amount of phosphorus to be added. The algae of the present embodiment can be cultured in a medium using acidic hot spring drainage. Therefore, the algae of the present embodiment make it possible to effectively use acidic hot spring drainage and can be cultured at low costs.

In a case where the algae of the present embodiment are algae belonging to Galdieria, as the aforementioned nitrogen source, an ammonium salt or urea is preferable, and an ammonium salt is more preferable. In a case where the algae of the present embodiment are algae belonging to Cyanidium, as the aforementioned nitrogen source, an ammonium salt or a nitrate is preferable, and an ammonium salt is more preferable.

(YFU3 Strain and HKN1 Strain)

Specific examples of the algae of the present embodiment include a Cyanidium sp. YFU3 (FERM BP-22334) (hereinafter, referred to as "YFU3 strain"), a Cyanidium sp. HKN1 (FERM BP-22333) (hereinafter referred to as "HKN1 strain"), and allied species, mutants, and progenies of these.

Both the YFU3 strain and the HKN1 strain have a diploid cell form and a haploid cell form. Hereinafter, when the YFU3 strain is described by distinguishing between diploid cells and haploid cells, the diploid cells will be described as "YFU3 strain (diploid)", and the haploid cells will be described as "YFU3 strain (haploid)". Likewise, when HKN1 strain is described by distinguishing between diploid cells and haploid cells, the diploid cells will be described as "HKN1 strain (diploid)", and the haploid cells will be described as "HKN1 strain (haploid)". When the strains are simply referred to as "YFU3 strain" or "HKN1 strain", each of the strains includes both the diploid cells and the haploid cells.

The YFU3 strain (haploid) is unicellular red algae isolated from hot acidic water of a hot spring in Yufu-shi, Oita prefecture, Japan. The YFU3 strain was deposited in the Patent Microorganism Depositary Center of National Institute of Technology and Evaluation (2-5-8 Kazusa Kamatari, Kisarazu-shi, Chiba prefecture, Japan) on Jun. 28, 2017 under the accession No. FERM P-22334, and transferred to the International Depositary on May 23, 2018 under the accession No. FERM BP-22334.

The HKN1 strain is unicellular red algae isolated from hot acidic water of a hot spring in Hakone-machi, Ashiga-rashimo-gun, Kanagawa prefecture, Japan. The HKN1 strain (haploid) was deposited in the Patent Microorganism Depositary Center of National Institute of Technology and Evaluation on Jun. 28, 2017 under the accession No. FERM P-22333, and transferred to the International Depositary on May 23, 2018 under the accession No. FERM BP-22333.

Both the YFU3 strain and the HKN1 strain have a blue pigment, phycocyanin, in addition to chlorophyll a. Therefore, these strains appear blue-green. Both the YFU3 strain and the HKN1 strain grow suitably in a high-temperature acidic environment, at an optimum temperature of about 42° C. and an optimum pH of around 2.

Both the YFU3 strain (diploid) and the HKN1 strain (diploid) have a cell size of about 4 μm. In addition, both the YFU3 strain (haploid) and the HKN1 strain (haploid) have a cell size of about 2 m. Furthermore, both the YFU3 strain (diploid) and the HKN1 strain (diploid) have a rigid cell wall. That is, these strains do not undergo cell rupture under the condition of pH 7. In contrast, neither the YFU3 strain (haploid) nor the HKN1 strain (haploid) has a rigid cell wall. That is, these strains undergo cell rupture under the condition of pH 7.

The cells of the YFU3 strain (haploid) and the HKN1 strain (haploid) are similar to the cells of Cyanidioschyzon merolae (see FIG. 8). Among the algae belonging to Cyanidiophyceae, Cyanidioschyzon merolae is the only known species of haploid algae having no rigid cell wall. In the present specification, the cells similar to the cells of Cyanidioschyzon merolae will be described as "Cyanidioschyzon merolae-like cells" in some cases.

When the YFU3 strain (diploid) is cultured until the strain enters the stationary phase, and the culturing is continued in the stationary phase, several YFU3 strains (diploid) undergo meiosis. As a result, from one cell of the YFU3 strain (diploid), four cells of the YFU3 strain (haploid) are generated. Likewise, when the HKN1 strain (diploid) is cultured until the strain enters the stationary phase, and the culturing is continued in the stationary phase, several HKN1 strains (diploid) undergo meiosis. As a result, form one cell of the HKN1 strain (diploid), four cells of HKN1 strain (haploid) are generated. Through two-cell division, both the YFU3 strain (haploid) and the HKN1 strain (haploid) can grow while maintaining the form of haploid cells.

As the algae of the present embodiment, for example, in addition to the YFU3 strain and the HKN1 strain, algae, which are allied species of the YFU3 strain or the HKN1 strain and having a diploid cell form and a haploid cell form, are suitable. Examples of the algae as allied species of the YFU3 strain and the HKN1 strain include algae in which the base sequence of the rbcL gene shares identity equal to or higher than 90% with the base sequence of the rbcL gene of the YFU3 strain or the HKN1 strain. The base sequence of the rbcL gene of the YFU3 strain is shown in SEQ ID NO: 1. The base sequence of the rbcL gene of the HKN1 strain is shown in SEQ ID NO: 2. Therefore, the algae, in which the base sequence of the rbcL gene shares identity equal to or higher than 90% with the base sequence shown in SEQ ID NO: 1 or 2, are also a suitable example of the algae of the present embodiment. The identity between the base sequence of the rbcL gene of the algae and the base sequence shown in SEQ ID NO: 1 or 2 is preferably equal to or higher than 95%, more preferably equal to or higher than 97%, even more preferably equal to or higher than 98%, and particularly preferably equal to or higher than 99%.

The base sequence of the rbcL gene of algae can be obtained by a known method. For example, by extracting DNA from algal cells of interest by a known method, amplifying DNA fragments of the rbcL gene by PCR or the like, and analyzing the base sequence of the amplified DNA fragments by using a DNA sequencer, the base sequence of the rbcL gene of the algae of interest can be obtained. Examples of primers for amplifying the rbcL gene include the primers used in Examples of the present specification and the like.

As the algae of the present embodiment, for example, algae, which are a mutant of the YFU3 strain or the HKN1 strain and have a diploid cell form and a haploid cell form, are also suitable. In the present specification, "mutant" means an algal strain generated when spontaneous or induced mutation occurs in the genome of the original algal strain (including a nuclear genome, a chloroplast genome, and a mitochondrial genome; the same is true of the following description). The technique for inducing mutation in the genome is not particularly limited, and examples thereof include ultraviolet irradiation, radiation irradiation, a chemical treatment using nitrous acid; genetic engineering techniques such as gene introduction and genome editing, and the like. In the present specification, "mutant of the YFU3 strain" refers to an algal strain which is generated by the mutation of the genome of the YFU3 strain and has a diploid cell form and a haploid cell form. Furthermore, "mutant of the HKN1 strain" refers to an algal strain which is generated by the mutation of the genome of the HKN1 strain and has a diploid cell form and a haploid cell form.

In the mutant of the YFU3 strain, the proportion of mutations in the whole genome of the YFU3 strain is preferably equal to or lower than 10%, more preferably equal to or lower than 5%, even more preferably equal to or lower than 3%, and particularly preferably equal to or lower than 2% or 1%.

In the mutant of the HKN1 strain, the proportion of mutations in the whole genome of the HKN1 strain is preferably equal to or lower than 10%, more preferably equal to or lower than 5%, even more preferably equal to or lower than 3%, and particularly preferably equal to or lower than 2% or 1%.

In the above description, the proportion of mutations in the whole genome is calculated by comparing the whole genomes of the diploid cells or comparing the whole genomes of the haploid cells.

Among the above, as the allied species or the mutant of the YFU3 strain or the HKN1 strain, those having a nutritional composition similar to the nutritional composition of the YFU3 strain or the HNK1 strain are preferable.

For example, one of the characteristics of the YFU3 strain and the HKN1 strain is that these strains are rich in amino acids and vitamins. Therefore, it is preferable that the content of amino acids or vitamins in the allied species or the mutant is similar to those in the YFU3 strain and the HKN1 strain. Examples of the content of amino acids and vitamins include the contents exemplified above.

Specific examples of the mutant of the YFU3 strain or the HKN1 strain include transformants obtained by genetic modification using genetic engineering techniques. The genetic modification may be performed on the diploid cells or the haploid cells. However, it is easier to genetically modify the haploid cells. The type of genetic modification is not particularly limited, and any type of modification may be adopted.

Examples of the transformant of the YFU3 strain or the HKN1 strain include a transformant having an increased intracellular content of at least one kind of nutrient. As the nutrient of which the intracellular content is to be increased, for example, at least one kind of nutrient selected from the group consisting of amino acids, vitamins, proteins, lipids, and dietary fiber is suitable. That is, a transformant of the YFU3 strain or the HKN1 strain is suitable, in which the intracellular content of at least one kind of nutrient selected from the group consisting of amino acids, vitamins, proteins, lipids, and dietary fiber is higher than that in a wild-type strain.

Among the above nutrients, at least one kind of nutrient selected from the group consisting of amino acids and vitamins is preferable. Such a transformant has a higher intracellular amount of a specific nutrient compared to a wild-type strain. Therefore, by using this transformant, it is possible to prepare a nutritional supplement rich in the nutrient.

The method for increasing the intracellular content of a nutrient is not particularly limited, and any method can be used. Examples thereof include a method similar to the method exemplified in "[Alga belonging to Cyanidiophyceae]" described above. For example, by modifying the YFU3 strain or the HKN1 strain such that the expression amount of any enzyme gene involved in the synthesis of nutrients such as glutamate decarboxylase, homogentisate phytyltransferase, and tocopherol cyclase is increased, the intracellular content of any nutrient can be increased.

The sequence information of these synthetic enzyme genes can be obtained by cloning the gene of interest and analyzing the sequence of the cloned gene of interest by a known method.

For example, primers may be designed based on the sequence information of known homologous genes of the algae belonging to Cyanidiophyceae, and amplified fragments of the gene of interest may be obtained by PCR or the like by using the genome of the YFU3 strain or the HKN1 strain as a template. Alternatively, a probe may be designed based on the sequence information of a known homologous gene of the algae belonging to Cyanidiophyceae, and a cDNA library of the YFU3 strain or the HKN1 strain may be screened out.

Furthermore, as a transgene, a gene of an organism of another species may be used as long as the gene functions in the transfected cell. For example, a known gene of the algae belonging to Cyanidiophyceae may be used. The sequence information of a known gene can be obtained from a known sequence database such as GenBank. For example, it is possible to use a glutamate decarboxylase gene (CMF072C), a homogentisate phytyltransferase gene (CMN202C), a tocopherol cyclase gene (CML326C), of Cyanidioschyzon merolae, and the like.

For example, by introducing a synthetic enzyme gene (for example, a glutamate decarboxylase gene) of the nutrient described above into the YFU3 strain or the HKN1 strain, it is possible to obtain a transformant having an increased intracellular content of the nutrient. The promoter used for the gene to be introduced may be the promoter of the synthetic enzyme gene or the promoter of another gene. In a case where the promoter of another gene is used, a promoter of a gene that is expressed in large amounts in the algal cell into which the gene is to be introduced is preferable. Examples of such a promoter include an APCC (CMO250C) promoter, a CPCC (CMP166C) promoter, a Catalase (CMI050C) promoter, and the like. The promoter may be derived from an organism of the same species as the cell to be transfected, or may be derived from an organism of another species, as long as the promotor functions in the cell to be transfected.

In a case where a promoter of a known gene is used, the sequence information thereof can be obtained from a known sequence database such as GenBank.

The transformant of the YFU3 strain or the HKN1 strain can be prepared by the introduction of any nucleic acid. However, the transformant is more preferably prepared by self-cloning. For example, among the algae belonging to Cyanidiophyceae, for Cyanidioschyzon merolae, a self-cloning method has been established (Fujiwara et al., PLoS One. 2013 Sep. 5; 8 (9): e73608). Therefore, self-cloning can also be performed on the YFU3 strain or the HKN1 strain by the same method as the method used for Cyanidioschyzon merolae.

The self-cloning method is not particularly limited, and examples thereof include a method using an auxotrophic mutant. For example, for Cyanidioschyzon merolae, a method using the URA5.3 gene (CMK046C) as a selection marker has been suggested (see "[Algae belonging to Cyanidiophyceae]" described above).

For the YFU3 strain and the HKN1 strain, by knocking out an auxotrophy-related gene by a known gene knockout technique or the like so as to prepare an auxotrophic mutant, self-cloning can be performed using the gene to be knocked out as a selection marker. As the knockout technique, a known method may be used without particular limitation. Examples of the knockout technique include homologous recombination, a gene editing technique, and the like. The gene to be knocked out is not particularly limited as long as the auxotrophy is changed by the knockout of the gene. Examples of the gene to be knocked out include orotidine-5'-decarboxylase and the like.

In addition, in a case where genetic modification is performed using the auxotrophy-related gene as a selection marker as described above, by knocking out the auxotrophy-related gene introduced into algal cells, the genetic modification can be performed again by using the same auxotrophy-related gene as a selection marker. That is, it is possible to perform multiple self-cloning. As the method for knocking out the auxotrophy-related gene introduced as a selection marker, known knockout techniques may be used without particular limitation. Examples of the knockout technique include homologous recombination, a gene editing technique, and the like.

For example, as described above, in Cyanidioschyzon merolae, self-cloning can be performed using the URA5.3 gene (CMK046C) as a selection marker and Cyanidioschyzon merolae M4 as a parent strain. In a case where a URA5.3 gene knockout strains are prepared in the YFU3 strain and the HKN1 strain, the knockout strains cannot grow in a uracil-free medium. In a case where the aforementioned strains are used as parent strains, the URA5.3 gene is introduced into the strains so as to cause transformation, and the transformed cells are cultured in uracil-free medium, transformants can be selected. Furthermore, in a case where self-cloning is performed, the URA5.3 gene is knocked out again by a known knockout technique such as homologous recombination. By culturing the cells in a medium containing uracil and 5-fluoroorotic acid, the re-knockout strain of the URA5.3 gene can be selected. This is because in a strain that normally expresses the URA5.3 gene, 5-FOA is converted into toxic 5-fluorouracil by the gene product of the URA5.3 gene. In a case where the re-knockout strain of URA5.3 obtained as above is used as a parent strain, self-cloning can be performed again by using the URA5.3 gene as a selection marker. By repeating the same operation, it is possible to perform self-cloning a desired number of times. By the knockout of the URA5.3 gene, the URA5.3 gene may be totally or partially deleted, or a point mutation may be introduced into the URA5.3 gene.

The method for introducing an arbitrary nucleic acid into the YFU3 strain or the HKN1 strain is not particularly limited, and a known method can be used. Examples thereof include a polyethylene glycol method, a lipofection method, a microinjection method, a DEAE dextran method, a gene gun method, an electroporation method, a calcium phosphate method, and the like.

In a case where the YFU3 strain or the HKN1 strain is transformed, the nucleic acid to be introduced may be inserted into any of a nuclear genome, a chloroplast genome, and a mitochondrial genome. In a case where the nucleic acid to be introduced is inserted into the genome, the nucleic acid may be inserted into a specific position in the genome or randomly inserted into the genome. As the method for inserting the nucleic acid to be introduced into a specific position in the genome, homologous recombination can be used.

An example of the transformation method for the YFU3 strain or the HKN1 strain will be described below, but the present invention is not limited thereto.

First, the YFU3 strain or the HKN1 strain is diluted with an appropriate medium such as MA2U medium (see Example 7) such that the concentration thereof becomes appropriate. Then, the cells are cultured for about for about 40 to 80 hours with aeration under appropriate culture conditions (for example, light-dark cycle: 12L:12D, light: 50 mol/m$^2$s, temperature: 42° C.). Thereafter, Tween-20 is added to the culture solution such that the final concentration becomes 0.002%, and then the cells are collected by centrifugation and suspended in an appropriate medium such as MA2U medium. The culture solution is dissolved in 450 μL of MA2U medium containing PEG4000 (95° C., 10 minutes), thereby preparing a 60% (w/v) PEG4000 solution. Subsequently, the PEG 4000 solution was kept at 42° C. on a heat block until used.

The cell suspension of the YFU3 strain or the HKN1 strain is added to a mixture for transformation containing a vector for transformation including an appropriate selection marker and polyethylene glycol (such as PEG4000), and the mixture is stirred. The cells are moved to an appropriate medium such as MA2U medium and cultured in a static state for about 40 to 60 hours under appropriate culture conditions (for example, continuous light: 20 mol/m$^2$s, temperature: 42° C.). Then, the cells are collected by centrifugation, and suspended in an appropriate medium such as Tsukahara mineral spring medium (Hirooka et al. 2016 Front in Microbiology) or modified MA medium (see Example 7). The cell suspension is added to a selective medium compatible with the used selection marker (for example, a medium obtained by adding a specific substance to the Tsukahara mineral spring medium, the modified MA medium, or the like, or a medium obtained by removing a specific substance from the medium described above), and the cells are cultured in a static state for about 5 to 10 days under appropriate culture conditions (for example, continuous light: 20 mol/m$^2$s, temperature: 42° C., 3% CO$_2$). The culture solution of a green portion, which has become darker, is added to the newly collected selective medium, the cells are further cultured in a static state for about 5 to 10 days, and transformants are selected. For example, under an inverted microscope, the transformants are isolated one by one by using a Pasteur pipette with a sharp tip, and cultured in a static state in an appropriate medium such as the Tsukahara mineral spring medium or the modified MA medium. In this way, the transformants can be obtained.

In the above section, an example of transformation by a polyethylene glycol method was described. However, other transformation methods such as a lipofection method, a microinjection method, a DEAE dextran method, a gene gun method, an electroporation method, and a calcium phosphate method may also be used.

Specific examples of strains preferred as the mutants of the YFU3 strain or the HKN1 strain include, but are not limited to, the following (1) to (18).

(1) A transformant of the YFU3 strain or the HKN1 strain, which has a higher intracellular content of at least one kind of nutrient selected from the group consisting of γ-aminobutyric acid and vitamin E as compared to a wild-type strain.

(2) The transformant of the YFU3 strain or the HKN1 strain according to (1), in which an expression amount of a glutamate decarboxylase gene is larger than in a wild-type strain.

(3) The transformant of the YFU3 strain or the HKN1 strain according to (2), into which a nucleic acid containing the glutamate decarboxylase gene has been introduced in an expressible form.

(4) The transformant of the YFU3 strain or the HKN1 strain according to (3), in which the nucleic acid contains a promoter that functions in cells of algae belonging to Cyanidiophyceae and a glutamate decarboxylase gene operably linked to the promoter.

(5) The transformant of the YFU3 strain or the HKN1 strain according to (1), in which an expression amount of at least one kind of gene selected from the group consisting of a homogentisate phytyltransferase gene and a tocopherol cyclase gene is larger than in the wild-type strain.

(6) The transformant of the YFU3 strain or the HKN1 strain according to (5), into which a nucleic acid containing at least one kind of gene selected from the group consisting of a homogentisate phytyltransferase gene and a tocopherol cyclase gene has been introduced in an expressible form.

(7) The transformant of the YFU3 strain or the HKN1 strain according to (6), in which the nucleic acid contains a promoter that functions in cells of algae belonging to Cyanidiophyceae and a homogentisate phytyltransferase gene operably linked to the promoter.

(8) The transformant of the YFU3 strain or the HKN1 strain according to (6) or (7), in which the nucleic acid contains a promoter that functions in cells of algae belonging to Cyanidiophyceae and a tocopherol cyclase gene operably linked to the promoter.

(9) The transformant of the YFU3 strain or the HKN1 strain according to any one of (4), (7), and (8), in which the promoter is selected from the group consisting of an APCC promoter, a CPCC promoter, and a Catalase promoter.

(10) The transformant of the YFU3 strain or the HKN1 strain according to any one of (3), (4), and (6) to (9), in which the nucleic acid does not include a base sequence derived from a cell belonging to another taxonomic species.

(11) The transformant of the algae belonging to Cyanidiophyceae according to (10), in which the nucleic acid has been introduced into the cells by using an auxotrophy-related gene as a selection marker.

(12) The transformant of the YFU3 strain or the HKN1 strain according to (10), in which the nucleic acid has been introduced into a knockout cell of the auxotrophy-related gene by using the auxotrophy-related gene as a selection marker.

(13) The transformant of the YFU3 strain or the HKN1 strain according to any one of (3), (4), and (9), in which the glutamate decarboxylase gene is a glutamate decarboxylase gene of Cyanidioschyzon merolae.

(14) The transformant of the YFU3 strain or the HKN1 strain according to any one of (6), (7), and (9), in which the homogentisate phytyltransferase gene is a homogentisate phytyltransferase gene of Cyanidioschyzon merolae.

(15) The transformant of the YFU3 strain or the HKN1 strain according to any one of (6), (8), and (9), in which the tocopherol cyclase gene is a tocopherol cyclase gene of Cyanidioschyzon merolae.

(16) The transformant of the YFU3 strain or the HKN1 strain according to any one of (4) and (7) to (9), in which the promoter is a promoter derived from Cyanidioschyzon merolae.

(17) The transformant of the YFU3 strain or the HKN1 strain according to any one of (1) to (16), which is a haploid cell.

(18) The transformant of the YFU3 strain or the HKN1 strain according to any one of (1) to (16), which is a diploid cell.

In addition, as shown in Examples which will be described later, it has been confirmed that the algae belonging to Galdieria also have a haploid cell form and a diploid cell form. Therefore, the algae of the present embodiment may be algae belonging to Galdieria. Examples of the algae belonging to Galdieria include Galdieria sulphuraria (for example, an SAG108.79 strain), Galdieria partita (for example, an NBRC 102759 strain), and the like. Furthermore, the algae of the present embodiment may be algae belonging to Cyanidium other than the YFU3 strain and the HKN1 strain.

[Method for Producing Haploid Algae]

The present invention provides a method for producing a haploid cell of alga, including (a) step of culturing a diploid cell of an alga belonging to Cyanidiophyceae having a diploid cell form and a haploid cell form and (b) step of isolating a haploid cell generated during the culturing.

The algae which belong to Cyanidiophyceae and have a diploid cell form and a haploid cell form (hereinafter, referred to as "the present algae" in some cases) are the same as the algae described above in "[Alga having a diploid cell form and a haploid cell form]". As the present algae, for example, the YFU3 strain, the HKN1 strain, mutants or analogues of these, and the like.

In addition, as shown in Examples which will be described later, it has been confirmed that the algae belonging to Galdieria (Galdieria sulphuraria SAG108.79 and Galdieria partita NBRC 102759) also have a diploid cell form and a haploid cell form. This result implies that in Cyanidiophyceae (for example, Galdieria and Cyanidium), probably, there may be a wide variety of algae having a diploid cell form and a haploid cell form. Therefore, the algae to which the producing method of the present embodiment can be applied may be algae belonging to Galdieria or Cyanidium, and are not limited to those exemplified above. Specific examples of the algae belonging to Galdieria include Galdieria sulphuraria and Galdieria partita.

According to the producing method of the present embodiment, haploid cells of algae can be prepared from diploid cells of the algae. Haploid algae can be transformed more easily compared to diploid algae.

(Step (a))

The step (a) is a step of culturing a diploid cell of an alga (present algae) which belongs to Cyanidiophyceae and has a diploid cell form and a haploid cell form.

The present algae are not particularly limited, and diploid cells of algae, which belong to Cyanidiophyceae and have been found to have a diploid cell form and a haploid cell form, may be cultured. Specific examples thereof include the YFU3 strain (diploid), the HKN1 strain (diploid), and allied species and mutants of these, and the like. In addition, examples thereof also include diploid cells of algae belonging to Galdieria (such as Galdieria sulphuraria and Galdieria partita), diploid cells of algae belonging to Cyanidium, and the like.

Examples of the culture conditions include the culture conditions exemplified in "[Alga belonging to Cyanidiophyceae]" or "[Alga having a diploid cell form and a haploid cell form]". Specifically, the pH condition is pH 1.0 to 6.0 for example, and is preferably pH 1.0 to 5.0. Furthermore, the temperature condition is 15° C. to 50° C. for example, and is preferably 30° C. to 50° C. Examples of the medium include those exemplified above in "[Alga belonging to Cyanidiophyceae]" or "[Alga having a diploid cell form and a haploid cell form]". Among these, a medium using acidic hot spring drainage is preferable. Specific examples of the medium using acidic hot spring drainage is include the Tsukahara mineral spring medium (Hirooka et al. 2016 Front in Microbiology).

The algae of the above embodiment are preferably cultured until the algae enter the stationary phase, and more preferably continuously cultured for an arbitrary period of time in the stationary phase. The duration of culturing is, for example, 2 to 60 days, 3 to 40 days, or 5 to 35 days. The period from the start of culturing to the stationary phase varies with the type of algae. Therefore, the duration of culturing can be set according to the type of algae. Furthermore, cells may be collected from the culture solution in the stationary phase, subcultured, and further cultured for about 1 to 5 days.

(Step (b))

The step (b) is a step of isolating a haploid cell generated during the culturing.

By the culturing in the step (a), diploid cells of the present algae undergo meiosis, and as a result, haploid cells of the present algae are generated. In a case where the haploid cells are observed with an optical microscope, the shape of the haploid cells looks different from the shape of the diploid cells (for example, the haploid cells are found to have a size smaller than that of the diploid cells and found to have no rigid cell wall). Therefore, based on the difference in the cell shape, it is possible to discern the haploid cells. By collecting and isolating the haploid cells by using a Pasteur pipette or the like, it is possible to manufacture haploid cells of the algae.

The isolated haploid cells of the algae may be cultured using the medium exemplified in "[Alga belonging to Cyanidiophyceae]" or "[Alga having a diploid cell form and a haploid cell form]" described above, and the like. By isolating one by one the haploid cells that have appeared in the culture solution of the diploid cells and allowing the isolated cells to grow, it is possible to obtain monoclonal haploid cells of the algae.

In another aspect, the present invention provides a haploid cell of an alga (cell) (present alga) that belongs to Cyanidiophyceae and having a diploid cell form and a haploid cell form. The algae can be obtained by the method for producing haploid algae described above. The present invention also provides a haploid alga (cell) of the YFU3 strain, a haploid alga (cell) of the HKN1 strain, a haploid alga (cells) of algae belonging to Cyanidium, and a haploid alga (cell) of algae belonging to Galdieria. Specific examples of the algae belonging to Galdieria include Galdieria sulphuraria and Galdieria partita.

[Method for Producing a Diploid Alga]

The present invention provides a method for producing a diploid alga of an alga having a diploid cell form and a haploid cell form, the method including (a) step of mixing together two or more kinds of haploid cells and culturing the cells, and (b) step of isolating a diploid cell generated during the culturing.

As shown in Examples which will be described later, by mixing together and culturing haploid cells, diploid cells can be obtained.

(Step (a))

Step (a) is a step of mixing together and culturing two or more kinds of haploid cells of an alga having a diploid cell form and a haploid cell form.

The two or more kinds of haploid cells, which are mixed together in this step, are preferably algal cells of the same species. It is more preferable to use haploid cells derived from the diploid cells of the same strain.

Examples of the culture conditions include the culture conditions exemplified in "[Alga belonging to Cyanidiophyceae]" or "[Alga having a diploid cell form and a haploid cell form]" described above. Specifically, the pH condition is pH 1.0 to 6.0 for example, and is preferably pH 1.0 to 5.0. Furthermore, the temperature condition is 15° C. to 50° C. for example, and is preferably 30° C. to 50° C. Examples of the medium include the media described in "[Alga belonging to Cyanidiophyceae]" or "[Alga having a diploid cell form and a haploid cell form]" described above.

The cells are preferably cultured, for example, for about 1 to 4 weeks, and may be further subcultured and then cultured for about 3 to 10 days.

(Step (b))

The step (b) is a step of isolating a diploid cell generated during the culturing.

By the culturing in the step (a), haploid cells are mated to each other, and as a result, diploid cells are generated. By collecting and isolating the diploid cell by using a Pasteur pipette or the like, a diploid alga can be prepared.

The isolated diploid algae may be cultured using the medium exemplified in "[Alga belonging to Cyanidiophyceae]" or "[Alga having a diploid cell form and a haploid cell form]" described above (preferably an artificial synthetic medium such as M-Allen medium), and the like.

In another aspect, the present invention provides a diploid alga (cell) of an alga (present alga) which belongs to Cyanidiophyceae and has a diploid cell form and a haploid cell form. The alga can be obtained by the method for producing a diploid alga described above. The present invention also provides a diploid alga (cell) of the YFU3 strain, a diploid alga (cell) of the HKN1 strain, and a diploid alga (cell) of an alga belonging to Cyanidioschyzon. Specific examples of the algae belonging to Cyanidioschyzon include Cyanidioschyzon merolae.

[Culture of the Present Algae]

The present invention provides an alga culture containing algae (present algae) which belong to Cyanidiophyceae and have a diploid cell form and a haploid cell form. In the alga culture of the present embodiment, the ratio of the number of haploid algal cells to the total number of algal cells is 70% to 100%.

Presumably, in the natural world, the present algae may exist as both the diploid cells and haploid cells. However, all of the known algae belonging to Galdieria and Cyanidium are discovered as cells having a rigid cell wall. Therefore, it is considered that most of the present algae may exist as diploid cells in nature.

On the other hand, according to the method for producing a haploid alga of the above embodiment, when the diploid cells of the present algae are cultured until they enter the stationary phase and then continuously cultured as they are, the diploid cells of the present algae undergo meiosis, and as a result, haploid cells of the present algae appear. The haploid cells of the present algae grow by two-cell division, and the proportion of the haploid cells of the present algae increases as the culture is continued. Then, by further continuing the culture or isolating the haploid cells and culturing them, it is possible to obtain an alga culture in which the proportion of the haploid cells of the present algae is 70% to 100%.

The present algae are not particularly limited, and diploid cells of algae which belong to Cyanidiophyceae and are confirmed to have a diploid cell form and a haploid cell form may be cultured. Specific examples thereof include the YFU3 strain (diploid), the HKN1 strain (diploid), allied species and mutants of these, and the like. In addition, examples thereof also include diploid cells of algae belonging to Galdieria (such as Galdieria sulphuraria and Galdieria partita), diploid cells of algae belonging to Cyanidium, and the like.

Examples of the culture conditions for the present algae in the form of diploid cells are the same as the culture conditions exemplified in "[Alga belonging to Cyanidiophyceae]" or "[Alga having a diploid cell form and a haploid cell form]" described above.

In the alga culture of the present embodiment, the proportion of the haploid cells is 70 to 100%, which is significantly different from the proportion of haploid cells in nature.

In another aspect, the present invention provides a cell population including diploid cells of algae which belong to Cyanidiophyceae and have a diploid cell form and a haploid cell form. As the algae belonging to Cyanidiophyceae, for example, the YFU3 strain, the HKN1 strain, mutants of these, and algae belonging to Cyanidioschyzon. Examples of the algae belonging to Cyanidioschyzon include Cyanidioschyzon merolae.

In another aspect, the present invention provides a cell population including haploid cells of algae which belong to Cyanidiophyceae and have a diploid cell form and a haploid cell form. As the algae belonging to Cyanidiophyceae, for example, the YFU3 strain, the HKN1 strain, mutants of these, algae belonging to Cyanidium other than the above, and algae belonging to Galdieria. Examples of the algae belonging to Galdieria include Galdieria sulphuraria and Galdieria partita.

In another aspect, the present invention provides a cell population of algae that belong to Cyanidiophyceae and have a diploid cell form and a haploid cell form, in which the diploid cells and the haploid cells are mixed together.

[Drying and Swelling Treatment Product of the Present Algae]

The present invention provides a dry and swollen product obtained by performing a drying and swelling treatment on algae (present algae) which belong to Cyanidiophyceae and have a diploid cell form and a haploid cell form.

By performing a drying and swelling treatment on the present algae, it is possible to kill the algal cells. Therefore, even a transformant obtained not using self-cloning can be handled in an open system. "Drying and swelling treatment" refers to a treatment of drying algal cells and then adding an aqueous medium or the like to the dried product so as to wet again the dried product. Specific examples of the drying and swelling treatment include the cell disruption treatment described above in (3).

The present algae subjected to the drying and swelling treatment may be diploid cells, haploid cells, or a mixture of diploid cells and haploid cells. For example, the present algae may be cells collected from the alga culture of the above embodiment. The ploidy-variable algae subjected to the drying and swelling treatment are preferably haploid cells.

[Extract of the Present Algae]

As described above, the present algae are rich in nutrients such as amino acids, vitamins, proteins, lipids, and dietary fiber. Accordingly, the present algae can be used as a nutrient composition or a nutritional supplement which will be described below. In addition, in a case where the present algae are blended with foods, feeds, pet foods, cosmetics, and the like, it is possible to provide nutrient-enriched products. Furthermore, in the products described above, an extract of the present algae may be used instead of or together with the present algae. Therefore, the present invention also provides an extract of the present algae.

In the present specification, "extract of the present algae" refers to a substance obtained by extracting intracellular components from cells of the present algae by performing a physical treatment or a chemical treatment. For example, the extract of the present algae may be a cell disruption product obtained by disrupting the cells of the present algae by means of a physical treatment or a chemical treatment. In addition, the extract of the present algae may be a substance obtained by concentrating the cell disruption product, a substance obtained by removing solid contents from the cell disruption product, or a substance obtained by separating some components from the cell disruption product.

The method of the physical treatment or the chemical treatment for the cells is not particularly limited, and the methods generally used for cell disruption can be used. Examples of the physical treatment include cell disruption performed by means of glass beads, a mortar, an ultrasonic treatment, a French press, a homogenizer, and the like.

Examples of the chemical treatment include a neutralization treatment, a hypotonic treatment, a freeze-thaw treatment, a drying and swelling treatment, and the like. More specifically, examples thereof include the cell rupturing treatments (A) to (C) described above.

In a case where the cell disruption product is concentrated, the concentration method is not particularly limited, and a generally used concentration method may be used. Examples of the concentration method for the cell disruption product include drying, freeze-drying, drying under reduced pressure, and the like.

Furthermore, in a case where solid contents are removed from the cell disruption product, the solid content-removing method is not particularly limited, and it is possible to use a method that is generally used for removing solid contents. Examples of the solid content-removing method include filtration, centrifugation, and the like.

In a case where some components are separated from the cell disruption product, the separation method is not particularly limited, and it is possible to use a method generally used for separation, purification, and the like for biochemical substances. Examples of the separation method include salting out, dialysis, solvent extraction, adsorption, column chromatography, ion exchange chromatography, and the like. Each of these methods may be used singly. Alternatively, two or more kinds of treatments may be used in combination. Here, a substance purified into a single component is excluded from "extract of the present algae". The extract of the present algae preferably contains 10 or more kinds of cell components of the present algae, more preferably contains 15 or more kinds of cell components of the present algae, and even more preferably contains 20 or more kinds of cell components of the present algae.

The extract of the present algae preferably contains a nutrient selected from the group consisting of amino acids, vitamins, proteins, lipids, and dietary fiber, and more preferably contains a nutrient selected from the group consisting of amino acids and vitamins. Specific examples of the amino acids include isoleucine, leucine, lysine, methionine, cystine, phenylalanine, tyrosine, threonine, tryptophan, valine, arginine, histidine, alanine, aspartic acid, glutamic acid, glycine, proline, serine, $\gamma$-aminobutyric acid, and the like. Specific examples of the vitamins include vitamin A, $\beta$-carotene, vitamin C, vitamin E, vitamin $K_1$, vitamin $K_2$, folic acid, and the like.

[Nutrient Composition]

In one embodiment, the present invention provides a nutrient composition containing the algae belonging to Cyanidiophyceae or an extract thereof.

The nutrient composition of the present embodiment contains the algae belonging to Cyanidiophyceae or an extract thereof. Accordingly, the nutrient composition is rich in nutrients abundantly contained in the algae. For example, the nutrient composition can be rich in nutrients selected from the group consisting of amino acids, vitamins, proteins, lipids, and dietary fiber. Particularly, the nutrient composition can be rich in nutrients selected from the group consisting of amino acids and vitamins. Therefore, the nutrient composition can be used by being blended with a nutritional supplement, a food, a feed, a pet food, a cosmetic, or the like which will be described later.

The algae belonging to Cyanidiophyceae are not particularly limited. As the algae, for example, the present algae or algae belonging to Cyanidioschyzon are preferable.

The present algae may be diploid cells, haploid cells, or a mixture of diploid cells and haploid cells. For example, the present algae may be cells collected from the alga culture of the above embodiment. Examples of the present algae contained in the nutrient composition of the present embodiment include those exemplified in "[Alga having a diploid cell form and a haploid cell form]" described above. Specific examples of the present algae include the YFU3 strain, the HKN1 strain, allied species and mutants of these, and the like. Furthermore, examples of the present algae also include algae belonging to Cyanidium other than the above and algae belonging to Galdieria. Among these, the YFU3 strain, the HKN1 strain, mutants of these, and the algae belonging to Galdieria are preferable, and the YFU3 strain, the HKN1 strain, and mutants of these are more preferable.

In a case where either the diploid cells or the haploid cells having no rigid cell wall, it is preferable to use the cells having no rigid cell wall. Using such cells is advantageous because nutrients can be easily extracted. Furthermore, using such cells is advantageous because even in a case where the algal cells are directly blended with the nutrient composition, the nutrients in the algal cells are easily absorbed after the intake of the nutrient composition. For example, in a case where the YFU3 strain, the HKN1 strain, or mutants of these are used, it is preferable to use the YFU3 strain (haploid), the HKN1 strain (haploid), or the mutants of these. In addition, for example, haploid cells of the algae belonging to Galdieria (for example, Galdieria sulphuraria, Galdieria partita, and the like) and haploid cells of the algae belonging to Cyanidium are also preferable. Among these, the YFU3 strain (haploid), the HKN1 strain (haploid), mutants of these, and haploid cells of the algae belonging to Galdieria are preferable.

The algae belonging to Cyanidiophyceae may be algae belonging to Cyanidiophyceae other than the present algae. Among these, the algae belonging to Cyanidioschyzon have no rigid cell wall. Therefore, their cells can be disrupted by a relatively mild treatment such as a neutralization treatment, a hypotonic treatment, a freeze-thaw treatment, or the like. Accordingly, the algae belonging to Cyanidioschyzon (for example, Cyanidioschyzon merolae) are a preferred example of the algae belonging to Cyanidiophyceae.

By being cultured and allowed to grow using an appropriate medium, collected through a known method such as centrifugation or filtration, and subjected to washing, drying, and the like as appropriate, the algae belonging to Cyanidiophyceae can be used in the nutritional supplement of the present embodiment. Alternatively, by being collected from the alga culture of the above embodiment and subjected to washing, drying, and the like as appropriate, the algal cells may be used in the nutrient composition of the present embodiment.

Furthermore, the nutrient composition of the present embodiment may contain an extract of the algae belonging to Cyanidiophyceae instead of or together with the algae belonging to Cyanidiophyceae.

The nutrient composition of the present embodiment may contain other components as appropriate in addition to the algae belonging to Cyanidiophyceae or an extract thereof. Those other components are not particularly limited, and examples thereof include a pharmaceutically acceptable carrier and the like. "Pharmaceutically acceptable carrier" means a carrier which does not inhibit the function of nutrients contained in the algae belonging to Cyanidiophyceae and substantially does not exhibit toxicity to an administration subject. "Substantially does not exhibit toxicity" means that the component does not exhibit toxicity to the administration subject at the usual dose thereof. Examples of the pharmaceutically acceptable carrier include, but are not limited to, excipients, binders, disintegrants, lubricants, emulsifiers, stabilizers, diluents, oleaginous bases, thickeners, antioxidants, reducing agents, oxidants, chelating agents, solvents, and the like. One kind of pharmaceutically acceptable carrier may be used singly, or two or more kinds of pharmaceutically acceptable carriers may be used in combination.

The content of the algae belonging to Cyanidiophyceae or an extract thereof in the nutrient composition of the present embodiment is not particularly limited, and can be appropriately selected, for example, in a range of 1% to 100% by mass. The content of the algae belonging to Cyanidiophyceae or an extract thereof in the nutritional supplement of the present embodiment is preferably 50% to 100% by mass, more preferably 60% to 100% by mass, and even more preferably 70% to 100% by mass. The algae belonging to Cyanidiophyceae or an extract thereof can be appropriately mixed with other components and made into a form such as dry powder, granules, tablets, jelly, a liquid, or capsules according to a common method.

[Nutritional Supplement]

In one embodiment, the present invention provides a nutritional supplement containing the algae belonging to Cyanidiophyceae or an extract thereof.

Nutritional supplements are used by human beings or non-human animals for supplying nutrients, and there is no particular limitation on the dosage form, the degree of purification, and the like thereof. As described above, the algae belonging to Cyanidiophyceae are rich in nutrients such as amino acids and vitamins. Therefore, by using the algae belonging to Cyanidiophyceae or an extract thereof, it is possible to obtain a nutritional supplement rich in nutrients such as amino acids and vitamins.

The nutritional supplement of the present embodiment is rich in nutrients such as amino acids and vitamins. Therefore, the nutritional supplement of the present embodiment can be used for human beings or non-human animals as a nutritional supplement for supplying the nutrients. Examples of the nutrients supplied by the nutritional supplement of the present embodiment include amino acids, vitamins, proteins, lipids, dietary fiber, and the like. Particularly, the nutritional supplement of the present embodiment can be suitably used for supplying amino acids (such as isoleucine, leucine, lysine, methionine, cystine, phenylalanine, tyrosine, threonine, tryptophan, valine, arginine, histidine, alanine, aspartic acid, glutamic acid, glycine, proline, serine, and $\gamma$-aminobutyric acid) and vitamins (such as vitamin A, $\beta$-carotene, vitamin B1, vitamin B2, vitamin B6, vitamin C, vitamin E, vitamin $K_1$, vitamin $K_2$, niacin, inositol, folic acid, and biotin). In a case where the present algae are algae belonging to Cyanidiophyceae, the nutritional supplement of the present embodiment can be particularly suitably used for supplying amino acids (such as isoleucine, leucine, lysine, methionine, cystine, phenylalanine, tyrosine, threonine, tryptophan, valine, arginine, histidine, alanine, aspartic acid, glutamic acid, glycine, proline, serine, and $\gamma$-aminobutyric acid) and vitamins (such as vitamin A, $\beta$-carotene, vitamin B1, vitamin B2, vitamin B6, vitamin C, vitamin E, vitamin $K_1$, vitamin $K_2$, niacin, inositol, folic acid, and biotin).

The nutritional supplement of the present embodiment can be particularly suitably used for supplying $\gamma$-aminobutyric acid, $\beta$-carotene, vitamin C, vitamin E, vitamin $K_1$, vitamin $K_2$, and folic acid.

The nutritional supplement of the present embodiment may contain other components as appropriate in addition to the algae belonging to Cyanidiophyceae and an extract thereof. Those other components are not particularly limited, and examples thereof include a pharmaceutically acceptable carrier and the like. Examples of the pharmaceutically acceptable carrier are the same as those exemplified in "Nutrient composition]" described above. One kind of pharmaceutically acceptable carrier may be used singly, or two or more kinds of pharmaceutically acceptable carriers may be used in combination.

The content of the algae belonging to Cyanidiophyceae or an extract thereof in the nutritional supplement of the present embodiment is not particularly limited, and can be appropriately selected, for example, in a range of 1% to 100% by mass. The content of the algae belonging to Cyanidiophyceae or an extract thereof in the nutritional supplement of the present embodiment is preferably 50% to 100% by mass, more preferably 60% to 99% by mass, and even more preferably 70% to 99% by mass.

The algae belonging to Cyanidiophyceae or an extract thereof can be appropriately mixed with other components and made into a form such as dry powder, granules, tablets, jelly, a liquid, or capsules according to a common method.

Furthermore, the nutritional supplement of the present embodiment may be used as it is for human beings or non-human organisms, or may be used by being blended with a composition for supplying nutrients such as a food, a feed, a pet food, or a cosmetic which will be described later. By blending the nutritional supplement of the present embodiment, it is possible to prepare a composition suitable for supplying nutrients such as amino acids and vitamins.

In another aspect, the present invention provides a method for producing a nutritional supplement, including a step of culturing algae belonging to Cyanidiophyceae, a step of collecting the cultured algae belonging to Cyanidiophyceae, and a step of formulating the collected algae belonging to Cyanidiophyceae.

In another aspect, the present invention provides a method for producing a nutritional supplement, including a step of culturing algae belonging to Cyanidiophyceae, a step of collecting the cultured algae belonging to Cyanidiophyceae, a step of obtaining an extract of the collected algae belonging to Cyanidiophyceae, and a step of formulating the extract of the algae belonging to Cyanidiophyceae.

[Composition for Supplying Nutrients]

In one embodiment, the present invention provides a composition for supplying nutrients containing the nutritional supplement described above.

In the present specification, "composition for supplying nutrients" refers to a composition used by human beings or non-human animals for the intake of nutrients into the body. The intake of nutrients into the body may be oral or parenteral.

The composition for supplying nutrients of the present embodiment is rich in amino acids, vitamins, proteins, lipids, dietary fiber, and the like. These components are nutrients abundantly contained in the aforementioned nutritional supplement.

One of the characteristics of the composition for supplying nutrients of the present embodiment is that the composition is rich in amino acids and vitamins among the above nutrients.

The composition is characterized by being particularly rich in $\gamma$-aminobutyric acid among amino acids and in $\beta$-carotene, vitamin C, vitamin E, vitamin $K_1$, vitamin $K_2$, and folic acid among vitamins. For example, $\gamma$-aminobutyric acid is known to have a brain function improving effect and a blood pressure lowering effect. Furthermore, $\beta$-carotene, vitamin C and vitamin E are known to have an antioxidant activity. In addition, vitamin $K_1$ and vitamin $K_2$ are known to have an osteoporosis improving effect. Moreover, folic acid is known to be necessary for the development of the fetus during pregnancy, and is reported to have a cardiovascular disease improving effect.

Therefore, the intake of the composition for supplying nutrients of the present embodiment can bring about the physical condition improving effects that the aforementioned nutrients have. Therefore, the composition for supplying nutrients of the present embodiment is suitably used for supplying at least one kind of nutrient selected from amino acids, vitamins, proteins, lipids, and dietary fiber. Furthermore, the composition for supplying nutrients of the present embodiment is more suitably used for supplying at least one kind of nutrient selected from the group consisting of amino acids and vitamins.

The composition for supplying nutrients of the present embodiment is not particularly limited as long as the composition is used by human beings or non-human animals for the intake of nutrients into the body. Examples of the composition for supplying nutrients of the present embodiment include foods, feeds, pet foods, cosmetics, and the like.

(Food)

The composition for supplying nutrients of the present embodiment may be a food. Therefore, the present invention also provides a food containing the nutrient composition or the nutritional supplement of the above embodiment. In addition, the present invention also provides a food containing the algae belonging to Cyanidiophyceae or an extract thereof.

In a case where the composition for supplying nutrients of the present embodiment is a food, the nutrient composition or the nutritional supplement described above may be added to the food as a food additive. By adding the aforementioned nutrient composition or nutritional supplement to a food, it is possible to prepare a food enriched with nutrients contained in the aforementioned nutrient composition or nutritional supplement. Therefore, in another aspect, the present invention provides a food additive containing the algae belonging to Cyanidiophyceae or an extract thereof.

By adding the aforementioned nutrient composition or nutritional supplement to a raw material of a food and adding other food additives thereto as appropriate, the food of the present embodiment can be manufactured by a known method according to the type of the food.

In the food of the present embodiment, the type of the food is not particularly limited. Examples of the food include, but are not limited to, various noodles such as Soba, Udon, Harusame, Chinese noodles, instant noodles, and cup noodles; carbohydrates such as bread, flour, rice flour, pancake, and mashed potatoes; beverages such as green vegetable juice, soft drinks, carbonated drinks, nutritious drinks, fruit drinks, vegetable drinks, lactic acid drinks, milk-based drinks, sports drinks, tea, and coffee; bean products such as tofu, Okara, and Natto; various soups such as curry roux, stew, and instant soups; frozen desserts such as ice cream, ice sorbet, and shaved ice; confectioneries such as cookies, candies, gums, chocolates, tablet-shaped sweets, snacks, biscuits, jellies, jams, creams, and other baked cakes; processed marine and livestock products such as Kamaboko, Hanpen, hams, and sausages; dairy products such as processed milk, fermented milk, butter, cheese, and yogurt, oil and fat as well as oil and fat processed foods such as salad oil, oil for frying, margarine, mayonnaise, shortening, whipping cream, and dressing; flavors such as sauces, dressings, Miso, soy sauce, and seasonings; other processed foods such as various retort foods, Furikake, and pickles; and the like.

In the foods described above, the content of the aforementioned nutrient composition or the nutritional supplement is not particularly limited, and may be appropriately set according to the type of the food. Considering the flavor of the food and the like, the content of the aforementioned nutrient composition or nutritional supplement in the food can be, for example, 0.01% to 30% by mass as the content of the algae belonging to Cyanidiophyceae or an extract thereof. From the viewpoint of flavor of the food and the like, the content of the nutrient composition or the nutritional supplement is preferably 0.05% to 20% by mass, more preferably 0.1% to 15% by mass, even more preferably 0.1% to 10% by mass, and particularly preferably 0.1% to 5% by mass.

The food may be a functional food or a dietary supplement. The functional food or the dietary supplement may be in the form of a general food as described above, or in the form of dry powder, granules, tablets, jellies, drinks, and the like. In this case, by mixing the aforementioned nutrient composition or nutritional supplement with other components as appropriate, foods in the form of dry powders, granules, tablets, jellies, drinks, and the like can be prepared according to a common method. Those other components are not particularly limited, and examples thereof include a pharmaceutically acceptable carrier and the like. Examples of the pharmaceutically acceptable carrier are the same as those exemplified in "[Nutrient composition]" described above. Furthermore, in order to improve the flavor and the like, sweeteners, flavoring agents, various flavors, spices, oils and fats, other food additives, and the like may be used as those other components. One kind of each of those other components may be used singly, or two or more kinds of those other components may be used in combination.

In the functional food or the dietary supplement described above, the content of the aforementioned nutrient composition or nutritional supplement is not particularly limited, and may be appropriately set according to the type of the functional food or the dietary supplement. In a case where the functional food or the dietary supplement is in the form of dry powder, granules, tablets, or the like, in the functional food or the dietary supplement, the content of the nutrient composition or the nutritional supplement described above is, for example, 0.1% to 99% by mass as the content of the algae belonging to Cyanidiophyceae or an extract thereof.

From the viewpoint of flavor and efficient supplement of nutrients, the content of the nutrient composition or the nutritional supplement described above is preferably 1% to 90% by mass, more preferably 10% to 85% by mass, even more preferably 20% to 85% by mass, and particularly preferably 25% to 85% by mass. Furthermore, in a case where the functional food or the dietary supplement is in the form of a jelly, a drink, or the like, in the functional food or the dietary supplement, the content of the nutritional supplement described above is, for example, 0.05% to 80% by mass as the content of the algae belonging to Cyanidiophyceae or an extract thereof. From the viewpoint of flavor and efficient supplement of nutrients, the content of the nutritional supplement described above is preferably 1% to 75% by mass, more preferably 10% to 70% by mass, even more preferably 15% to 70% by mass, and particularly preferably 20% to 70% by mass.

The food of the present embodiment can be ingested for efficiently supplying the aforementioned nutrients contained in the algae belonging to Cyanidiophyceae. Particularly, the food of the present embodiment can be ingested for efficiently supplying nutrients selected from the group consisting of amino acids, vitamins, proteins, lipids, and dietary fiber. The food of the present embodiment is effective for the intake of nutrients selected from the group consisting of amino acids and vitamins among the nutrients described above.

(Feed and Pet Food)

The composition for supplying nutrients according to the present embodiment may be a feed or a pet food. Accordingly, the present invention also provides a feed or a pet food containing the nutrient composition or the nutritional supplement of the above embodiment. In addition, the present invention also provides a feed or a pet food which contains the algae belonging to Cyanidiophyceae or an extract thereof.

In a case where the composition for supplying nutrients of the present embodiment is a feed or a pet food, the nutrient composition or the nutritional supplement described above may be added to the feed or the pet food as a feed additive or a pet food additive. By adding the aforementioned nutrient composition or nutritional supplement to a feed or a pet food, it is possible to prepare a feed or a pet food enriched with nutrients contained in the nutrient composition or the nutritional supplement described above. Therefore, in another aspect, the present invention provides a feed additive or a pet food additive containing the algae belonging to Cyanidiophyceae or an extract thereof.

By adding the aforementioned nutrient composition or nutritional supplement to raw materials of a feed or raw materials of a pet food and adding other feed additives or pet food additives as appropriate, the feed or the pet food of the present embodiment can be manufactured by a known method according to the type of the raw materials of the feed or the pet food.

The type of animal to which the feed or the pet food of the present embodiment is provided is not particularly limited. Examples of thereof include, but are not limited to, livestock (such as cows, pigs, chickens, horses, sheep, and goats), fish, shellfish, pets (such as dogs, cats, hamsters, rabbits, parakeets, tropical fish, reptiles, amphibians, and insects), and the like.

In the feed or the pet food of the present embodiment, the content of the aforementioned nutrient composition or nutritional supplement is not particularly limited, and may be appropriately set according to the type of the feed or the pet food. In the feed or the pet food, the content of the aforementioned nutrient composition or nutritional supplement is, for example, 0.01% to 90% by mass as the content of the algae belonging to Cyanidiophyceae or an extract thereof. The content of the aforementioned nutrient composition or nutritional supplement is preferably 0.1% to 80% by mass, more preferably 1% to 70% by mass, and particularly preferably 1% to 60% by mass.

The feed or the pet food of the present embodiment can be used for efficiently supplying the aforementioned nutrients, which are contained in the algae belonging to Cyanidiophyceae, to the animal. The feed or the pet food of the present embodiment can be used particularly for efficiently supplying nutrients, which are selected from the group consisting of amino acids, vitamins, proteins, lipids, and dietary fiber, to the animal. The feed or the pet food of the present embodiment is effective for the intake of nutrients selected from the group consisting of amino acids and vitamins among the above nutrients.

(Cosmetic)

The composition for supplying nutrients according to the present embodiment may be a cosmetic. Therefore, the present invention also provides a cosmetic containing the nutrient composition or the nutritional supplement of the above embodiment. In addition, the present invention also provides a cosmetic containing the algae belonging to Cyanidiophyceae or an extract thereof.

In a case where the composition for supplying nutrients of the present embodiment is a cosmetic, the nutrient composition or the nutritional supplement described above may be added to the cosmetic as a cosmetic additive. By adding the aforementioned nutrient composition or nutritional supplement to the cosmetic, it is possible to prepare a cosmetic containing the nutrients contained in the nutrient composition or the nutritional supplement described above. Therefore, in another aspect, the present invention provides a cosmetic additive containing the algae belonging to Cyanidiophyceae or an extract thereof.

By mixing the aforementioned nutrient composition or nutritional supplement with other components as appropriate, the cosmetic of the present embodiment can be manufactured by a known method according to the type of the cosmetic. Those other components are not particularly limited, and examples thereof include a pharmaceutically acceptable carrier and the like. Examples of the pharmaceutically acceptable carrier are the same as those exemplified in "[Nutrient composition]" described above. In addition, materials known as cosmetic additives may be used as those other components. One kind of each of those other components may be used singly, or two or more kinds of those other components may be used in combination.

In the cosmetic of the present embodiment, the type of the cosmetic is not particularly limited. Examples of the cosmetic include, but are not limited to, skin care cosmetics such as toners, emulsions, lotions, creams, gels, sunscreens, facial packs, masks, and serums; makeup products such as foundations, makeup bases, lipsticks, lip glosses, and blushers; cleansers such as facial cleansers, body washes, and cleansing agents; hair care cosmetics such as shampoos, rinses, hair conditioners, treatments, and hair styling agents; body care cosmetics such as body powders and body lotions; and the like.

In the cosmetic of the present embodiment, the content of the aforementioned nutrient composition or nutritional supplement is not particularly limited, and may be appropriately set according to the type of the cosmetic. Considering the texture of the cosmetic and the like, the content of the aforementioned nutrient composition or nutritional supplement in the cosmetic can be, for example, 0.01% to 30% by mass as the content of the algae belonging to Cyanidiophyceae or an extract thereof. From the viewpoint of texture of the cosmetic and the like, the content of the nutrient composition or the nutritional supplement is preferably 0.1% to 20% by mass, more preferably 0.1% to 15% by mass, even more preferably 0.1% to 10% by mass, and particularly preferably 0.1% to 5% by mass.

The cosmetic of the present embodiment can be used by being applied to the skin or hair so as to supply the aforementioned nutrients, which are contained in the algae belonging to Cyanidiophyceae, to the skin or hair. Particularly, the cosmetic of the present embodiment can be used by being applied to the skin or hair so as to supply nutrients, which are selected from the group consisting of amino acids, vitamins, proteins, lipids, and dietary fiber, to the skin or hair. The cosmetic of the present embodiment is effective for supplying nutrients selected from the group consisting of amino acids and vitamins among the above nutrients.

In another aspect, the present invention provides a method for producing a food, including a step of blending algae belonging to Cyanidiophyceae or an extract thereof with a food.

In another aspect, the present invention provides a method for producing a functional food or a dietary supplement, including a step of mixing algae belonging to Cyanidiophyceae or an extract thereof with a pharmaceutically acceptable carrier.

In another aspect, the present invention provides a method for producing a feed or a pet food, including a step of blending algae belonging to Cyanidiophyceae or an extract thereof with a feed or a pet food.

In another aspect, the present invention provides a method for producing a cosmetic, including a step of blending algae belonging to Cyanidiophyceae or an extract thereof with a cosmetic.

In another aspect, the present invention provides a method for producing a food additive, a feed additive, a pet food additive, or a cosmetic additive, including a step of culturing algae belonging to Cyanidiophyceae, a step of collecting the cultured algae belonging to Cyanidiophyceae, and a step of formulating the collected algae belonging to Cyanidiophyceae.

In another aspect, the present invention provides a method for producing a food additive, a feed additive, a pet food additive, or a cosmetic additive, including a step of culturing algae belonging to Cyanidiophyceae, a step of collecting the cultured algae belonging to Cyanidiophyceae, a step of obtaining an extract of the collected algae belonging to Cyanidiophyceae, and a step of formulating the extract of the algae belonging to Cyanidiophyceae.

[Method for Producing Nutrient]

In one embodiment, the present invention provides a method for producing a nutrient. The method for producing a nutrient of the present embodiment includes (a) step of disrupting cells of algae belonging to Cyanidiophyceae so as to obtain a cell disruption product and (b) step of separating at least one kind of nutrient from the cell disruption product.

Hereinafter, each of the steps of the producing method of the present embodiment will be described.

(Step (a))

The step (a) is a step of disrupting cells of algae belonging to Cyanidiophyceae so as to obtain a cell disruption product.

As the algae belonging to Cyanidiophyceae used in this step, for example, the present algae described above and algae belonging to Cyanidioschyzon (for example, Cyanidioschyzon merolae) are suitable. As the present algae, for example, the same algae as those listed in "[Alga having a diploid cell form and a haploid cell form]" described above are suitable. Specific examples thereof include the YFU3 strain, the HKN1 strain, allied species and mutants of these, and the like. Furthermore, examples thereof also include algae belonging to Cyanidium other than the above and algae belonging to Galdieria. Among these, the YFU3 strain, the HKN1 strain, mutants of these, and the algae belonging to Galdieria are preferable, and the YFU3 strain, the HKN1 strain, and mutants of these are more preferable.

The present algae may be diploid cells, haploid cells, or a mixture of diploid cells and haploid cells.

For example, the present algae may be cells collected from the alga culture of the above embodiment. Therefore, the producing method of the present embodiment also provides a method for producing a nutrient, including (a) step of collecting algae from the alga culture of the above embodiment, (b) step of disrupting cells of the algae so as to obtain a cell disruption product, and (c) step of separating at least one kind of nutrient from the cell disruption product.

In a case where either the diploid cells or the haploid cells have no rigid cell wall, it is preferable to use the cells having no rigid cell wall. The cells having no rigid cell wall can be disrupted by a relatively mild treatment. For example, in a case where the YFU3 strain, the HKN1 strain, or mutants of these are used, it is preferable to use the YFU3 strain (haploid), the HKN1 strain (haploid), or mutants of these. In addition, for example, haploid cells of the algae belonging to Galdieria (such as Galdieria sulphuraria, and Galdieria partita) and haploid cells of the algae belonging to Cyanidium are also preferable. Among these, the YFU3 strain (haploid), the HKN1 strain (haploid), mutants of these, and haploid cells of the algae belonging to Galdieria are preferable.

The method for disrupting the cells of the algae belonging to Cyanidiophyceae is not particularly limited, and a known method can be used. Examples of the method for disrupting the cells include physical treatments by means of glass beads, a mortar, an ultrasonic treatment, a French press, a homogenizer, and the like; chemical treatments such as a neutralization treatment, a hypotonic treatment, a freeze-thaw treatment, and a drying and swelling treatment; and the like. One kind of each of these treatments may be performed singly, or two or more kinds of these treatments may be performed in combination.

In a case where the algae belonging to Cyanidiophyceae have no rigid cell wall, it is possible to disrupt the cells by relatively mild treatment such as a neutralization treatment, a hypotonic treatment, a freeze-thaw treatment, or a drying and swelling treatment. These treatments bear energy costs lower than that of physical treatments and can be performed in a simple manner. Therefore, in a case where the algae belonging to Cyanidiophyceae that do not have a rigid cell wall are used, as the cell disruption method, a neutralization treatment, a hypotonic treatment, a freeze-thaw treatment, and a drying and swelling treatment are preferable. Furthermore, any of the cell rupturing treatments (1) to (3) described above is also an example suitable as the cell disruption method.

Examples of the neutralization treatment method include a method of immersing the algal cells, which belong to Cyanidiophyceae and have no rigid cell wall, in a neutralizing solution at a pH of about 7 to 10. The algae belonging to Cyanidiophyceae are adapted to the acidic pH range. Therefore, in a case where the algae have no rigid cell wall, the cells are disrupted by being immersed in the neutralizing solution which is neutral or basic. The composition of the neutralizing solution is not particularly limited, and for example, a buffer such as a phosphate buffer and a Tris buffer can be used. The time for which the cells are immersed in the neutralizing solution may be set such that the cells are disrupted. For example, the cells are immersed in the neutralizing solution for about one week. For example, the cell rupturing treatment described above in (1) is suitable.

Examples of the hypotonic treatment method include a method of immersing the algal cells belonging to Cyanidiophyceae in a hypotonic solution such as water. Among the algae belonging to Cyanidiophyceae, those having no rigid cell wall undergo cell rupture by being immersed in a hypotonic solution such as water. The composition of the hypotonic solution is not particularly limited as long as it is a hypotonic liquid in which the algal cells belonging to Cyanidiophyceae are ruptured. Examples of the hypotonic solution include water, a buffer with a low salt concentration, and the like. The time for which the cells are immersed in the hypotonic solution may be set such that the cells are ruptured. For example, the cells are immersed in the hypotonic solution for about 1 to 30 minutes. Furthermore, after the immersion in the hypotonic solution, a process of collecting the algal cells by centrifugation or the like and resuspending the cells in the hypotonic solution may be repeated. The number of times of resuspension is not particularly limited, but is, for example, 1 to 5. For example, the cell rupturing treatment described above in (2) is suitable.

Examples of the freeze-thaw treatment method include a method in which a cycle of freezing and thawing is performed once or more on the algal cells belonging to Cyanidiophyceae. The number of cycles of freezing and thawing is not particularly limited, and may be set such that the algal cells belonging to Cyanidiophyceae having no rigid cell wall are disrupted. The number of cycles of freezing and thawing is, for example, about 1 to 5. Each of the freezing time and the thawing time is not particularly limited, but is, for example, about 10 to 30 minutes.

Examples of the drying and swelling treatment method include a method in which a cycle of drying and resuspension in a buffer is performed once or more on the algal cells. The number of cycles of drying and resuspension is not particularly limited, and may be set such that the algal cells belonging to Cyanidiophyceae having no rigid cell wall are disrupted. The number of cycles of drying and resuspension is, for example, about 1 to 5. For example, the cell rupturing treatment described above in (3) is suitable.

By disrupting the algal cells belonging to Cyanidiophyceae by the methods described above, a cell disruption product of the algae belonging to Cyanidiophyceae can be obtained.

(Step (b))

The step (b) is a step of separating at least one kind of nutrient from the cell disruption product of the algae belonging to Cyanidiophyceae.

In this step, the nutrient to be separated is not particularly limited as long as it is a nutrient of the algae belonging to Cyanidiophyceae. As described above in "[Alga having a diploid cell form and a haploid cell form]", the algae belonging to Cyanidiophyceae are rich in nutrients such as amino acids, vitamins, proteins, lipids, and dietary fiber. Therefore, examples of the nutrient to be separated in this step include at least one kind of nutrient selected from the group consisting of amino acids, vitamins, proteins, lipids, and dietary fiber.

In this step, it is preferable to separate at least one kind of nutrient selected from the group consisting of amino acids and vitamins among the nutrients described above. Specific examples of the amino acids include at least one kind of amino acid selected from the group consisting of isoleucine, leucine, lysine, methionine, cystine, phenylalanine, tyrosine, threonine, tryptophan, valine, arginine, histidine, alanine, aspartic acid, glutamic acid, glycine, proline, serine, and γ-aminobutyric acid. As the amino acid, for example, γ-aminobutyric acid is preferable.

Specific examples of the vitamins include at least one kind of vitamin selected from the group consisting of vitamin A, β-carotene, vitamin $B_1$, vitamin $B_2$, vitamin $B_6$, vitamin C, vitamin E, vitamin $K_1$, vitamin $K_2$, niacin, inositol, folic acid, and biotin. Particularly, in a case where the algae belonging to Cyanidiophyceae are the present algae, specific examples of the vitamins include at least one kind of vitamin selected from the group consisting of vitamin A, β-carotene, vitamin C, vitamin E, vitamin $K_1$, vitamin $K_2$, and folic acid. As the vitamins, for example, at least one kind of vitamin selected from the group consisting of β-carotene, vitamin C, vitamin E, vitamin $K_1$, vitamin $K_2$, and folic acid is preferable.

In this step, one kind of nutrient or two or more kinds of nutrients may be separated. Furthermore, amino acids, fat-soluble vitamins (such as vitamin A, β-carotene, vitamin E, vitamin $K_1$, and vitamin $K_2$), water-soluble vitamins (such as vitamin $B_1$, vitamin $B_2$, vitamin $B_6$, vitamin C, niacin, inositol, folic acid, and biotin), and the like may be separated by type.

The method for separating the nutrient from the cell disruption product is not particularly limited, and may be appropriately selected according to the type of the nutrient. As the nutrient separation method, the methods generally used for the separation, purification, and the like for biochemical substances can be used in combination as appropriate. Examples of the separation method include, but are not limited to, centrifugation, washing, salting out, dialysis, recrystallization, reprecipitation, solvent extraction, adsorption, concentration, filtration, gel filtration, ultrafiltration, various types of chromatography (such as thin layer chromatography, column chromatography, ion exchange chromatography, high performance liquid chromatography, and adsorption chromatography), and the like.

(Optional Step)

The producing method of the present embodiment may include other steps in addition to the steps (a) and (b). Examples of those other steps include a step of culturing algae belonging to Cyanidiophyceae (culturing step), a step of collecting the algae belonging to Cyanidiophyceae from a culture solution (collecting step), a step of washing cells of the algae belonging to Cyanidiophyceae (washing step), a step of treating the algae belonging to Cyanidiophyceae at a low temperature (low-temperature treatment step), a step of drying the algae belonging to Cyanidiophyceae (drying step), a step of freezing the algae belonging to Cyanidiophyceae (freezing step), and the like. These steps can be performed before the step (a).

The culturing step can be performed by the method described above in "[Alga belonging to Cyanidiophyceae]" or "[Alga having a diploid cell form and a haploid cell form]". Furthermore, the collecting step can be performed by a known method such as filtration or centrifugation. The washing step can be performed by suspending the cells in a washing solution (such as a buffer) at a pH of 1.0 to 6.0, and then collecting the cells from the washing solution by a method such as filtration or centrifugation.

The low-temperature treatment step can be performed by treating the algae belonging to Cyanidiophyceae at a temperature of 0° C. to 5° C.

For example, in a case where the algal cells belonging to Cyanidiophyceae collected through the culturing step and the collecting step are placed in an environment at a temperature of 0° C. to 5° C., the algal cells can be killed. Therefore, even a transformant obtained not using self-cloning can be handled in an open system. The time of the low-temperature treatment is not particularly limited, and is, for example, 8 days or longer, and preferably 10 days or longer.

The drying step can be performed by drying the algae belonging to Cyanidiophyceae with a dryer such as a room temperature dryer, a low temperature dryer, or a freeze dryer. For example, in a case where the algal cells belonging to Cyanidiophyceae collected through the culturing step and the collecting step are dried with the dryer, the algal cells can be killed. Therefore, even a transformant obtained not using self-cloning can be handled in an open system.

The freezing step can be performed by freezing the algae belonging to Cyanidiophyceae in liquid nitrogen, a freezer, or the like. For example, in a case where the algal cells belonging to Cyanidiophyceae collected through the culturing step and the collecting step are placed in an environment with a temperature equal to or lower than −4° C. and preferably equal to or lower than −20° C., the algal cells can be killed. Therefore, even a transformant obtained not using self-cloning can be handled in an open system.

The time of the freezing treatment is not particularly limited, and is, for example, 10 minutes or longer and preferably 30 minutes or longer.

The nutrient produced by the producing method of the present embodiment can be used for various uses such as nutritional supplements, foods, feeds, pet foods, cosmetics, pharmaceutical products, and reagents.

[Other Aspects]

The algae belonging to Cyanidiophyceae are considered to be resistant to gastric acid because they are resistant to acid. On the other hand, among the algae belonging to Cyanidiophyceae, those having no rigid cell wall (for example, the YFU3 strain (haploid), the HKN1 strain (haploid), algae belonging to Cyanidioschyzon (for example, Cyanidioschyzon merolae), haploids of algae belonging to Galdieria, haploids of algae belonging to Cyanidium, and the like) undergo cell rupture in a neutral environment (pH of about 7 to 10). Therefore, these algae are considered to undergo cell rupture in the intestinal tract. Furthermore, for these algae, a transformation system has been established, and accordingly, any gene can be introduced into the algae. Therefore, by preparing a transformant into which a gene for generating an arbitrary drug has been introduced, the transformant can be used as a capsule of a gastric acid-resistant drug. Consequently, the present invention also provides a pharmaceutical composition containing algae belonging to Cyanidiophyceae into which a drug-generating gene has been introduced.

"Drug-generating gene" means a gene expressed in the cells of algae belonging to Cyanidiophyceae, in which a translation product of the gene generates a drug for treating or preventing diseases in human beings or non-human animals (such as mammals). The translation product of the drug-generating gene may be a drug or may be an enzyme that catalyzes a drug synthesis reaction.

The drug is not particularly limited, and examples thereof include antigenic proteins of pathogenic microorganisms or pathogenic viruses. The pathogenic viruses are not particularly limited, and examples thereof include a rabies virus, a porcine circovirus, a bovine rotavirus, an influenza virus, an AIDS virus, and the like. The algae belonging to Cyanidiophyceae into which antigenic proteins of these pathogenic microorganisms or pathogenic viruses have been introduced can be used as vaccines against infectious diseases caused by the microorganisms or the viruses.

Example

Hereinafter, the present invention will be described based on examples, but the present invention is not limited to the following examples.

[Example 1]Analysis of Components of Algae
Belonging to Cyanidiophyceae (Culturing of Algae Belonging to Cyanidiophyceae)

Cyanidioschyzon merolae 10D was cultured with aeration by using 5 L of a 2× Allen medium. The cells were cultured for 2 weeks at a culturing temperature of about 35° C. under continuous white light (500 mol/m$^2$s).

Table 1 shows the composition of the 2× Allen medium.

TABLE 1

| 2x Allen medium | |
| --- | --- |
| $(NH_4)_2SO_4$ | 2.6 g |
| $KH_2PO_4$ | 0.54 g |
| $MgSO_4 \cdot 7H_2O$ | 0.5 g |
| $CaCl_2 \cdot 2H_2O$ | 0.15 g |
| $FeCl_3 \cdot 6H_2O$ | 0.784 mg |
| $MnCl_2 \cdot 4H_2O$ | 0.144 mg |
| $ZnSO_4 \cdot 7H_2O$ | 0.0888 mg |

TABLE 1-continued

| 2x Allen medium | | |
|---|---|---|
| CoCl$_2$•6H$_2$O | 0.016 | mg |
| Na$_2$MoO$_4$•2H$_2$O | 0.01 | mg |
| Na$_2$EDTA•2H$_2$O | 4 | mg |
| H$_2$SO$_4$ | 1 | ml |
| Distilled water | 999 | ml |

(Analysis of Components of Algae Belonging to Cyanidio-phyceae)

[Amino Acids, Vitamins, and the Like]

The cells of Cyanidioschyzon merolae 10D cultured as described above were collected by centrifugation, and the component analysis thereof was deputed to Japan Food Research Laboratories. The analytical value per wet weight obtained by the component analysis was divided by 0.248 so as to be converted into a value per dry weight.

Tables 2 and 3 show the analysis method for each component.

TABLE 2

| Component | Analysis method | Note |
|---|---|---|
| Isoleucine | Automatic amino acid analysis method | |
| Leucine | Automatic amino acid analysis method | |
| Lysine | Automatic amino acid analysis method | |
| Methionine | Automatic amino acid analysis method | Performic acid oxidation treatment, followed by hydrochloric acid hydrolysis and measurement |
| Cystine | Automatic amino acid analysis method | Performic acid oxidation treatment, followed by hydrochloric acid hydrolysis and measurement |
| Phenylalanine | Automatic amino acid analysis method | |
| Tyrosine | Automatic amino acid analysis method | |
| Threonine | Automatic amino acid analysis method | |
| Tryptophan | High performance liquid chromatography method | |
| Valine | Automatic amino acid analysis method | |
| Arginine | Automatic amino acid analysis method | |
| Histidine | Automatic amino acid analysis method | |
| Alanine | Automatic amino acid analysis method | |
| Aspartic acid | Automatic amino acid analysis method | |
| Glutamic acid | Automatic amino acid analysis method | |
| Glycine | Automatic amino acid analysis method | |
| Proline | Automatic amino acid analysis method | |
| Serine | Automatic amino acid analysis method | |
| γ-Aminobutyric acid | Automatic amino acid analysis method | |

TABLE 3

| Component | Analysis method | Note |
|---|---|---|
| Vitamin A (retinol activity equivalent) | | Each of α-carotene (24 μg) and β-carotene (12 μg) was regarded as retinol activity equivalent (1 μg). |
| α-carotene | High performance liquid chromatography | |
| β-carotene | High performance liquid chromatography | |
| Vitamin B$_1$ | High performance liquid chromatography | |
| Vitamin B$_2$ | High performance liquid chromatography | |
| Vitamin B$_6$ | microbiological assay | Used strain: *Saccharomyces cerevisiae* (*S. uvarum*) ATCC 9080 |
| Vitamin B$_{12}$ | microbiological assay | Used strain: *Lactobacillus delbrueckii* subsp. *lactis* (*L. leichmannii*) ATCC 7830 |
| Vitamin C | High performance liquid chromatography | Made into derivative by using hydrazine, followed by measurement |

TABLE 3-continued

| Component | Analysis method | Note |
|---|---|---|
| Vitamin D | High performance liquid chromatography | |
| Vitamin E | High performance liquid chromatography | |
| Vitamin $K_1$ | High performance liquid chromatography | |
| Vitamin $K_2$ | High performance liquid chromatography | |
| Niacin equivalent | | The total amount of niacin (nicotinic acid equivalent) and 1/60 tryptophan were regarded as niacin equivalent. |
| Niacin (nicotinic acid equivalent) | microbiological assay | Used strain: *Lactobacillus plantarum* ATCC 8014 |
| tryptophan | High performance liquid chromatography | |
| Inositol | microbiological assay | Used strain: *Saccharomyces cerevisiae* (*S. uvarum*) ATCC 9080 |
| Folic acid | microbiological assay | Used strain: *Lactobacillus rhamnosus* (*L. casei*) ATCC 7469 |
| Pantothenic acid | microbiological assay | Used strain: *Lactobacillus plantarum* ATCC 8014 |
| Biotin | microbiological assay | Used strain: *Lactobacillus plantarum* ATCC 8014 |
| Choline | Reinecke salt precipitation | |
| Taurine | Automatic amino acid analysis method | |
| Protein | Kjeldahl method | |
| Lipid | Acidolysis | |
| Dietary fiber | Enzyme-gravimetric method | |

Tables 4 to 6 show the results of the component analysis. Table 4 shows the analysis results of amino acids, Table 5 shows the analysis results of vitamins, and Table 6 shows the analysis results of other nutrients. In Tables 4 and 5, analytical values published for *Chlorella, Euglena*, and *Spirulina* are also shown for reference. In Tables 4 to 6, Cyanidioschyzon merolae 10D is described as "Schyzon".

TABLE 4

| Amino acids | Unit (per dry weight of 100 g) | Chlorella[1] | Euglena[2] | Spirulina[3] | Spirulina[4] | Schyzon |
|---|---|---|---|---|---|---|
| Isoleucine | g | 2.06 | 1.57 | 3.17 | 3.209 | 3.34 |
| Leucine | g | 4.45 | 3.3 | 5.02 | 4.947 | 6.4 |
| Lysine | g | 3.07 | 2.83 | 2.7 | 3.025 | 3.66 |
| Methionine | g | 1.24 | 0.87 | 2.19 | 1.149 | 2.01 |
| Cystine | g | 0.63 | 0.66 | | 0.662 | 0.89 |
| Phenylalanine | g | 2.59 | 1.79 | 5 | 2.777 | 3.5 |
| Tyrosine | g | 1.79 | 1.73 | | 2.584 | 3.94 |
| Threonine | g | 2.53 | 2 | 2.78 | 2.97 | 3.58 |
| Tryptophan | g | 1.09 | 0.7 | 0.84 | 0.929 | 1.21 |
| Valine | g | 3.11 | 2.57 | 3.48 | 3.512 | 4.19 |
| Arginine | g | 3.51 | 4.19 | 3.6 | 4.147 | 6.04 |
| Histidine | g | 1.05 | 1.06 | 1.09 | 1.085 | 1.25 |
| Alanine | g | 4.27 | 3.03 | 4.11 | 4.515 | 5.96 |
| Aspartic acid | g | 4.82 | 3.83 | 5.47 | 5.793 | 7.04 |
| Glutamic acid | g | 6.01 | 4.9 | 8.02 | 8.386 | 7.77 |
| Glycine | g | 3.01 | 2.03 | 2.85 | 3.099 | 3.38 |
| Proline | g | 2.48 | 2.45 | 2.04 | 2.382 | 2.82 |
| Serine | g | 2.15 | 1.71 | 2.74 | 2.998 | 3.54 |
| Total amount[5] | g | 49.86 | 41.22 | 55.1 | 58.169 | 70.52 |
| γ-Aminobutyric acid | g | — | — | — | — | 0.197 |

[1]Information posted on the website of SUN CHLORELLA CORP.

[2]Physiology and Biochemistry of Euglena, Seizaburo Kitaoka, Gakkai Shuppan Center, 1989

[3]Information posted on the website of DIC LIFETEC Co., Ltd.

[4]USDA Food Composition Databases

[5]Total amount of 18 kinds of amino acids of isoleucine to serine

TABLE 5

| Vitamins | Unit (per dry weight of 100 g) | Chlorella[1] | Euglena[2] | Spirulina[3] | Spirulina[4] | Schyzon |
|---|---|---|---|---|---|---|
| Vitamin A | mg | — | — | 16.2 | — | 17.75 |
| α-carotene | mg | 17.4 | — | — | — | 0 |
| β-carotene | mg | | 7.03 | — | — | 212.88 |
| Vitamin B$_1$ | mg | 1.55 | 18.1 | 3.78 | 2.38 | 3.98 |
| Vitamin B$_2$ | mg | 4.73 | 6.06 | 3.99 | 3.67 | 4.06 |
| Vitamin B$_6$ | mg | 1.58 | 1.36 | 0.84 | 0.364 | 1.52 |
| Vitamin B$_{12}$ | μg | 310 | 190 | — | 0 | — |
| Vitamin C | mg | 8 | 5 | — | 10.1 | 56.34 |
| Vitamin D | μg | 794 | — | — | 0 | 0 |
| Vitamin E | mg | 3.7 | 23.8 | 9.1 | 5 | 162.98 |
| Vitamin K$_1$ | μg | 980 | — | 1080 | 25.5 | 4708 |
| Vitamin K$_2$ | μg | 0 | — | 80 | — | 5674 |
| Niacin equivalent | mg | 40.2 | — | 38.5 | 12.82 | 40.64 |
| Inositol | mg | 274 | — | 105 | — | 237 |
| Folic acid | μg | 1200 | 990 | 170 | 94 | 5232 |
| Pantothenic acid | mg | 3.04 | — | 1.3 | 3.48 | 0 |
| Biotin | μg | 213 | — | 30.4 | — | 49.5 |
| Choline | mg | 274 | — | — | 66 | 0 |

[1]–[4]Same as in Table 4

TABLE 6

| Nutrient | Unit (per dry weight of 100 g) | Schyzon |
|---|---|---|
| Taurine | g | 0 |
| Protein | g | 76.056 |
| Lipid | g | 12.5 |
| Dietary fiber | g | 2.01 |

As shown in Table 4, it has been revealed that the total amino acid content is higher in the Cyanidioschyzon merolae 10D than in other algae conventionally used in foods and the like. Furthermore, the content of each of the amino acids tended to be higher in Schyzon than in other algae.

In addition, it has been confirmed that the Cyanidioschyzon merolae contains γ-aminobutyric acid. γ-Aminobutyric acid is a substance that functions as an inhibitory neurotransmitter, and has been found to have a brain function improving effect, a blood pressure lowering action, a sedative action, and the like. Tomato is known as a food rich in γ-aminobutyric acid, and has been reported to contain γ-aminobutyric acid in an amount of 0.062 g/100 g based on wet weight (Overview on Wide-spreading Dietary Supplements for the Appropriate Use in Dialysis Patients [paper]8 GABA, Clinical Dialysis Vol. 24. No. 13, December 2008). It can be said that the γ-aminobutyric acid content in Schyzon is by no means lower than that in tomatoes.

As shown in Table 5, the Cyanidioschyzon merolae tended to be richer in vitamins compared to other algae.

Particularly, the content of β-carotene, vitamin C, vitamin E, vitamin K$_1$, vitamin K$_2$, and folic acid was higher in the Cyanidioschyzon merolae than in other algae.

Almond is known as a food rich in vitamin E, and has been reported to contain vitamin E in an amount of 30.3 mg/100 g based on wet weight (Standard Tables of Food Composition in Japanese, 2015). Furthermore, Natto is known as a food rich in vitamin K, and has been reported to contain vitamin K in an amount of 600 g/100 g based on wet weight (Standard Tables of Food Composition in Japanese, 2015). It can be said that the content of vitamin E and vitamin K is higher in Schyzon than in these foods.

From the above results, it has been confirmed that the content of nutrients such as amino acids and vitamins is higher in the Cyanidioschyzon merolae than in other algae conventionally used in foods and the like.

[Example 2]Preparation of γ-Aminobutyric Acid-Producing Ability-Enhanced Strain (Preparation of Fragment for Transformation)

Fragments for transformation were prepared by the method described in Fujiwara et al. (PLoS One. 2013 Sep. 5; 8 (9): e73608). Table 7 shows the primers used for preparing the fragments for transformation. Hereinafter, the primers used will be described using the Primer No. described in Table 7.

TABLE 7

| No. | Primer | Sequence (5'→3') | SEQ ID NO: |
|---|---|---|---|
| 1 | URA5.3(-897)F | GAACTGAGGGGCGAACGCA | 33 |
| 2 | URA5.3(+471)R | CCCTAGCAGCTGACTGTATC | 34 |
| 3 | D184(773)pqeF | CACCATCACCATCAC GCGTGAGTCAGTTCACTGAC | 35 |
| 4 | D184(+1884)pqeR | AAGCTCAGCTAATTACAGCTTGCTGACCTTACCC | 36 |
| 5 | pQE_R | GTGATGGTGATGGTGATGGG | 37 |
| 6 | pQE_F | TAATTAGCTGAGCTTGGACTCCTG | 38 |

TABLE 7-continued

| No. | Primer | Sequence (5'→3') | SEQ ID NO: |
|---|---|---|---|
| 7 | D184(+25)o250R | TATACGTTCTCGTCGCGTCACCCTCGGGACTTG | 39 |
| 8 | D184(+28)btF | GCAGGCAAAAAGTGT GAAACCGCTCAGCGACCA | 40 |
| 9 | O250(-600)pqeF | AAGCTCAGCTAATTACGACGAGAACGTATAAGGAGTG | 41 |
| 10 | O250(-1)gfpR | GCCCTTGCTCACCATGGTCAACGAACGAAGAAACACA | 42 |
| 11 | GFP(1)F | ATGGTGAGCAAGGGCGAG | 43 |
| 12 | GFP(717)R | CTTGTACAGCTCGTCCATGC | 44 |
| 13 | bt(+1)gfpF | GACGAGCTGTACAAGTAAACTAGCTATTTATCTGGTACATATCATTC | 45 |
| 14 | bt(+200)pqeR | CACCATCACCATCACACACTTTTTGCCTGCACAAGT | 46 |
| 15 | O250(-600)F | CGACGAGAACGTATAAGGAGTG | 47 |
| 16 | bt(+200)R | ACACTTTTTGCCTGCACAAGT | 48 |
| 17 | bt(+200)uraR | TTCGCCCCTCAGTTCACACTTTTTGCCTGCACAAGT | 49 |
| 18 | D184(+28)uraF | AGTCAGCTGCTAGGGGAAACCGCTCAGCGACCA | 50 |
| 19 | D184(1270)F | ACACGAATCACACGGTGCTG | 51 |
| 20 | D184(+1448)R | TTGCCGATAACGCAGAAGAGA | 52 |
| 21 | URA5.3(1412)R | AGGTCGCTGATGCGGAA | 53 |
| 22 | URA5.3_(+4)F | GAATACGTTGAATGATTCCTAATGGGCAGAAGCAAG | 54 |
| 23 | GsURA5.3F | CCGCATCAGCGACCTTGTCGGAACACTCCGCC | 55 |
| 24 | GsURA5.3R | TCATTCAACGTATTCTTCAAGTCGTTG | 56 |

<Preparation of EGFP/URA$_{Cm-Cm}$ Fragment>

In order to prepare a URA$_{Cm-Cm}$ selection marker, a DNA fragment containing the URA5.3 gene (including an 897 bp upstream sequence and a 471 downstream sequence) was amplified by PCR by using the genomic DNA of the Cyanidioschyzon merolae 10D as a template and using primer set No. 1/2. A CMD 184C fragment (including the last 1,961 bp and 1.9 kb downstream sequences of CDC184C ORF) and a pQE80 vector (QIAGEN) were amplified by PCR by using primer set No. 3/4, and primer set No. 5/6 respectively. The CMD184C fragment was subcloned into the pQE80 vector by using an In-Fusion HD Cloning Kit (Clontech Laboratories, Inc.). The resulting pD184 vector was amplified by PCR by using primer set No. 7/8. The upstream sequence of CMO250C (−600 to −1: SEQ ID NO: 9), EGFP ORF (Takara Bio Inc.), and the downstream sequence of p-tubulin (+1 to +200) were amplified by PCR by using primer set No. 9/10, primer set no. 11/12, and primer set No. 13/14 respectively, and subcloned into pQE by using the In-Fusion HD Cloning Kit. By using the resulting pQ250-EGFP vector as a template DNA, an assembly fragment (upstream region of CMO250C [−600 to −1], EGFP ORF, and downstream region of β-tubulin [+1 to +200]) was amplified by PCR by using primer set No. 15/16, and subcloned into the amplified pD184 vector. The resulting pD184-0250-EGFP vector was amplified by PCR by using primer set No. 17/18. The URA$_{Cm-Cm}$ selection marker was subcloned into the amplified pD184-0250-EGFP vector. The resulting pD184-0250-EGFP-URA$_{Cm-Cm}$ vector was used as a template for amplifying an EGFP/URA$_{Cm-Cm}$ fragment by using primer set No. 19/20. The amplified DNA fragment (EGFP/URA$_{Cm-Cm}$ fragment) was used for transformation. The EGFP/URA$_{Cm-Cm}$ fragment was used as a negative control. FIG. 1(A) shows the construct of the EGFP/URA$_{Cm-Cm}$ fragment.

<Preparation of GAD/URA$_{Cm-Cm}$ Fragment>

Figure 1B:
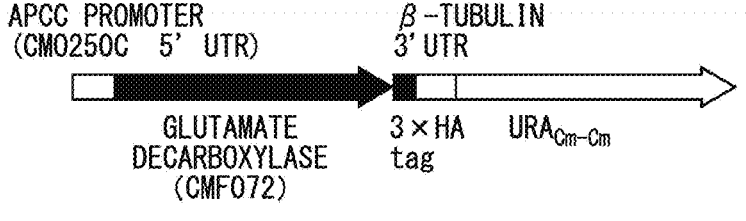
FIG. 1B shows the construct of a fragment for transformation (GAD/URA$_{Cm-Cm}$ fragment) used in Example 2.

A pD184-O250-GAD-URA$_{Cm-Cm}$ vector was prepared by the same method as the method used in "<Preparation of EGFP/URA$_{Cm-Cm}$ Fragment>" described above, except that instead of EGFP ORF, a DNA fragment was used which was obtained by adding a 3×HA tag to the 3' terminal of CMF072C (glutamate decarboxylase: GAD: SEQ ID NO: 3) of Cyanidioschyzon merolae. By using a pD184-0250-GAD-URA$_{Cm-Cm}$ vector as a template and using primer set No. 19/20, a GAD/URA$_{Cm-Cm}$ fragment was amplified by PCR. The amplified DNA fragment (GAD/URA$_{Cm-Cm}$ fragment) was used for transformation. FIG. 1(B) shows the construct of the GAD/URA$_{Cm-Cm}$ fragment.

<Preparation of GAD/URA$_{Cm-Gs}$ Fragment>

Figure 1C:
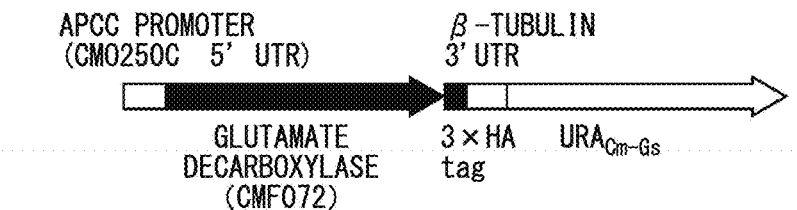
FIG. 1C shows the construct of a fragment for transformation (GAD/URA$_{Cm-Gs}$ fragment) used in Example 2.

In order to remove a sequence including an OMP-decarboxylase domain of URA$_{Cm-Cm}$ from the pD184-0250-GAD-URA$_{Cm-Cm}$ vector, the vector was amplified by PCR by using primer set No. 21/22. A sequence including an OMP-decarboxylase domain of URA5.3 of Galdieria sulphuraria was amplified by PCR by using primer set No. 23/24 and using a URA$_{Cm-Gs}$ selection marker as template DNA, and the sequence was subcloned into the pD184-0250-GAD-URA$_{Cm-Cm}$ vector. The resulting pD184-0250-EGAD-URA$_{Cm-Gs}$ vector was used as a template for amplifying a GAD/URA$_{Cm-Gs}$ fragment by using primer set No. 19/20 and PrimeSTAR (registered trademark) MAX (Takara Bio Inc.). The amplified DNA fragment (GAD/URA$_{Cm-Gs}$ fragment) was used for transformation. FIG. 1(C) shows the construct of the GAD/URA$_{Cm-Gs}$ fragment.

(Transformation)

As a parent strain for transformation, a uracil auxotrophic mutant, Cyanidioschyzon merolae M4 (Minoda et al., Plant Cell Physiol. 2004 June; 45 (6): 667-71.) was used. The cells were allowed to grow in MA2 medium containing uracil (0.5 mg/mL) and 5-fluoroorotic acid (0.8 mg/mL) (Ohnuma M et al. Plant Cell Physiol. 2008 January; 49 (1): 117-20.). The cells were cultured by being shaken at 130 rpm under the conditions of continuous white light (80 mol/m$^2$s) and 40° C. The MA2 medium was coagulated using 0.5% (w/v) gellan gum (Wako Pure Chemical Industries, Ltd.). In order to adjust the pH to 2.3, sulfuric acid was added thereto such that the final concentration became 0.05% (v/v). The cells were transformed by the method described in Ohnuma M et al (Plant Cell Physiol. 2008 January; 49 (1): 117-20.) and Imamura S et al (Plant Cell Physiol. 2010 May; 51 (5): 707-17). For transformation, 4 g of each of the fragments for transformation prepared as above was used. The cells were cultured at 40° C. under continuous white light until colonies were formed. Thereafter, the colonies were moved to starch on MA2 solid medium containing uracil (0.5 mg/mL).

(Checking Number of GAD-Introduced Copies in Transformant)

Real-time PCR was performed using the primers shown in Table 8. It has been confirmed that a wild-type strain of Cyanidioschyzon merolae has one copy of GAD (CMF072C). Therefore, in the EGFP/URA$_{Cm-Cm}$ fragment transformant used as a negative control, a value determined by number of copies amplified using the primer set in A of Table 8 (A value)/number of copies amplified using the primer set in B of Table 8 (B value) is regarded as 1, and the number of copies of GAD (CMF072C) in other transformants was checked.

Figure 4:
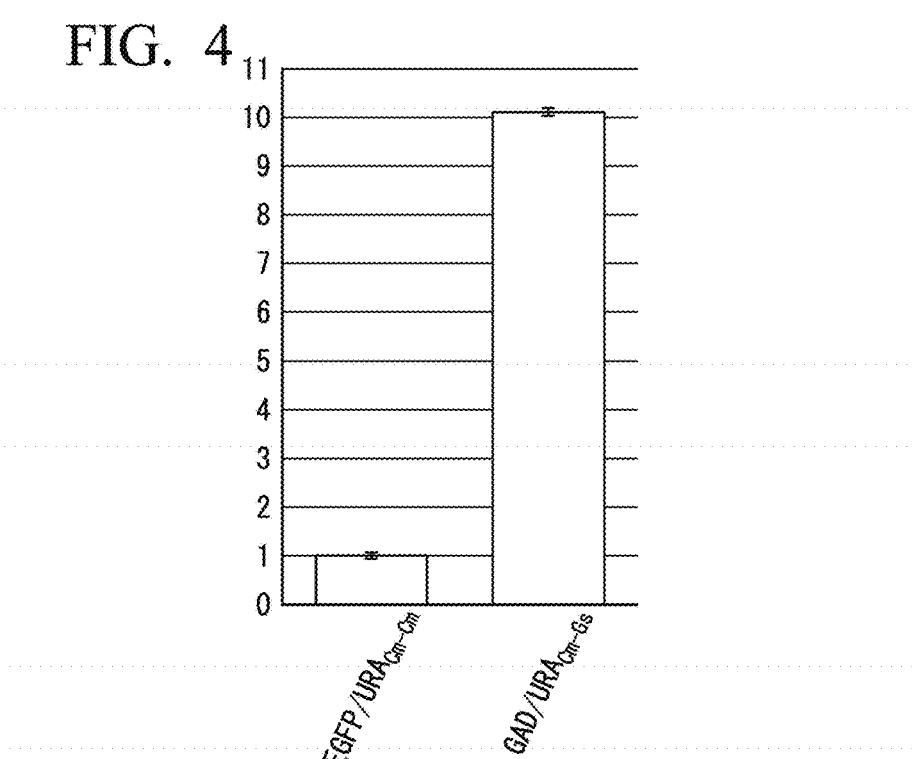
FIG. 4 shows the results obtained by confirming the number of copies of a glutamate decarboxylase gene in a transformant with GAD/URA$_{Cm-Gs}$ fragment prepared in Example 2.

As a result, it has been confirmed that one copy of GAD is introduced into the GAD/URA$_{Cm-Cm}$ fragment transformant by transformation and the transformant has two copies of GAD including endogenous GAD. On the other hand, it has been confirmed that 10 copies of GAD is introduced into the GAD/URA$_{Cm-Gs}$ fragment transformant by transformation and the transformant has 11 copies of GAD including the endogenous GAD. FIG. 4 shows the results of checking the number of copies in the GAD/URA$_{Cm-Gs}$ fragment transformant.

TABLE 8

| | Type of primer | Primer | Sequence (5'→3') | SEQ ID NO: |
|---|---|---|---|---|
| A | Primers for amplifying a portion of GAD gene | GAD(1304)F | TGGTGCGGGTCGGTTTTA | 57 |
| | | GAD(1359)R | CCGAATATCCTGGACCAGCAT | 58 |
| B | Primers for amplifying a genomic DNA sequence irrelevant to GDA gene (internal standard) | CMD184(452)F | CGCTGATCAACCTGGGACTT | 59 |
| | | CMD184(513)R | GTCAAAGCCAAGCTCGATGAG | 60 |

(Immunoblotting)

A cell lysate (4 g as protein amount) of each of the transformants obtained using each of the fragments for transformation was separated by SDS-PAGE (gel having a thickness of 1 mm, 10% acrylamide, 50 minutes at 25 mA). Then, the protein in the gel was transferred to a PVDF membrane (300 V, 400 mA, 75 minutes). Blocking was performed using 5% skim milk, and as a primary antibody, an anti-HA antibody (16B12, 1:2,000) was reacted for 1 hour. Thereafter, as a secondary antibody, an anti-mouse HRP-labeled antibody (1:25,000) was reacted for 1 hour. Chemiluminescent signals were detected using Immobilin Western Chemiluminescent HRP Substrate (Milipore) and LAS-3000 (FUJIFILM Corporation).

Figure 2:
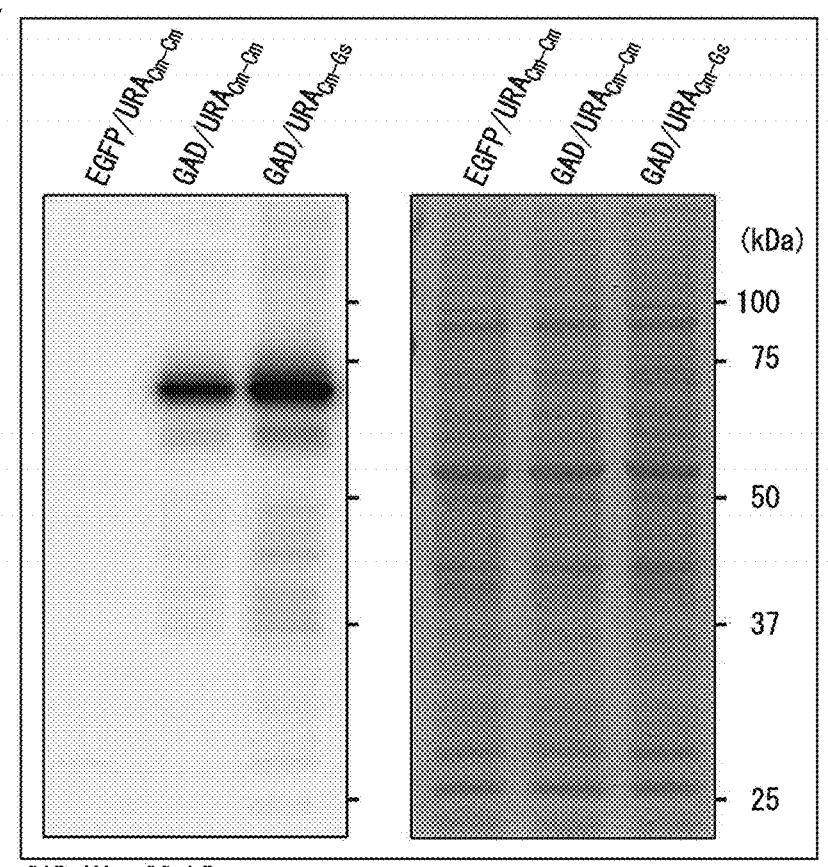
FIG. 2 shows the results of immunoblotting performed using transformants prepared in Example 2. The right figure shows gel stained after SDS-PAGE. The left 25 figure shows the results of immunoblotting using an anti-HA antibody.

FIG. 2 shows the results. In FIG. 2, the right figure shows the gel stained after SDS-PAGE. The left figure shows the results of immunoblotting. Chemiluminescent signals were detected from the GAD/URA$_{Cm-Cm}$ fragment transformant and the GAD/URA$_{Cm-Gs}$ fragment transformant. On the other hand, no signal was detected from those transformed using the EGFP/URA$_{Cm-Cm}$ fragment. This result shows that HA-tagged GAD is expressed in the GAD/URA$_{Cm-Cm}$ fragment transformant and the GAD/URA$_{Cm-Gs}$ fragment transformant. The expression amount of the HA-tagged GAD was larger in the GAD/URA$_{Cm-Gs}$ fragment transformant than in the GAD/URA$_{Cm-Cm}$ fragment transformant.

Figure 3:
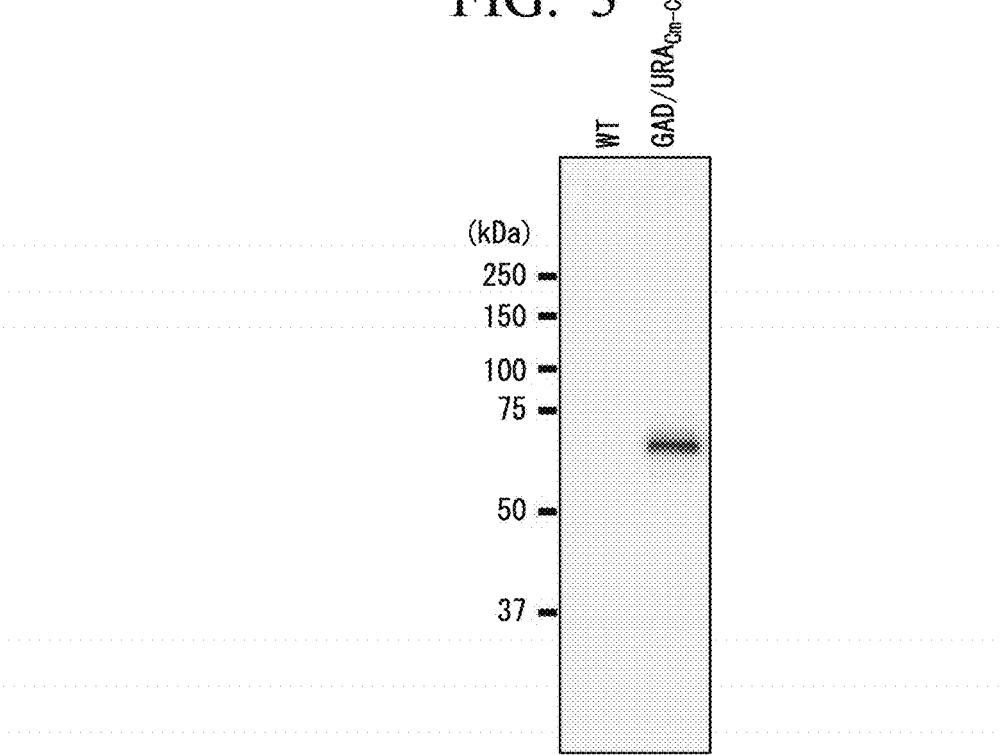
FIG. 3 shows the results of immunoblotting in which a transformant with GAD/URA$_{Cm-Cm}$ fragment prepared in Example 2 is compared with a wild-type strain (WT).

FIG. 3 shows the results of comparison between the GAD/URA$_{Cm-Cm}$ fragment transformant and a wild-type strain (WT). As well as FIG. 2, the expression of the HA-tagged GAD was confirmed in the GAD/URA$_{Cm-Cm}$ fragment transformant, but no signal was detected in the wild-type strain.

(Measurement of Intracellular γ-Aminobutyric Acid Content in Transformant)

The EGFP/URA$_{Cm-Cm}$ fragment transformant, the GAD/URA$_{Cm-Cm}$ fragment transformant, and the GAD/URA$_{Cm-Gs}$ fragment transformant were allowed to grow in MA2 medium. The cells were cultured under the conditions of continuous white light and 40° C.

After being cultured, the cells were collected by centrifugation, and a soluble matter was extracted from the collected cells by using 75% ethanol. γ-Aminobutyric acid in the extracted soluble matter was quantified by OPA-post column derivatization by using HPLC.

The results are shown in Table 9. Table 9 shows a relative concentration determined in a case where the concentration of γ-aminobutyric acid (per dry weight of cells) in the EGFP/URA$_{Cm-Cm}$ fragment transformant is regarded as 1.0.

TABLE 9

| Transformant | Concentration of γ-aminobutyric acid (relative concentration) |
|---|---|
| EGFP/URA$_{Cm-Cm}$ fragment transformant | 1.0 |
| GAD/URA$_{Cm-Cm}$ fragment transformant | 4.04 |
| GAD/URA$_{Cm-Gs}$ fragment transformant | 12.29 |

As shown in Table 9, in the GAD/URA$_{Cm-Cm}$ fragment transformant and the GAD/URA$_{Cm-Gs}$ fragment transformant, the concentration of γ-aminobutyric acid was higher than in the EGFP/URA$_{Cm-Cm}$ fragment transformant as a negative control. Furthermore, in the GAD/URA$_{Cm-Gs}$ fragment transformant, the concentration of γ-aminobutyric acid was higher than in the GAD/URA$_{Cm-Cm}$ fragment transformant. This result shows that the intracellular γ-aminobutyric acid concentration increases according to the number of introduced GAD copies.

From these results, it has been confirmed that in the Cyanidioschyzon merolae, it is possible to increase the intracellular concentration of a specific nutrient by transformation.

[Example 3]Cell Rupturing Treatment for Algae Belonging to Cyanidioschyzon (Drying and Swelling Treatment for Algal Cells)

The Cyanidioschyzon merolae 10D was cultured in the same manner as in Example 1, and 1 mL of the culture solution was subjected to centrifugation (1,500×g, 2 minutes). The supernatant obtained after the centrifugation was discarded, the precipitate of the algal cells was suspended in an isotonic solution (10% sucrose, 20 mM HEPES, pH 7.0) and subjected to centrifugation (1,500×g, 3 minutes), and the algal cells were washed. The supernatant obtained after the centrifugation was discarded, and the precipitate of the algal cells was left in a refrigerator (4° C.) for 3 days so as to dry the algal cells.

Three days later, the algal cells were suspended in 45 μL of an isotonic solution (10% sucrose, 20 mM HEPES, pH 7.0), and subjected to centrifugation (1,500×g, 3 minutes), and centrifugal supernatant and precipitate were collected.

In addition, as algae belonging to Cyanidiophyceae having a rigid cell wall, Cyanidium caldarium RK-1 was cultured and subjected to the same drying and swelling treatment as that described above, and centrifugal supernatant and precipitate were obtained.

(SDS-Polyacrylamide Electrophoresis (SDS-PAGE))

In order to prepare a sample for SDS-PAGE, 15 μL of a 4×SDS-PAGE sample buffer was added to the centrifugal supernatant. Furthermore, 60 μL of 1×SDS-PAGE sample buffer was added to the centrifugal precipitate. SDS-PAGE was performed on the supernatant sample and the precipitate sample prepared as above. The gel after SDS-PAGE was stained with coomassie brilliant blue, and proteins in the centrifugal supernatant and precipitate.

Figure 5:
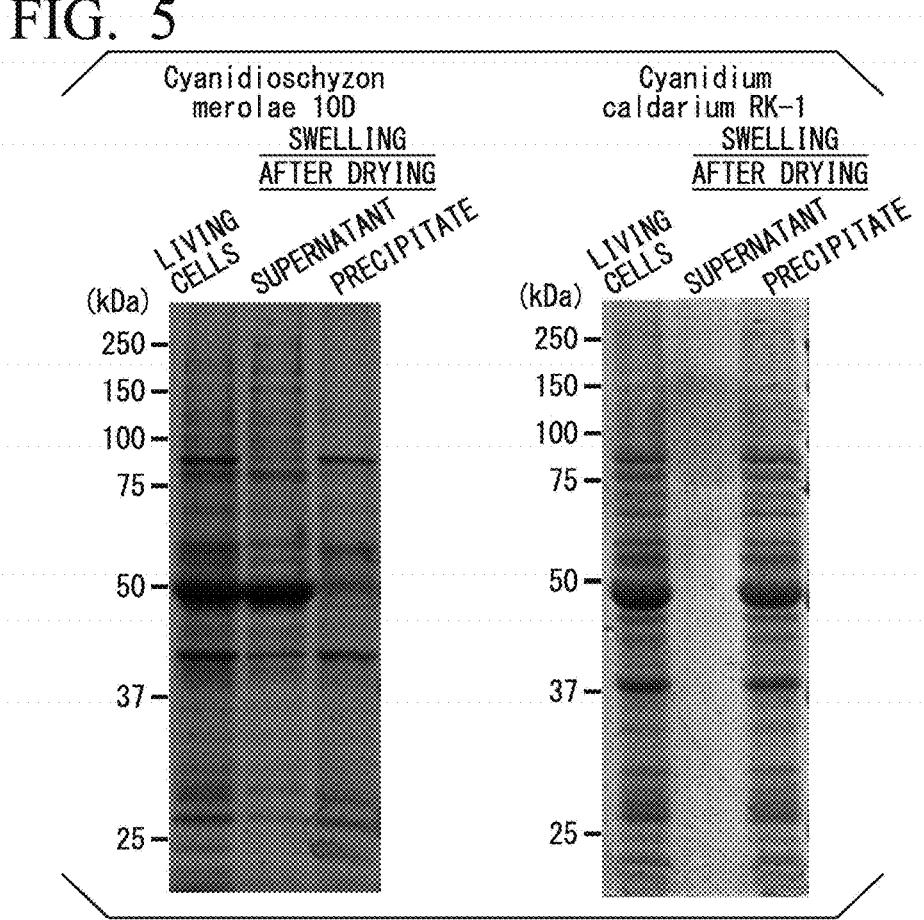
FIG. 5 shows the results of SDS-polyacrylamide electrophoresis performed on a centrifugal supernatant and a centrifugal precipitate which are obtained by performing a drying and swelling treatment on Cyanidioschyzon merolae 10D and Cyanidium Caldarium RK-1 and performing centrifugation on cell suspensions obtained after the swelling treatment.

FIG. 5 shows the results. For the Cyanidioschyzon merolae 10D, a plurality of kinds of proteins were detected in both the supernatant and the precipitate obtained after the drying and swelling treatment. From this result, it has been confirmed that the cells of Cyanidioschyzon merolae 10D are ruptured by the drying and swelling treatment. On the other hand, for the Cyanidium Caldarium RK-1, no protein was detected in the supernatant obtained after the drying and swelling treatment. This result shows that the cells of Cyanidium Caldarium RK-1 are not ruptured by the drying and swelling treatment.

[Example 4]Isolation of Novel Microalgae (Isolation of Novel Microalgae)

Hot acidic water was collected from a hot spring in Yufu-shi, Oita prefecture, Japan. Likewise, hot acidic water was collected from a hot spring in Hakone-machi, Ashigarashimo-gun, Kanagawa prefecture, Japan. The collected hot acidic water was cultured in M-Allen medium (40° C., pH 2.0, 100 mol/m²s), and microalgae were isolated. The YFU3 strain was isolated from the hot acidic water collected in Yufu-shi, and the HKN1 strain was isolated from the hot acidic water collected in Hakone-machi.

Table 10 shows the composition of M-Allen medium (hereinafter, referred to as "MA medium" as well).

TABLE 10

| M-Allen Medium | |
| --- | --- |
| (NH$_4$)$_2$SO$_4$ | 2.64 g |
| KH$_2$PO$_4$ | 0.54 g |
| MgSO$_4$•7H$_2$O | 0.5 g |
| CaCl$_2$•2H$_2$O | 0.14 g |
| A2 trace element | 2 mL |
| Distilled water | 994 mL |
| Adjusted to pH 2.0 by using sulfuric acid Autoclaving followed by addition of 4 mL of A2 Fe stock | |
| A2 trace element | |
| H$_3$BO$_4$ | 2.85 g |
| MnCl$_2$•4H$_2$O | 1.8 g |
| ZnCl$_2$ | 0.105 g |
| Na$_2$MoO$_4$•2H$_2$O | 0.39 g |
| CoCl$_2$•6H$_2$O | 40 mg |
| CuCl$_2$•2H$_2$O | 43 mg |
| Distilled water | 1000 mL |
| A2 Fe stock | |
| EDTA•2Na | 7 g |
| FeCl$_3$•6H$_2$O | 4 g |
| Distilled water | 1000 mL |
| Sterilization using filter | |

(Isolation of Haploid Algae)

Figure 6A:
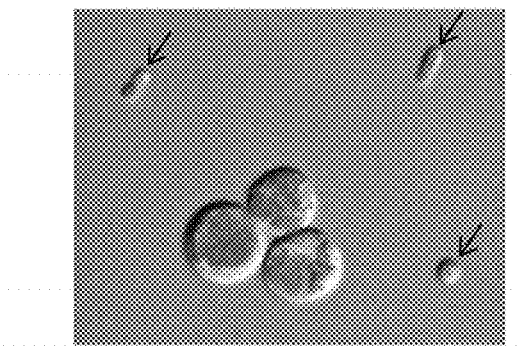
FIG. 6A is a picture of microalgae (Cyanidium sp. HKN1) isolated from a hot spring in Hakone-machi, Ashigarashimo-gun, Kanagawa prefecture, Japan. The picture shows Cyanidium sp. HKN1 in a culture solution that is in the stationary phase after being cultured in MA medium. The arrows indicate Cyanidioschyzon merolae-like cells that appeared in the stationary phase.

The HKN1 strain isolated from the hot acidic water collected in Hakone-machi was cultured in M-Allen medium in a static state for about one month (40° C., 2% CO$_2$). After about one month of the culturing, the growth phase ended, and the cells entered a stationary phase. While the cells were being in the stationary phase, the culture solutions of the HKN1 strain were observed. As a result, small Cyanidioschyzon merolae-like cells were observed in all of the culture solutions. FIG. 6(A) is a picture (magnification: 600×) of a culture solution of the HKN1 strain in the stationary phase. In FIG. 6(A), the arrows indicate Cyanidioschyzon merolae-like cells.

Figure 6B:
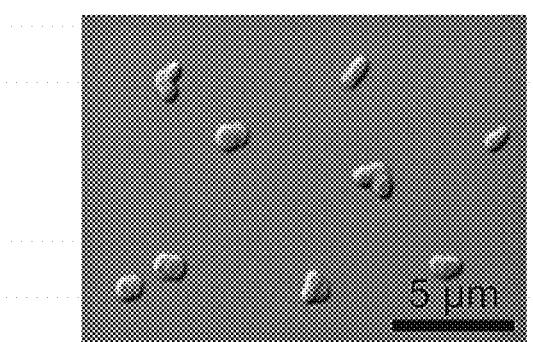
FIG. 6B is a picture of microalgae (Cyanidium sp. HKN1) isolated from a hot spring in Hakone-machi, Ashigarashimo-gun, Kanagawa prefecture, Japan. The picture shows Cyanidioschyzon merolae-like cells isolated from the culture solution in the stationary phase in FIG. 6A.

Under an inverted microscope (CKX41; Olympus Corporation), by using a Pasteur pipette with a sharp tip, the Cyanidioschyzon merolae-like cells were isolated one by one, and the cells were cultured in a static state in 1 mL of a hot spring medium or a modified MA medium (see Example 7). As the hot spring medium, a medium was used which was obtained by adding 10 mM (NH$_4$)$_2$SO$_4$ to hot spring water collected from Tsukahara hot spring (pH 1.15) or Tamagawa hot spring (pH 1.14) (Hirooka S and Miyagishima S Y, Front Microbiol. 2016 Dec. 20; 7: 2022.). After growing in the hot spring medium, the cells having entered the stationary phase were maintained in M-Allen medium or MA2 medium (Ohnuma M et al. Plant Cell Physiol. 2008 January; 49 (1): 117-20.). FIG. 6(B) is a photograph (magnification: 600×) of Cyanidioschyzon merolae-like cells isolated from the culture solution of the HKN1 strain in the stationary phase. The Cyanidioschyzon merolae-like cells maintained their shape even though the cells were continuously cultured thereafter.

Figure 7:
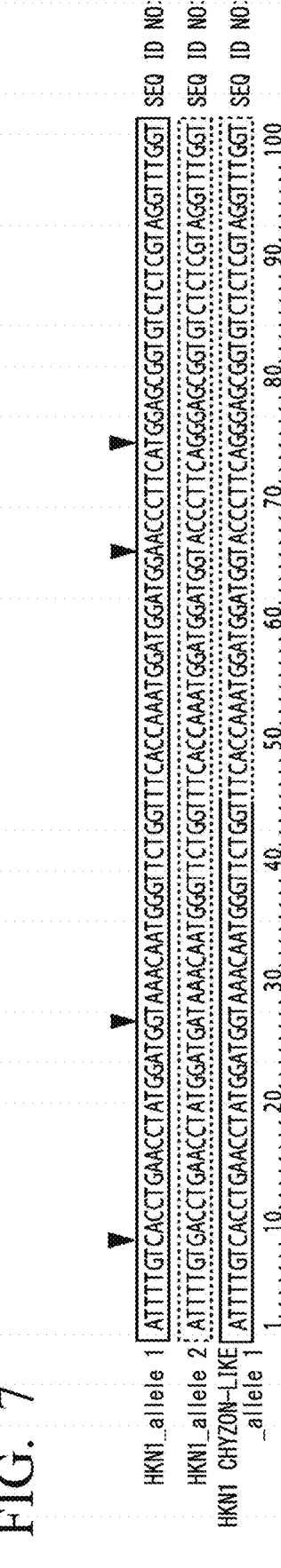
FIG. 7 shows the results of sequence analysis on one genomic region of Cyanidium sp. HKN1 and the Cyanidioschyzon merolae-like cells isolated from the culture solution of Cyanidium sp. HKN1 in the stationary phase. It has been confirmed that the Cyanidioschyzon merolae-like cells are haploids (HKN1 (haploid)) generated by the meiosis of the Cyanidium sp. HKN1 (diploid).

In order to confirm the relationship between the Cyanidioschyzon merolae-like cell isolated as above and the HKN1 strain, the sequence of one genomic region of these cells was analyzed using MiSeq (Illumina, Inc.). As a result, it has been confirmed that all of the Cyanidioschyzon merolae-like cells isolated from the culture solution of the HKN1 strain in the stationary phase (Schyzon-like cells derived from HKN1 strain) have only one allele sequence for the analyzed region and therefore the Cyanidioschyzon merolae-like cells are haploid cells. On the other hand, it has been confirmed that the HKN1 strain has two allele sequences for the analyzed region and therefore the HKN1 strain is diploid cells. Similarly, it has been confirmed that the allele sequence of the Schyzon-like cells derived from the HKN1 strain is a sequence in which two allele sequences of HKN1 are crossed. FIG. 7 shows two allele sequences of the HKN1 strain (HKN1_allele 1: SEQ ID NO: 12, HKN1_allele 2: SEQ ID NO: 13) and an allele sequence of the Schyzon-like cell derived from the HKN1 (HKN1 Schyzon-like_allele 1: SEQ ID NO: 14). In FIG. 7, the arrowheads indicate bases in which polymorphism is observed between alleles.

From these results, it has been confirmed that the Schyzon-like cells derived from the HKN1 strain are haploid cells generated by the meiosis of the diploid HKN1 strain.

In addition, the YFU3 strain isolated from the hot acidic water collected in Yufu-shi was a Cyanidioschyzon-like cell, and a haploid cell.

Hereinafter, diploid cells of the YFU3 strain will be described as "YFU strain (diploid)", haploid Schyzon-like cells derived from the YFU3 strain will be described as "YFU3 strain (haploid)", and the YFU strain (diploid) and the YFU3 strain (haploid) will be collectively described as "YFU3 strain" in some cases. Furthermore, diploid cells of the HKN1 strain will be described as "HKN1 strain (diploid)", haploid Schyzon-like cells derived from the HKN1 strain will be described as "HKN1 strain (haploid)", and the HKN1 strain (diploid) and the HKN1 strain (haploid) will be collectively described as "HKN1 strain" in some cases.

Figures 8A, 8B, 8C, 8D, 8E:
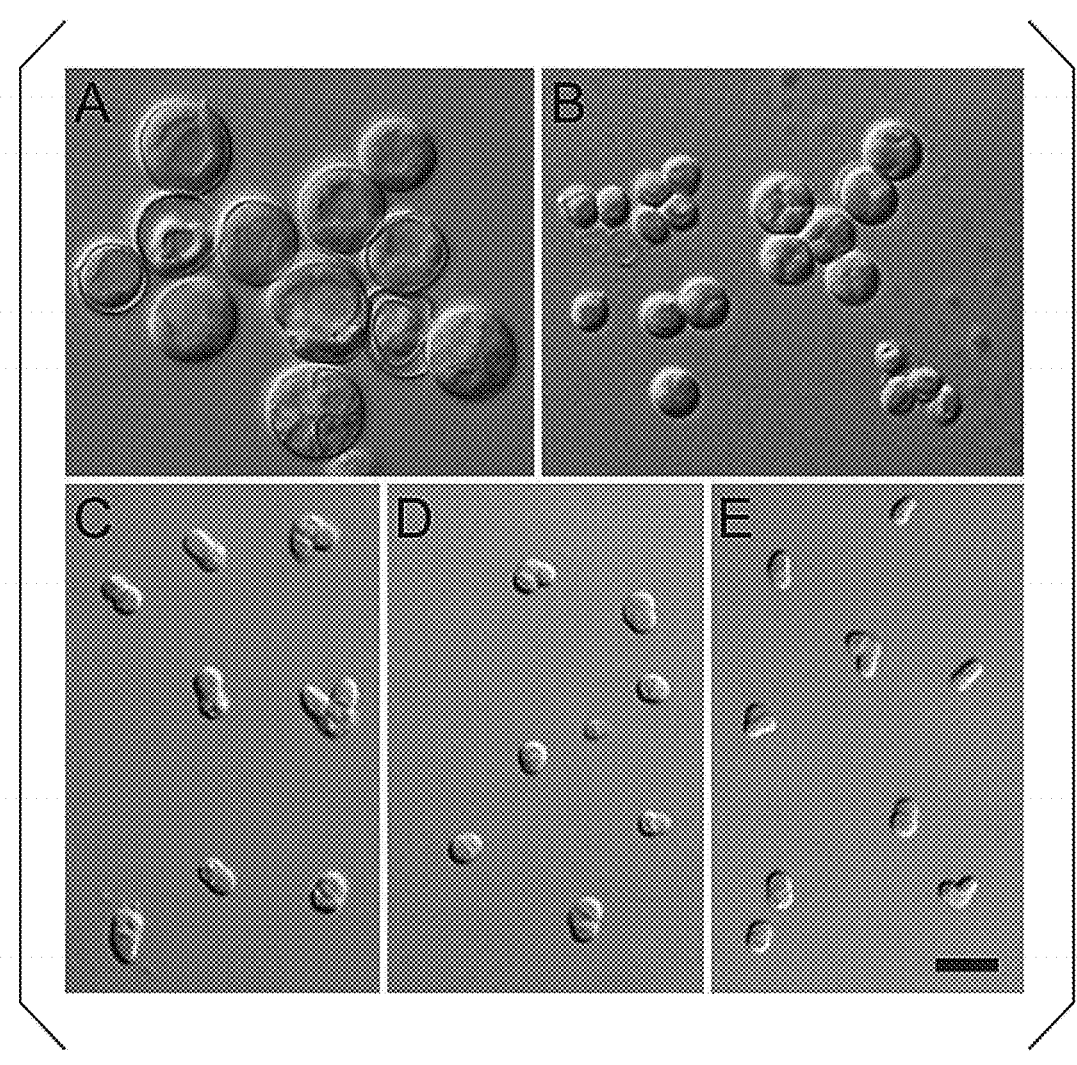
FIGS. 8A-8E show micrographs of algae belonging to Cyanidiophyceae. (A) is a micrograph of Galdieria sulphuraria 074, (B) is a micrograph of Cyanidium caldarium RK-1, (C) is a micrograph of Cyanidioschyzon merolae 10D, (D) is a micrograph of YFU3 (haploid), and (E) is a micrograph of HKN1 (haploid). The scale bar represents 5 μm.

FIG. 8 shows pictures (magnification: 600×) of the YFU3 strain (haploid), the HKN1 strain (haploid), and other cells of Cyanidium observed using a microscope (BX51; Olympus Corporation). FIG. 8(A) is a micrograph of Galdieria sulphuraria 074, FIG. 8(B) is a micrograph of Cyanidium caldarium RK-1, FIG. 8(C) is a micrograph of Cyanidioschyzon merolae 10D, FIG. 8(D) is a micrograph of the YFU3 strain (haploid), and FIG. 8(E) is a micrograph of the HKN1 strain (haploid). The scale bar in FIG. 3 represents 5 m. The Galdieria sulphuraria 074 (FIG. 8A) and the Cyanidium caldarium RK-1 (FIG. 8B) have a rigid cell wall and grow by forming endospores within the mother cell wall. In contrast, it has been confirmed that the YFU3 strain (haploid) (FIG. 8D) and the HKN1 strain (haploid) (FIG. 8E) do not have a rigid cell wall just as the Cyanidioschyzon merolae 10D (FIG. 8C) and grow by two-cell division. Furthermore, both the YFU3 strain (haploid) and the HKN1 strain (haploid) had a cell size of about 2 μm.

(Comparison of Size of Ribosomal DNA ITS1)

The YFU3 strain (haploid), the HKN1 strain (haploid), and the Cyanidioschyzon merolae 10D were compared with each other in terms of the size of the ribosomal DNA ITS1.

DNA was extracted from the cells of the YFU3 strain, the HKN1 strain, and the Cyanidioschyzon merolae 10D, and the ribosomal DNA ITS1 was amplified by PCR. The amplified ITS1 fragment was subjected to agarose gel electrophoresis, and the sizes of ITS1 of the microalgae were compared with each other. The primers used for the amplification of ITS1 are as follows.

```
Forward primer:
                                    (SEQ ID NO: 15)
TAGAGGAAGGAGAAGTCGTAA Reverse primer:
                                    (SEQ ID NO: 16)
TTGCGTTCAAAGACTCGATGATTC
```

Figure 9:
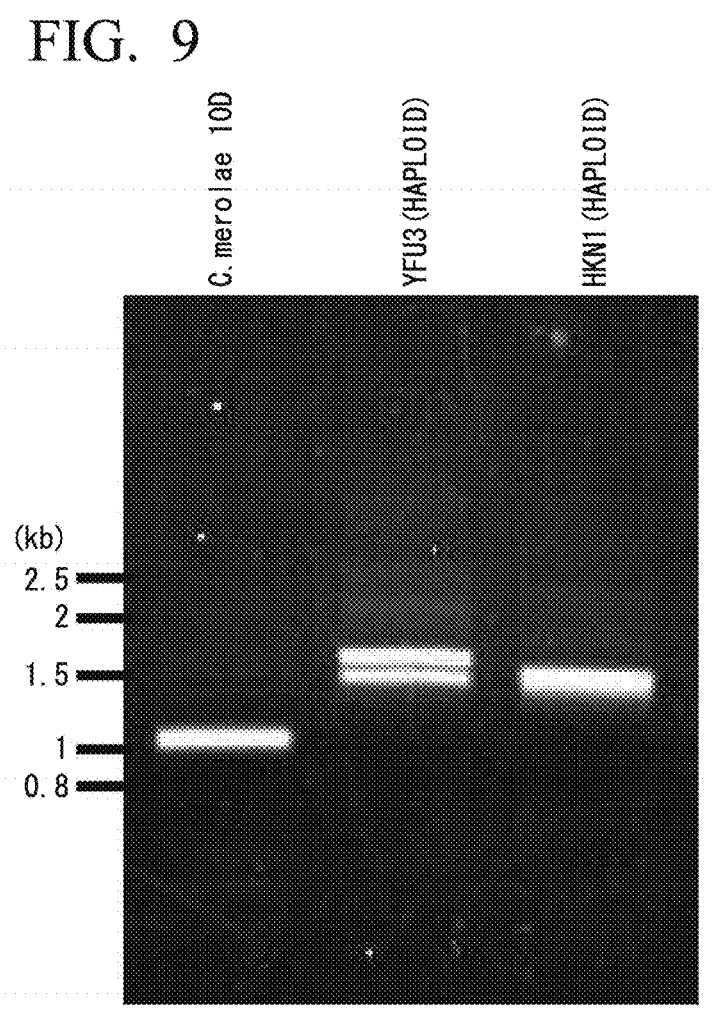

FIG. 9 shows the results of the agarose gel electrophoresis. As shown in FIG. 9, both the YFU3 strain (haploid) and the HKN1 strain (haploid) had an ITS1 size of about 1.5 kb. Furthermore, both the YFU3 strain (haploid) and the HKN1 strain (haploid), had an ITS1 size larger than that of the Cyanidioschyzon merolae 10D.

(Phylogenetic Analysis Based on rbcL Gene Sequence)

By using DNA extracted from cells of the YFU3 strain (haploid) and the HKN1 strain (haploid) as templates, the rbcL gene was amplified by PCR, and the sequence thereof was analyzed. The base sequences of the rbcL genes of the YFU3 strain (haploid) and the HKN1 strain (haploid) are shown in SEQ ID NOS: 1 and 2 respectively.

The sequences of the primers used for the amplification of rbcL are as follows.

```
Forward primer:
                                    (SEQ ID NO: 17)
aaaactttccaaggrccwgc Reverse primer:
                                    (SEQ ID NO: 18)
gcwgttggtgtytchacwaaatc
```

Figure 10:
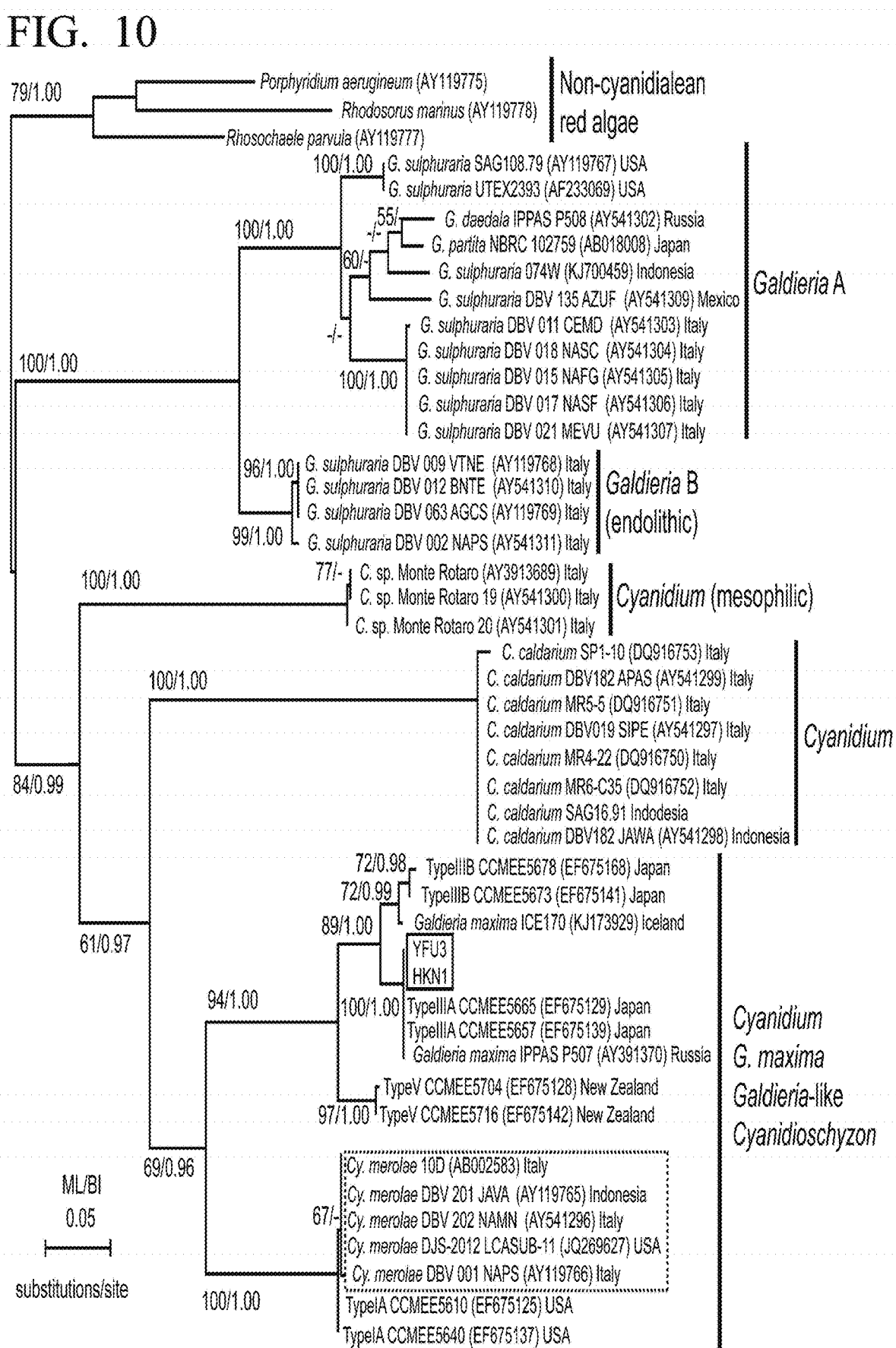
FIG. 10 shows a molecular phylogenetic tree of algae belonging to Cyanidiophyceae based on a chloroplast ribulose 1,5-bisphosphate carboxylase/oxygenase large subunit gene. Near each branch, a local bootstrap value (only a value equal to or greater than 50 is described, left side) determined by the maximum likelihood method and a posterior probability (only a probability equal to or higher than 0.95 is described, right side) determined by the Bayesian method are shown. Known Cyanidioschyzon merolae are boxed in a dotted line, and YFU3 and HKN1 are boxed in a solid line.

Based on the base sequence of the rbcL gene of the YFU3 strain (haploid) and the HKN1 strain (haploid), molecular phylogenetic analysis was performed by the maximum likelihood method. FIG. 10 shows a molecular phylogenetic tree based on the base sequence of the rbcL gene.

From the results of the molecular phylogenetic analysis, it has been determined that the YFU3 strain and the HKN1 strain belong to Cyanidium.

(Culturing of YFU3 Strain (Haploid) and HKN1 Strain (Haploid) in Acidic Hot Spring Drainage Medium)

Whether the YFU3 strain (haploid) and the HKN1 strain (haploid) can be cultured in an acidic hot spring drainage medium was checked. As the acidic hot spring drainage, water from the Tsukahara hot spring or the Tamagawa hot spring was used. By adding 10 mM $(NH_4)_2SO_4$ as a nitrogen source to the acidic hot spring drainage from the Tsukahara hot spring or the Tamagawa hot spring, an acidic hot spring drainage medium was prepared. Alternatively, by adding 10 mM $(NH_4)_2SO_4$ as a nitrogen source and 2 mM $KH_2PO_4$ as a phosphorus source to the acidic hot spring drainage, an acidic hot spring drainage medium was prepared. The YFU3 strain (haploid) or the HKN1 strain (haploid) was cultured with aeration by using 50 mL of the acidic hot spring drainage medium. The cells were cultured for 2 weeks at a culturing temperature of 40° C. under continuous white light (100 mol/m$^2$s).

As a result, the YFU3 strain (haploid) and the HKN1 strain (haploid) could be cultured in any of the acidic hot spring drainage media.

[Example 5]Analysis of Nutrient of Novel Microalgae

By using 5 L of M-Allen medium, the YFU3 strain (haploid) was cultured with aeration. The cells were cultured for 2 weeks at a culturing temperature of 35° C. under continuous white light (500 mol/m²s).

The cells of the YFU3 strain (haploid) cultured as described above were collected by centrifugation, and the component analysis thereof was deputed to Japan Food Research Laboratories. The analytical value per wet weight obtained by the component analysis was divided by 0.248 so as to be converted into a value per dry weight.

Each of the components was analyzed by the method shown in Tables 2 and 3 described above.

Tables 11 and 12 show the results of the component analysis. Table 11 shows the analysis results for amino acids, and Table 12 shows the analysis results for vitamins. In Tables 11 and 12, analytical values published for *Chlorella, Euglena*, and *Spirulina* are also shown for reference.

ing effect, a blood pressure lowering action, a sedative action, and the like. Tomato is known as a food rich in γ-aminobutyric acid, and has been reported to contain γ-aminobutyric acid in an amount of 0.062 g/100 g based on wet weight (Overview on Wide-spreading Dietary Supplements for the Appropriate Use in Dialysis Patients [paper]8 GABA, Clinical Dialysis Vol. 24. No. 13, December 2008). It can be said that the γ-aminobutyric acid content in the YFU strain (haploid) is by no means lower than that in tomatoes.

As shown in Table 12, the YFU3 strain (haploid) tended to be richer in vitamins compared to other algae. Particularly, the content of β-carotene, vitamin C, vitamin E, vitamin K₁, vitamin K₂, and folic acid was higher in the YFU3 strain (haploid) than in other algae.

TABLE 11

| Type of amino acid | Unit (per dry weight of 100 g) | Chlorella[1] | Euglena[2] | Spirulina[3] | Spirulina[4] | YFU3 strain |
|---|---|---|---|---|---|---|
| Isoleucine | g | 2.06 | 1.57 | 3.17 | 3.209 | 2.58 |
| Leucine | g | 4.45 | 3.3 | 5.02 | 4.947 | 5.40 |
| Lysine | g | 3.07 | 2.83 | 2.7 | 3.025 | 3.47 |
| Methionine | g | 1.24 | 0.87 | 2.19 | 1.149 | 1.65 |
| Cystine | g | 0.63 | 0.66 | | 0.662 | 0.81 |
| Phenylalanine | g | 2.59 | 1.79 | 5 | 2.777 | 2.78 |
| Tyrosine | g | 1.79 | 1.73 | | 2.584 | 3.06 |
| Threonine | g | 2.53 | 2 | 2.78 | 2.97 | 3.02 |
| Tryptophan | g | 1.09 | 0.7 | 0.84 | 0.929 | 1.05 |
| Valine | g | 3.11 | 2.57 | 3.48 | 3.512 | 3.59 |
| Arginine | g | 3.51 | 4.19 | 3.6 | 4.147 | 5.48 |
| Histidine | g | 1.05 | 1.06 | 1.09 | 1.085 | 1.17 |
| Alanine | g | 4.27 | 3.03 | 4.11 | 4.515 | 4.80 |
| Aspartic acid | g | 4.82 | 3.83 | 5.47 | 5.793 | 5.81 |
| Glutamic acid | g | 6.01 | 4.9 | 8.02 | 8.386 | 6.73 |
| Glycine | g | 3.01 | 2.03 | 2.85 | 3.099 | 3.02 |
| Proline | g | 2.48 | 2.45 | 2.04 | 2.382 | 2.50 |
| Serine | g | 2.15 | 1.71 | 2.74 | 2.998 | 3.15 |
| Total amount[5] | g | 49.86 | 41.22 | 55.1 | 58.169 | 60.08 |
| γ-Aminobutyric acid | g | — | — | — | — | 0.14 |

[1]Information posted on the website of SUN CHLORELLA CORP.
[2]Physiology and Biochemistry of Euglena, Seizaburo Kitaoka, Gakkai Shuppan Center, 1989
[3]Information posted on the website of DIC LIFETEC Co., Ltd.
[4]USDA Food Composition Databases
[5]Total amount of 18 kinds of amino acids of isoleucine to serine

TABLE 12

| Vitamins | Unit (per dry weight of 100 g) | Chlorella[1] | Euglena[2] | Spirulina[3] | Spirulina[4] | Schyzon |
|---|---|---|---|---|---|---|
| Vitamin A | mg | — | — | 16.2 | — | 13.1 |
| α-carotene | mg | 17.4 | — | — | — | 0 |
| β-carotene | mg | | 7.03 | — | — | 156.8 |
| Vitamin C | mg | 8 | 5 | — | 10.1 | 36 |
| Vitamin E | mg | 3.7 | 23.8 | 9.1 | 5 | 110 |
| Vitamin K₁ | μg | 980 | — | 1080 | 25.5 | 6350 |
| Vitamin K₂ | μg | 0 | — | 80 | — | 1407 |
| Folic acid | μg | 1200 | 990 | 170 | 94 | 2338 |

[1]–[4]Same as in Table 4

As shown in Table 11, it has been revealed that the total amino acid content is higher in the YFU3 strain (haploid) than in other algae conventionally used in foods and the like. Furthermore, the content of each of the amino acids tended to be higher in the YFU3 strain (haploid) than in other algae.

In addition, it has been confirmed that the YFU3 strain (haploid) contains γ-aminobutyric acid. γ-Aminobutyric acid is a substance that functions as an inhibitory neurotransmitter, and has been found to have a brain function improv- Almond is known as a food rich in vitamin E, and has been reported to contain vitamin E in an amount of 30.3 mg/100 g based on wet weight (Standard Tables of Food Composition in Japanese, 2015). Furthermore, Natto is known as a food rich in vitamin K, and has been reported to contain vitamin K in an amount of 600 g/100 g based on wet weight (Standard Tables of Food Composition in Japanese, 2015). It can be said that the content of vitamin E and vitamin K in the YFU strain is higher than those in the foods described above.

From the above results, it has been confirmed that the content of nutrients such as amino acids or vitamins is higher in the YFU3 strain (haploid) than in other algae conventionally used in foods and the like.

[Example 6]Transformation of Novel Microalgae (YFU3 Strain)

(Preparation of Fragment for Transformation)

Fragments for transformation were prepared by the method described in Fujiwara et al. (Front Plant Sci. 2017 Mar. 14; 8: 343). Table 13 shows the primers used for preparing the fragments for transformation. Hereinafter, the primers used will be described using Primer No. described in Table 13.

a DNA fragment was amplified by PCR, thereby preparing a CAT vector for transforming Cyanidioschyzon merolae.

<Preparation of CAT Vector for Transforming Novel Microalgae>

By using the plasmid pD18 prepared as above as a template and using primer set No. 11/12, a DNA fragment was amplified by PCR, thereby preparing a CAT vector for transforming novel microalgae.

(Transformation)

The cells were transformed by a method obtained by modifying the method described in Ohnuma M et al (Plant Cell Physiol. 2008 January; 49 (1): 117-20.). The Cyanidioschyzon merolae 10D and the YFU3 strain (haploid) were used as parent strains for transformation. The cells of each of the parent strains were diluted with 50 mL of an MA2U medium (MA2 medium containing 0.5 mg/mL uracil) so as to yield a concentration of OD750=0.3. The cells were cultured for 19 hours with aeration (600 mL/ambient air/

TABLE 13

| No. | Primer | Sequence (5'→3') | SEQ ID NO: |
|---|---|---|---|
| 1 | APCC(1)Fapc | cttcgttcgttgaccATGTTCGTTCAGACCAGTTTCTTT | 19 |
| 2 | APCC(180)R | ATCATTCGCAACGCCAGATG | 20 |
| 3 | B-TUB(+1) | TAAACTAGCTATTTATCTGGTACATATCATTCAT | 21 |
| 4 | B-TUB(+200)Rd184 | tcgctgagcggtttcACACTTTTTGCCTGCACAAGTTTTCGTAC | 22 |
| 5 | CAT(1)Fapcc | ggcgttgcgaatgatATGAACTTTAATAAAATTGATTTAGACAATTGG | 23 |
| 6 | CAT(650)taaRbt | taaatagctagtttaTAAAAGCCAGTCATTAGGCCTATC | 24 |
| 7 | APCC(-1)R | GGTCAACGAACGAAGAAACACAGAGAACAAAGATAT | 25 |
| 8 | D184(+28)F | GAAACCGCTCAGCGACCAAGCGAC | 26 |
| 9 | D184(1270)F | ACACGAATCACACGGTGCTG | 27 |
| 10 | D184(+1448)R | TTGCCGATAACGCAGAAGAGA | 28 |
| 11 | APCC(-600)F | CGACGAGAACGTATAAGGAGTGCGCACG | 29 |
| 12 | B-TUB(+200)R | ACACTTTTTGCCTGCACAAGTTTTCGTACG | 30 |

The lower cases represent an adapter sequence of In-Fusion reaction.

<Preparation of CAT Vector for Transforming of Cyanidioschyzon Merolae>

By using the genomic DNA of the Cyanidioschyzon merolae 10D as a template and using primer set No. 1/2, 1 to 180 nucleotides encoding a chloroplast transition sequence (60 amino acids) in APCC ORF (CMO250C) of Cyanidioschyzon merolae were amplified by PCR. Furthermore, by using the genomic DNA of the Cyanidioschyzon merolae 10D as a template and using primer set No. 3/4, a downstream nucleotide (200 bp, βt3') of β-tubulin ORF of the Cyanidioschyzon merolae was amplified by PCR. By using a chloramphenicol acetyltransferase gene of pC194 (pC194, Gene ID: 4594904; *Staphylococcus aureus*) as a template and using primer set No. 5/6, CAT ORF was amplified by PCR. By using an InFusion Cloning Kit (Takara Bio Inc.), the sequence encoding a chloroplast transition sequence of APCC, CAT ORF, and the downstream sequence of β-tubulin were cloned into pD184-O250-EGFP-URA$_{Cm-Cm}$ (Fujiwara et al., PLoS One. 2013 Sep. 5; 8 (9): e73608) amplified using primer set No. 7/8, thereby constructing a plasmid pD184-CAT. By using a plasmid pD18 as a template and using primer set No 9/10, min) under continuous light (100 mol/m²s). Then, Tween-20 was added to the culture solution such that the final concentration became 0.002%, and the cells were collected by centrifugation (2,000 g, 5 minutes). The collected cells were suspended in 270 μL of an MA2U medium. Transformation was performed according to the protocol using polyethylene glycol (PEG).

PEG4000 (Sigma-Aldrich Co. LLC., #81240, 0.6 g) was dissolved in 450 μL of an MA2U medium (95° C., 10 minutes), thereby preparing a 60% (w/v) PEG4000 solution. Subsequently, the PEG 4000 solution was kept at 42° C. on a heat block until used.

Each of the CAT vectors (4 μg) for transformation prepared as above was dissolved in 90 μL of water. The vector solution (90 μL), 10 μL of a 10×TF solution (400 mM (NH$_4$)$_2$SO$_4$, 40 mM MgSO$_4$, 0.3% H$_2$SO$_4$), and 100 μL of the PEG 4000 solution were mixed together in a 1.5 mL tube by means of pipetting. Then, 25 μL of the cell suspension was added to 200 μL of a TF-CAT vector-PEG4000 mixed solution, stirred by being flipped upside down three to four times, and immediately moved to 40 mL of an MA2U medium. The cells were cultured for 1 day with aeration (300 mL ambient air/min) under continuous light (100 mol/m²s). Thereafter, the cells were collected by centrifugation (1,500 g, 5 minutes) and suspended in 2 mL of an MA2U medium. The cells were cultured for 2 to 3 days in a 24-well plate (TPP Techno Plastic Products AG) under the conditions of continuous light, 42° C., and 5% $CO_2$. Subsequently, chloramphenicol (CP) was added to the culture solution, the cells were cultured for 10 days, and CP-resistant transformants were selected. The CP resistant transformants were diluted stepwise by being washed with a CP-free MA2U medium, and spotted on a starch bed on an MA2U gellan gum plate. The starch bed and the MA2U gellan gum plate were prepared by a method obtained by adding slight modifications (Fujiwara et al., PLoS One. 2013 Sep. 5; 8(9): e73608) to the method described in Imamura S et al (Plant Cell Physiol. 2010 May; 51(5):707-17). The plate was cultured for 2 weeks in a 5% $CO_2$ incubator until colonies appeared. According to the method described in Fujiwara et al. (PLoS One. 2013 Sep. 5; 8 (9): e73608), the colonies were moved to a starch bed on a new MA2U medium plate.

(Evaluation of Chloramphenicol (CP) Resistance)

After being transformed as described above, the cells were cultured in an MA2 liquid medium supplemented with CP so as to select CP-resistant transformants of Cyanidioschyzon merolae 10D and the YFU3 strain (haploid). In order to evaluate CP-resistant concentration of each of the CP-resistant transformants, a wild-type strain (WT) and the transformant (TF) were cultured for 10 days in an MA2 liquid media containing CP at various concentrations (0.50, 100, 150, 200, and 250 μg/mL).

Figure 11:
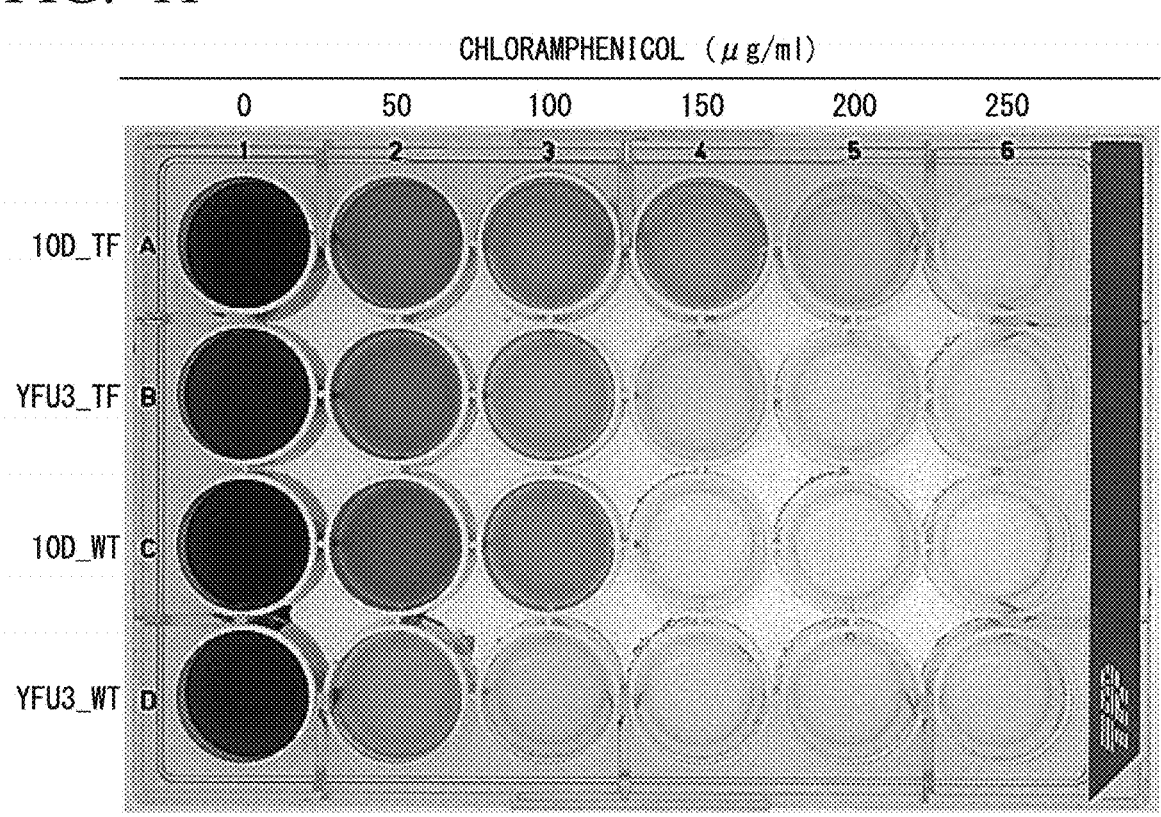
FIG. 11 shows the chloramphenicol resistance of chloramphenicol-resistant transformants of YFU3 (haploid) and Cyanidioschyzon merolae 10D prepared in Example 6.

The results are shown in FIG. 11. In FIG. 11, 10D_TF and 10D_WT represent the CP-resistant transformant of the Cyanidioschyzon merolae 10D and the wild-type strain respectively. YFU3_TF and YFU3 WT represent the CP-resistant transformant of the YFU3 strain (haploid) and the wild-type strain respectively. As shown in FIG. 11, in both the Cyanidioschyzon merolae 10D and the YFU3 strain (haploid), the CP-resistant transformant exhibited higher CP concentration resistance compared to the wild-type strain.

In addition, in order to check whether the CAT gene has been introduced into the cells cultured as shown in FIG. 11, primers were designed for the 5' terminal sequence of the chloroplast transition sequence of APCC and for the 3' terminal sequence of CAT ORF. The sequences of the primers are as follows.

```
APCC (1) forward primer:
                                  (SEQ ID NO: 31)
ATGTTCGTTCAGACCAGTTTCTTT CAT (650) reverse primer:
                                  (SEQ ID NO: 32)
TAAAAGCCAGTCATTAGGCCTA
```

In FIG. 11, CP-resistant transformant cells (TF_0, TF_150) of the Cyanidioschyzon merolae 10D cultured in CP at 0 μg/mL or 150 μg/mL and the CP-resistant transformant cells (TF_0, TF_100) of the YFU3 strain (haploid) cultured in CP at 0 μg/mL or 100 μg/mL were collected and subjected to PCR by using the above primer set. Then, agarose gel electrophoresis was performed to check where or not amplified fragments generated by PCR are present.

Figure 12:
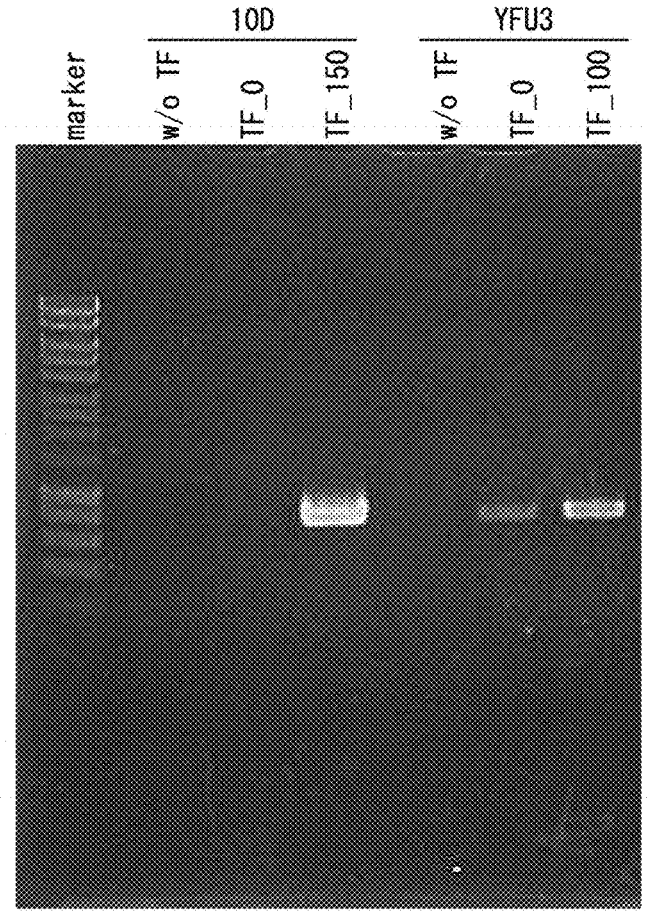
FIG. 12 shows the results of PCR performed to confirm whether a CAT gene has been inserted into the genome of the chloramphenicol-resistant transformants of YFU3 (haploid) and Cyanidioschyzon merolae 10D prepared in Example 6.

The results are shown in FIG. 12. In FIG. 12, "w/o TF" represents a cell that has not been subjected to transformation (wild-type strain). As shown in FIG. 12, in the CP-resistant transformant of the YFU3 strain (haploid), even though the cells were cultured in CP at a concentration of 0 μg/mL and at a concentration of 100 μg/mL, the amplified fragment of the CAT gene was checked. In the Cyanidioschyzon merolae, the amplified fragment of the CAT gene was checked in the cells cultured in CP at a concentration of 150 μg/mL, but no amplified fragment of the CAT gene was checked in the cells cultured in CP at a concentration of 0 μg/mL. It is considered that in a case where the Cyanidioschyzon merolae is cultured in the absence of CP, the introduced CAT gene may be eliminated.

The above results show that the YFU3 strain (haploid) can be transformed just as the Cyanidioschyzon merolae.

[Example 7]Transformation of Novel Microalgae (HKN1 Strain)

(Preparation of Fragment for Transformation)

Table 14 shows the primers used for preparing fragments for transformation. Hereinafter, the primers used will be described using Primer No. shown in Table 14.

TABLE 14

| No. | Primer | Sequence (5'→3') | SEQ ID NO: |
|---|---|---|---|
| 1 | URA5.3 (-2500) F | CGGTACCCGGGGATCGTCTCCTCTCGAAAAATGATTAC | 63 |
| 2 | URA5.3 (-501) R | CGACTCTAGAGGATCTGTGAAGACTATGTCGGTGTTC | 64 |
| 3 | APCC promoter F | CGGTACCCGGGGATCCATTCCCCTATTTCATGAATG | 65 |
| 4 | APCC promoter R | GACTCTTTCGGCGTTATTTGCG | 66 |
| 5 | mVenus EcoRV F | AACGCCGAAAGAGTCgatatcATGGTTAGCAAGGGCGAAG | 67 |
| 6 | mVenus NotI R | CCATGAAATGCAAGTgcggccgcTCACTTATACAGTTCATCCATACCC | 68 |
| 7 | Btub 3'UTR F | ACTTGCATTTCATGGCGAGGC | 69 |
| 8 | Btub 3'UTR R | CGACTCTAGAGGATCTCAAGCTCGGAAGAGAAGCTTC | 70 |
| 9 | CPCC promoter F | CGGTACCCGGGGATCTCACAGCATATGTCAAGAGCCTGC | 71 |
| 10 | CPCC promoter R | GTTTGCAGTGTTTCCGATCAGAGTTAG | 72 |
| 11 | Tp of POP F | GGAAACACTGCAAACATGCGGTTAGGCGTAGGGTC | 73 |

TABLE 14-continued

| No. | Primer | Sequence (5'→3') | SEQ ID NO: |
|---|---|---|---|
| 12 | Tp of POP R | CTTGTTAAAGTTCATAGCCGAACGGCGGGCG | 74 |
| 13 | CAT F | ATGAACTTTAACAAGATTGACCTGG | 75 |
| 14 | CAT R | AGCGCACATACAAACTCACAGGAGCCAGTCGTTGG | 76 |
| 15 | UBQ 3'UTR F | GTTTGTATGTGCGCTTCGTAAAGC | 77 |
| 16 | UBQ 3'UTR R | CGACTCTAGAGGATCTCTGACCTAAGACCACACACCTAG | 78 |
| 17 | pmVenus F | TGATTCAGAAAGAAACATTCCCCTATTTCATG | 79 |
| 18 | pmVenus R | TGACATATGCTGTGATCAAGCTCGGAAGAGAAGCTTC | 80 |
| 19 | pCAT F | TCACAGCATATGTCAAGAGCCTGC | 81 |
| 20 | pCAT R | ACTGTATTTCGAATGTCTGACCTAAGACCACACACCTAG | 82 |
| 21 | URA5.3 (-1501) F | CATTCGAAATACAGTGTTTCGTG | 83 |
| 22 | URA5.3 (-1502) R | TTTCTTTCTGAATCAAACGAGACG | 84 |
| 23 | M13 F | GTAAAACGACGGCCAGT | 85 |
| 24 | M13 R | CAGGAAACAGCTATGAC | 86 |

<Preparation of CAT Vector for Transforming Novel Microalgae>

The construct for introducing genes into the upstream of the URA5.3 gene was prepared as below. By using the genomic DNA of the HKN1 strain as a template and using primer set No. 1/2, a DNA fragment of the upstream sequence (-2500 to −501) of the URA5.3 gene was amplified by PCR. Then, by using the In-Fusion HD Cloning Kit, the fragment amplified by PCR was subcloned into pUC19. The resulting vector will be referred to as pURA5.3up vector.

Subsequently, by using the genomic DNA of the HKN1 strain as a template and using primer set No. 3/4, a DNA fragment of the upstream sequence (-500 to −1) of APCC was amplified by PCR. Furthermore, by using primer set No. 5/6, mVenus ORF (synthesized by Integrated DNA Technologies) was amplified by PCR. In addition, by using the genomic DNA of the HKN1 strain as a template and using primer set No. 7/8, a DNA fragment of the downstream sequence (+1 to +250) of β-tubulin was amplified by PCR. By using the In-Fusion HD Cloning Kit, the three fragments amplified by PCR were subcloned into pUC19. The resulting vector will be referred to as pmVenus vector.

Thereafter, by using the genomic DNA of the HKN1 strain as a template and using primer set No. 9/10, a DNA fragment of the upstream sequence (-500 to −1) of CPCC was amplified by PCR. Furthermore, by using the genomic DNA of the Cyanidioschyzon merolae 10D as a template and using primer set No. 11/12, a DNA fragment of the organelle transition sequence of POP was amplified by PCR. In addition, by using primer set No. 13/14, CAT ORF (synthesized by Integrated DNA Technologies) was amplification by PCR. Moreover, by using the genomic DNA of the HKN1 strain as a template and using primer set No. 15/16, a DNA fragment of the downstream sequence (+1 to +250) of ubiquitin was amplified by PCR. By using the In-Fusion HD Cloning Kit, the four fragments amplified by PCR were subcloned into pUC19. The resulting vector will be referred to as pCAT vector.

Figure 13:
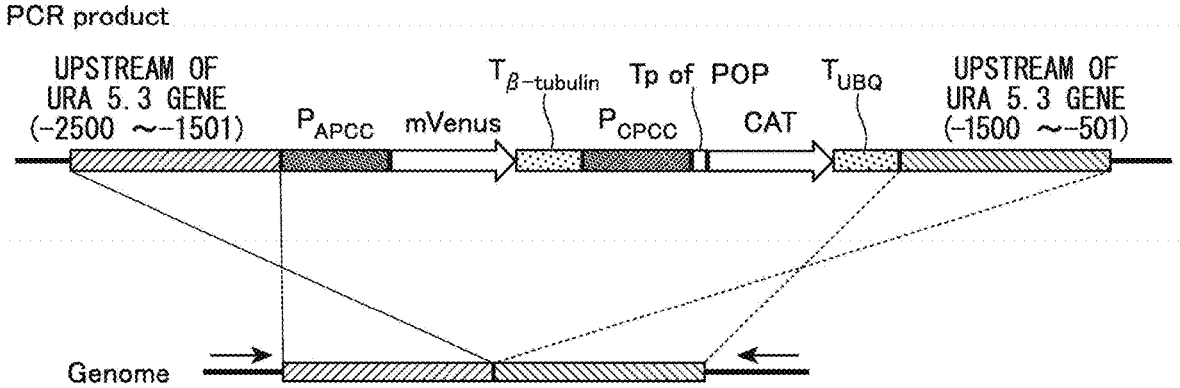
FIG. 13 shows the construct of a CAT vector for transformation used in Example 7 (upper figure: PCR product) and the insertion position of the vector in the genome of HKN1 (haploid) (lower figure: Genome). In the lower figure (Genome), the arrows indicate the position of a primer used to check whether an mVenus-CAT gene has been inserted into the genome of the chloramphenicol-resistant transformant.

Subsequently, by using the pmVenus vector as a template and using primer set No. 17/18, a DNA fragment was amplified by PCR. Furthermore, by using the pCAT vector as a template and using primer set No. 19/20, a DNA fragment was amplified by PCR. In addition, by using primer set No. 21/22, the pURA5.3up vector was amplified by PCR. Then, by using the In-Fusion HD Cloning Kit, the amplified fragment of the pmVenus vector and the amplified fragment of the pCAT vector were cloned into the pURA5.3up vector amplified as described above. By using the resulting pURA5.3up-mVenus-CAT vector as a template and using primer set No. 23/24, a DNA fragment was amplified by PCR. The amplified DNA fragment was used as a CAT vector for transformation. The structure of the CAT vector for transformation is shown in FIG. 13 as PCR Product.

(Transformation)

The cells were transformed by a method obtained by modifying the method described in Ohnuma M et al (Plant Cell Physiol. 2008 January; 49 (1): 117-20.). The HKN1 strain (haploid) was used as a parent strain for transformation. The cells of the parent strain were diluted with 50 mL of an MA2U medium (MA2 medium containing 0.5 mg/mL uracil) so as to yield a concentration of OD750=0.3. The cells were cultured for 60 hours with aeration (600 mL ambient air/min) in a light-dark cycle (12L:12D) under light (50 mol/m$^2$s) at a temperature of 42° C. Then, Tween-20 was added to the culture solution such that the final concentration became 0.002%, and the cells were collected by centrifugation (2,000 g, 5 minutes). The collected cells were suspended in 270 μL of an MA2U medium. Transformation was performed according to the protocol using polyethylene glycol (PEG). PEG4000 (Sigma-Aldrich Co. LLC., #81240, 0.6 g) was dissolved in 450 μL of an MA2U medium (95° C., 10 minutes), thereby preparing a 60% (w/v) PEG4000 solution. Subsequently, the PEG4000 solution was kept at 42° C. on a heat block until used.

The CAT vector (4 μg) for transformation was dissolved in 90 μL of water. The vector solution (90 μL), 10 μL of the 10×TF solution (400 mM $(NH_4)_2SO_4$, 40 mM $MgSO_4$, 0.3% $H_2SO_4$), and 100 µL of the PEG4000 solution were mixed together in a 1.5 mL tube by means of pipetting, thereby preparing a TF-CAT vector-PEG 4000 mixed solution. Then, 25 µL of the cell suspension was added to 200 µL of the TF-CAT vector-PEG4000 mixed solution, stirred by being flipped upside down three to four times, and immediately moved to 10 mL of an MA2U medium. The cells were cultured for 2 days in a static state under continuous light (20 µmol/m²s) at a temperature of 42° C. Thereafter, the cells were collected by centrifugation (1,500 g, 5 minutes) and suspended in 1 mL of the Tsukahara mineral spring medium or 1 mL of a modified MA medium. The cell suspension (100 µL) was added to 1 mL of the Tsukahara mineral spring medium or the modified MA medium containing CP at 100 µg/mL, and the cells were cultured for 7 days in a static state in a 24-well plate (TPP Techno Plastic Products AG) under the conditions of continuous light (20 µmol/m²s), 42° C., and 3% $CO_2$. A green portion, which had become darker, was added to 1 mL of a new Tsukahara mineral spring medium or modified MA medium containing CP at 100 µg/mL, the cells were further cultured for 7 days in a static state, and CP-resistant transformants were selected. By using the Pasteur pipette with a sharp tip, the CP-resistant transformant cells were isolated one by one under an inverted microscope (CKX41; Olympus Corporation), and cultured in a static state in 1 mL of the Tsukahara mineral spring medium or the modified MA medium.

Table 15 shows the composition of the modified MA medium.

TABLE 15

| Modified MA medium | |
| --- | --- |
| $(NH_4)_2SO_4$ | 2.64 g |
| $KH_2PO_4$ | 0.54 g |
| $MgSO_4•7H_2O$ | 0.5 g |
| $CaCl_2•2H_2O$ | 0.14 g |
| A2 trace element | 2 mL |
| Distilled water | 998 mL |

Adjusted to pH 1.2 by using sulfuric acid
Autoclaving followed by addition of 1.39 g of $FeSO_4•7H_2O$

| A2 trace element | |
| --- | --- |
| $H_3BO_4$ | 2.85 g |
| $MnCl_2•4H_2O$ | 1.8 g |
| $ZnCl_2$ | 0.105 g |
| $Na_2MoO_4•2H_2O$ | 0.39 g |
| $CoCl_2•6H_2O$ | 40 mg |
| $CuCl_2•2H_2O$ | 43 mg |
| Distilled water | 1,000 mL |

(Checking Transformant)

Primers were designed to check whether the mVenus-CAT gene had been introduced into the target site in the cells of the CP-resistant transformant that had been isolated and cultured (see FIG. 13; the approximate location of the primers are indicated by the arrows in the lower figure (Genome) of FIG. 13). The sequences of the primers are as follows.

Forward primer:
(SEQ ID NO: 87)
CATTGCACAGCAATGAAAAGCG

-continued

Reverse primer:
(SEQ ID NO: 88)
ATCGAAACTGCGTAGATAGTGTCGG

The cells of the CP transformant were collected. By using the primer set described above, PCR was performed, and agarose gel electrophoresis was carried out.

Figure 14:
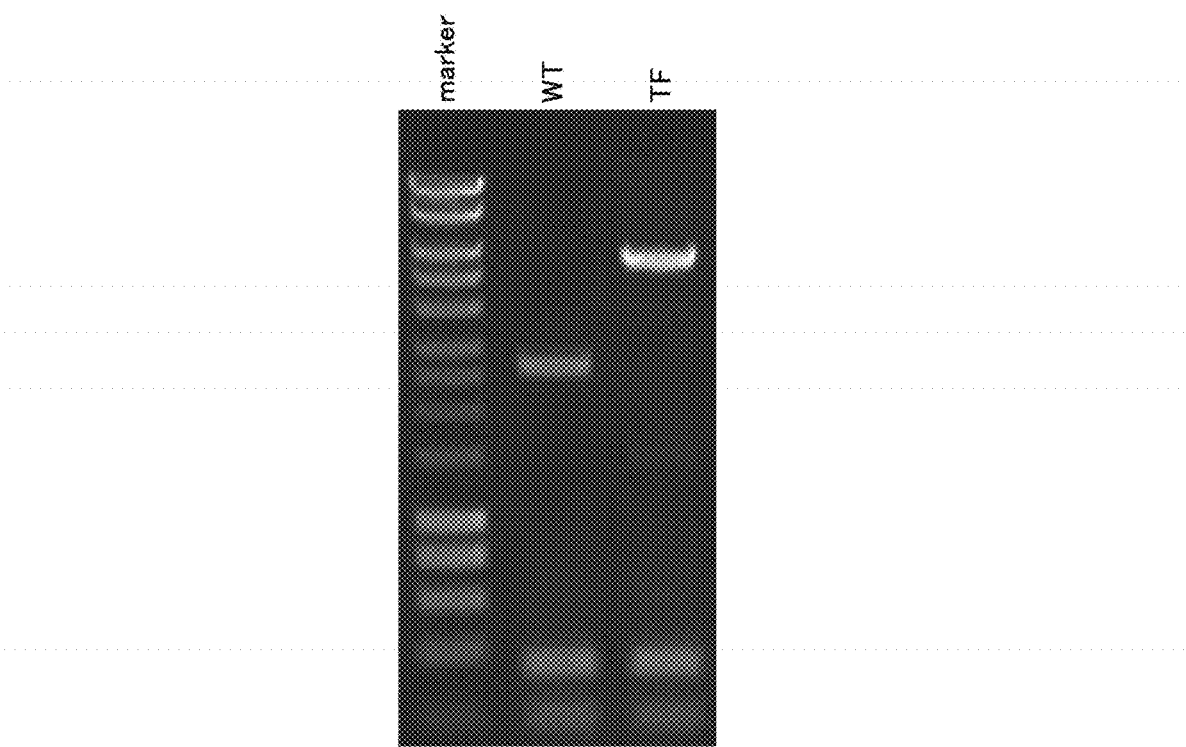
FIG. 14 shows the results of PCR and agarose gel electrophoresis performed to confirm whether the mVenus-CAT gene has been inserted into the genome of the chloramphenicol transformant prepared in Example 7.

The results are shown in FIG. 14. An amplified fragment was observed at about 2.5 kb in the wild-type strain (WT). In contrast, an amplified fragment was detected at about 5.5 kb in the CP-resistant transformant (TF). From this result, it has been confirmed that the mVenus-CAT gene has been inserted into the target site (see FIG. 13) in the transformant (TF). The above result shows that gene targeting can be performed on the HKN1 (haploid).

Figure 15:
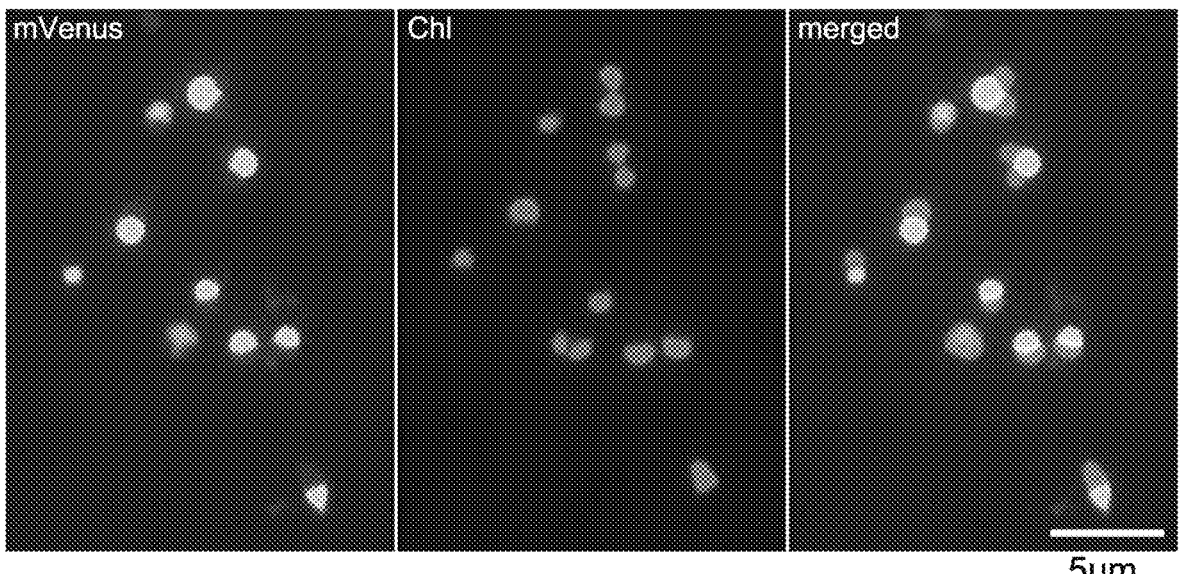
FIG. 15 shows fluorescence micrographs of the chloramphenicol transformant prepared in Example 7. The left figure (mVenus) is a fluorescence micrograph in which the fluorescence of mVenus is detected, the middle figure (Chl) is a fluorescence micrograph in which the autofluorescence of the chloroplast is detected, and the right figure (merged) is an image obtained by merging the two fluorescence micrographs.

Furthermore, the CP-resistant transformant was observed using a fluorescence microscope so as to check whether green fluorescence from mVenus is observed. The results are shown in FIG. 15. In FIG. 15, the left figure (mVenus) is a fluorescence micrograph showing the detected fluorescence of mVenus, the middle figure (Chl) is a fluorescence micrograph showing the detected autofluorescence of the chloroplast, and the right figure (merged) is an image obtained by merging the two fluorescence micrographs. As shown in FIG. 15, in the CP-resistant transformant, mVenus was expressed in the cytoplasm, and green fluorescence was detected. The above results show that the HKN1 (haploid) can express a foreign gene.

[Example 8] Cell Rupturing Treatment for YFU3 Strain and HKN1 Strain (Drying and Swelling Treatment for Algal Cells)

The YFU3 strain (haploid), the HKN1 strain (haploid), and the HKN1 strain (diploid) were cultured in the same manner as in Example 5, and 1 mL of the culture solution was subjected to centrifugation (1,500×g, 2 minutes). The supernatant obtained after the centrifugation was discarded, the precipitate of the algal cells was suspended in an isotonic solution (10% sucrose, 20 mM HEPES, pH 7.0) and subjected to centrifugation (1,500×g, 3 minutes), and the algal cells were washed. The supernatant obtained after the centrifugation was discarded, and the precipitate of the algal cells was left in a refrigerator (4° C.) for 3 days so as to dry the algal cells.

Three days later, the algal cells were suspended in 45 µL of an isotonic solution (10% sucrose, 20 mM HEPES, pH 7.0), and subjected to centrifugation (1,500×g, 3 minutes), and centrifugal supernatant and precipitate were collected.

Furthermore, Cyanidium caldarium RK-1 as a control of algae having a rigid cell wall and Cyanidioschyzon merolae 10D as a control of algae having no rigid cell wall were cultured and subjected to the same drying and swelling treatment as that described above, and centrifugal supernatant and precipitate were obtained.

(SDS-Polyacrylamide Electrophoresis (SDS-PAGE))

In order to prepare a sample for SDS-PAGE, 15 µL of a 4×SDS-PAGE sample buffer was added to the centrifugal supernatant. Furthermore, 60 µL of 1×SDS-PAGE sample buffer was added to the centrifugal precipitate. SDS-PAGE was performed on the supernatant sample and the precipitate sample prepared as above. The gel after SDS-PAGE was stained with coomassie brilliant blue, and proteins in the centrifugal supernatant and precipitate were checked.

Figure 16:
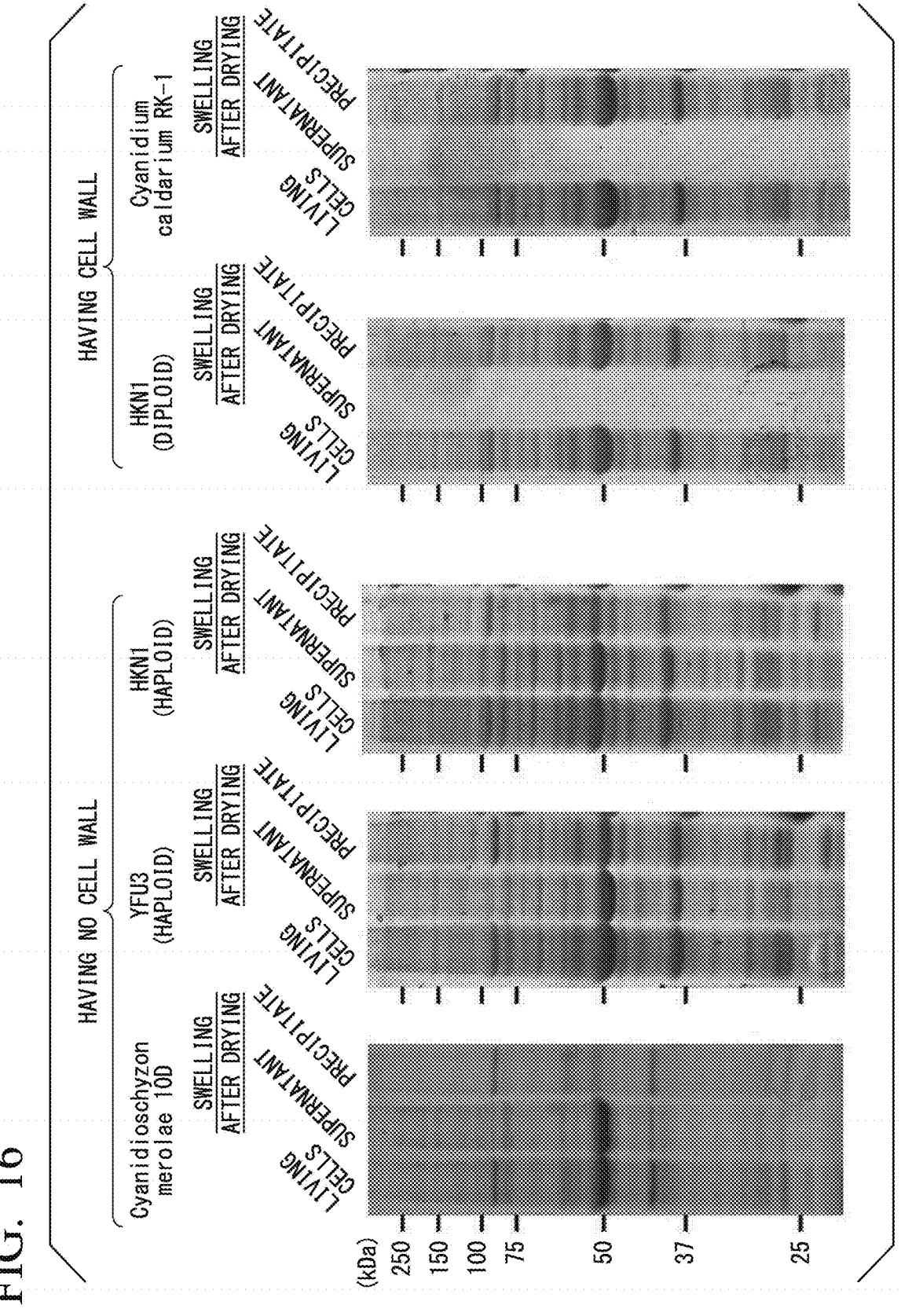
FIG. 16 shows the results of SDS-polyacrylamide electrophoresis performed on centrifugal supernatants and centrifugal precipitates which are obtained by performing a drying and swelling treatment on algae having no rigid cell wall and algae having a cell wall and performing centrifugation on cell suspensions obtained after the swelling treatment.

FIG. 16 shows the results. In the YFU3 strain (haploid), the HKN1 strain (haploid), and the Cyanidioschyzon merolae 10D, a plurality of kinds of proteins were detected in both the supernatant and the precipitate obtained after the drying and swelling treatment. From this result, it has been confirmed that the YFU3 strain (haploid), the HKN1 strain (haploid), and the Cyanidioschyzon merolae 10D undergo cell rupture by the drying and swelling treatment. On the other hand, in the HKN1 strain (diploid) and the Cyanidium Caldarium RK-1, no protein was detected in the supernatant obtained after the drying and swelling treatment. This result shows that the HKN1 strain (diploid) and the Cyanidium Caldarium RK-1 do not undergo cell rupture by the drying and swelling treatment.

[Example 9]Preparation of Diploid by Combining Haploids (Combining HKN1 Strains (Haploids))

Figure 17A:
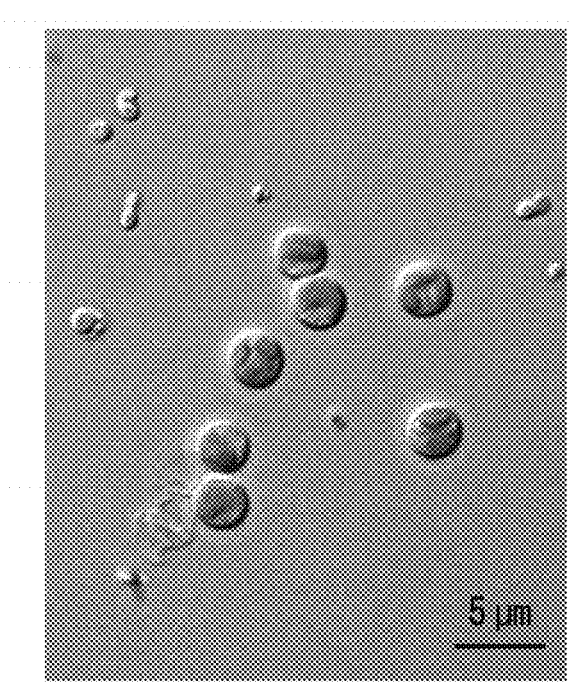
FIG. 17A is a micrograph of diploid-like cells having a rigid cell wall that are obtained by crossing HKN1 cells (haploids).

No. 1 and No. 5 strains of the HKN1 strain (haploid) were mixed together and cultured in an MA medium for 3 weeks under the culture conditions of 40° C., light at 50 mol/m$^2$s, a light-dark cycle (12L:12D), and 2% $CO_2$. After being cultured for 3 weeks, the cells were further subcultured (diluted 20×) in a new medium for 1 week. Thereafter, the algal cells were observed using a microscope. As a result, diploid-like cells having a rigid cell wall were checked (FIG. 17A).

The diploid-like cells were collected and stained with DAPI so as to quantify the fluorescence intensity. For comparison, the HKN1 strain (haploid) was also stained with DAPI. The results are shown in FIG. 17B.

Figure 17B:
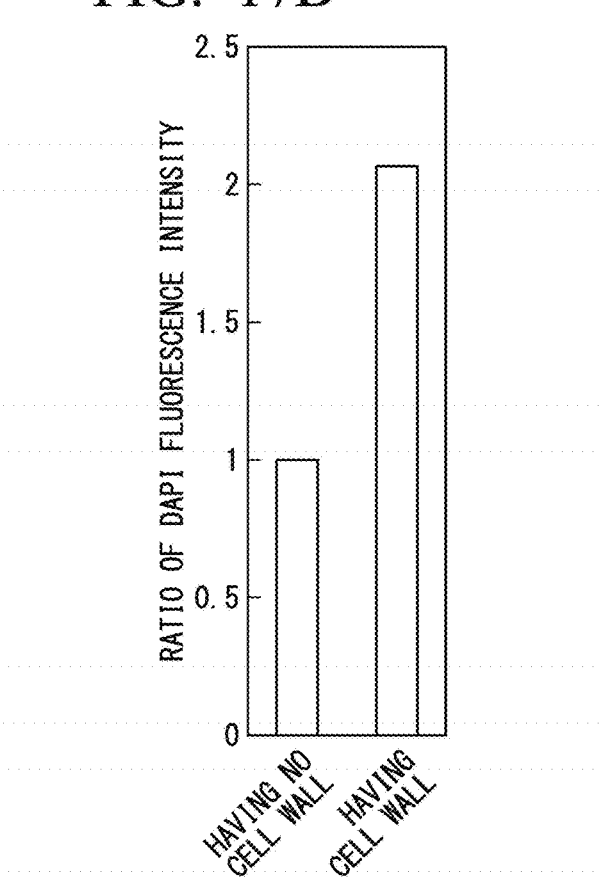
FIG. 17B shows the results of DAPI staining performed on the diploid-like cells having a rigid cell wall and HKN1 (haploid).

As shown in FIG. 17B, the fluorescence intensity of the diploid-like cells was twice the fluorescence intensity of the haploid strain. From this result, it has been confirmed that the diploid-like cells are diploids. From the above results, it has been revealed that by mixing together and culturing haploid cells, diploid cells can be prepared.

(Combining YFU3 Strains (Haploids))

The YFU3 strain (haploid) was subjected to the same operation as that described above. As a result, the emergence of diploid cells was confirmed by an optical microscope.

[Example 10]Preparation of Haploid Cells of Algae Belonging to Galdieria (Creation of Cells Having No Cell Wall: G. Sulphuraria)

(Method (a))

The Tsukahara mineral spring medium (Hirooka et al. 2016 Front in Microbiology) or a modified MA medium (1 mL) was put into a 24-well plate, about 10 cells of Galdieria sulphuraria SAG108.79 were added to each of the wells, and the cells were cultured for 1 week under light at 50 mol/m$^2$s at a temperature of 42° C. in 2% $CO_2$. In this medium, both the tadpole-like cells and the round cells were present. Under a microscope, the tadpole-like cells were isolated using a Pasteur pipette with a sharp tip, and these cells were further cultured in an MA medium under light at 50 μE/m$^2$s at 42° C. in 2% $CO_2$.

(Method (b)) (Three-Stage Culturing)

The Galdieria sulphuraria SAG108.79 was cultured in an MA medium until the strain reached a plateau phase, a cell population was taken out of the culture solution and diluted 100×, and the cells were further subcultured in an MA medium. After 3 days of culturing, tadpole-like cells appeared. Therefore, by using a Pasteur pipette with a sharp tip, the tadpole-like cells were isolated from the culture solution while being observed under a microscope. The isolated cells were further cultured in an MA medium at 42° C. under light at 50 μE/m$^2$s in 2% $CO_2$.

Figure 18A:
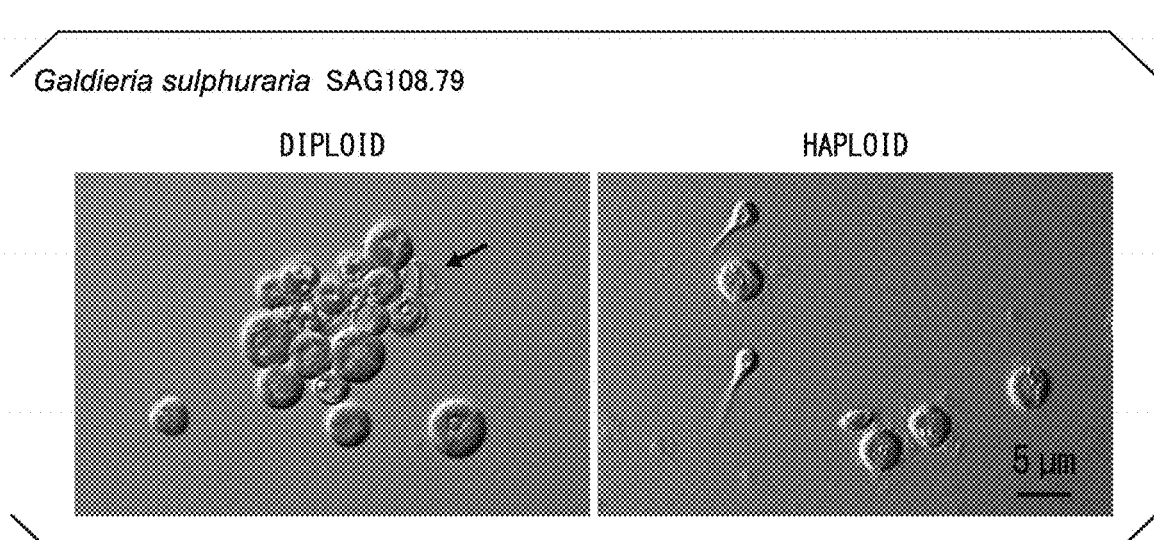
FIG. 18A shows a micrograph (left figure) of normal cells (diploids) of Galdieria sulphuraria SAG108. 79 and a micrograph (right figure) of the same strain in the form of cells having no rigid cell wall.

FIG. 18A shows the normal cells of Galdieria sulphuraria SAG108.79 (left figure) and the cells having no rigid cell wall checked after the culturing of the normal cells (right figure).

(Creation of Cells Having No Rigid Cell Wall: G. partita)

Figure 18B:
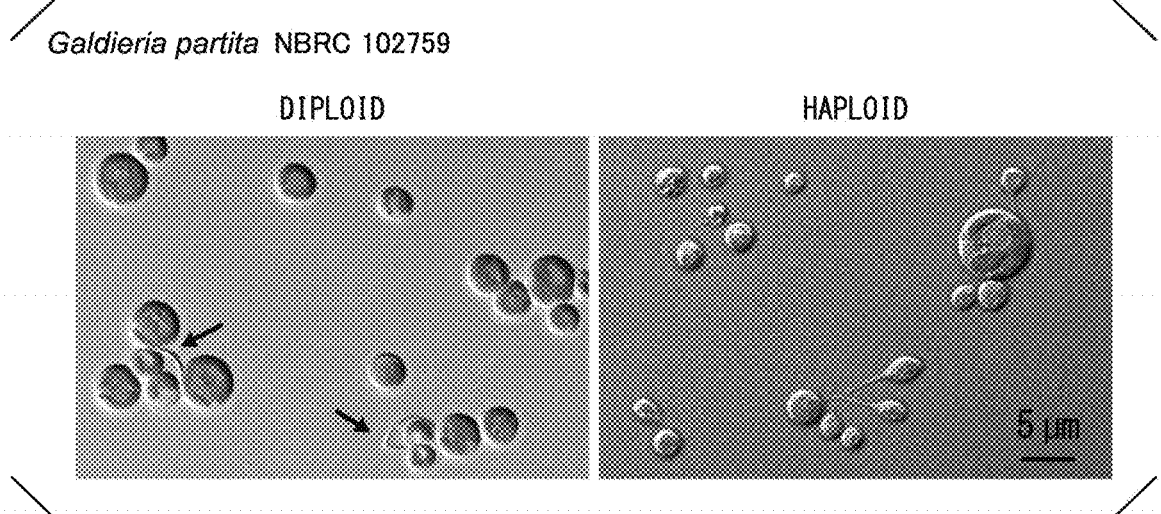
FIG. 18B shows a micrograph (left figure) of normal cells (diploids) of Galdieria partita NBRC102759 which is in the normal cell form (diploid) and a micrograph (right figure) of the same strain in the form of cells having no rigid cell wall.

In the same manner as in (Method (a)) described above, haploids were created using Galdieria partita NBRC 102759 (obtained from NITE Biological Resource Center) instead of Galdieria sulphuraria SAG108.79. FIG. 18B shows the normal cells of the Galdieria partita NBRC 102759 (left figure) and the cells having no rigid cell wall checked after the culturing of the normal cells (right figure).

(Observation by Optical Microscope)

In any of the culturing processes described above, the cells having no rigid cell wall could be easily disrupted by freeze thawing or the like, and the cell contents could be extracted. The cells having no rigid cell wall that appeared during the culturing of the algae belonging to Galdieria included both the tadpole-like cells and round cells. The cells indicated by the arrows in the left figure of FIGS. 18A and 18B are considered to be mother cell walls thrown off after mitosis.

(Allele Analysis)

Figure 19:
FIG. 19 shows the results of sequence analysis on one genomic region of Galdieria sulphuraria SAG108.79 in the form of cells having no rigid cell wall. 2N_allele1 (SEQ ID NO: 61) and 2N_allele2 (SEQ ID NO: 62) represent the sequences of alleles of Galdieria sulphuraria SAG108.79 in the normal cells (diploids). N_clone1, N_clone2, and N_clone3 represent the sequences of alleles confirmed in three strains in the form of cells having no rigid cell wall.

The cells having no rigid cell wall that appeared by the culturing of the Galdieria sulphuraria SAG 108.79 were collected, one region of the genomic DNA thereof was amplified by PCR, and the sequence thereof was analyzed by the Sanger method. For comparison, sequence analysis was also performed on the same region of the cells having a rigid cell wall. The results are shown in FIG. 19.

The cells having a rigid cell wall had two kinds of allele sequences (2N_allele1 (SEQ ID NO: 61) and 2N_allele2 (SEQ ID NO: 62)). In contrast, the cells having no rigid cell wall only had either 2N_allele1 or 2N_allele2. From this result, it has been confirmed that the cells having no rigid cell wall are haploids. Therefore, it has been revealed that the algae belonging to Galdieria also include diploid cells and haploid cells.

Hereinafter, the diploid and haploid of the Galdieria sulphuraria SAG108.79 will be described as SAG108.79 (diploid) and SAG108.79 (haploid) respectively. Furthermore, the diploid and haploid of the Galdieria partita NBRC 102759 will be described as NBRC 102759 strain (diploid) and NBRC 102759 (haploid) respectively.

[Example 11]Cell Rupturing Treatment for Algae Belonging to Galdieria

A cell rupturing treatment was performed in the same manner as in Example 8, except that instead of the YFU3 strain and the like, SAG108.79 (diploid), SAG108.79 (haploid), the NBRC 102759 strain (diploid), and NBRC #102759 (haploid) were used. Then, SDS-PAGE was performed in the same manner as in Example 8. The gel after SDS-PAGE was stained with coomassie brilliant blue, and proteins in the centrifugal supernatant and precipitate were checked.

Figure 20:
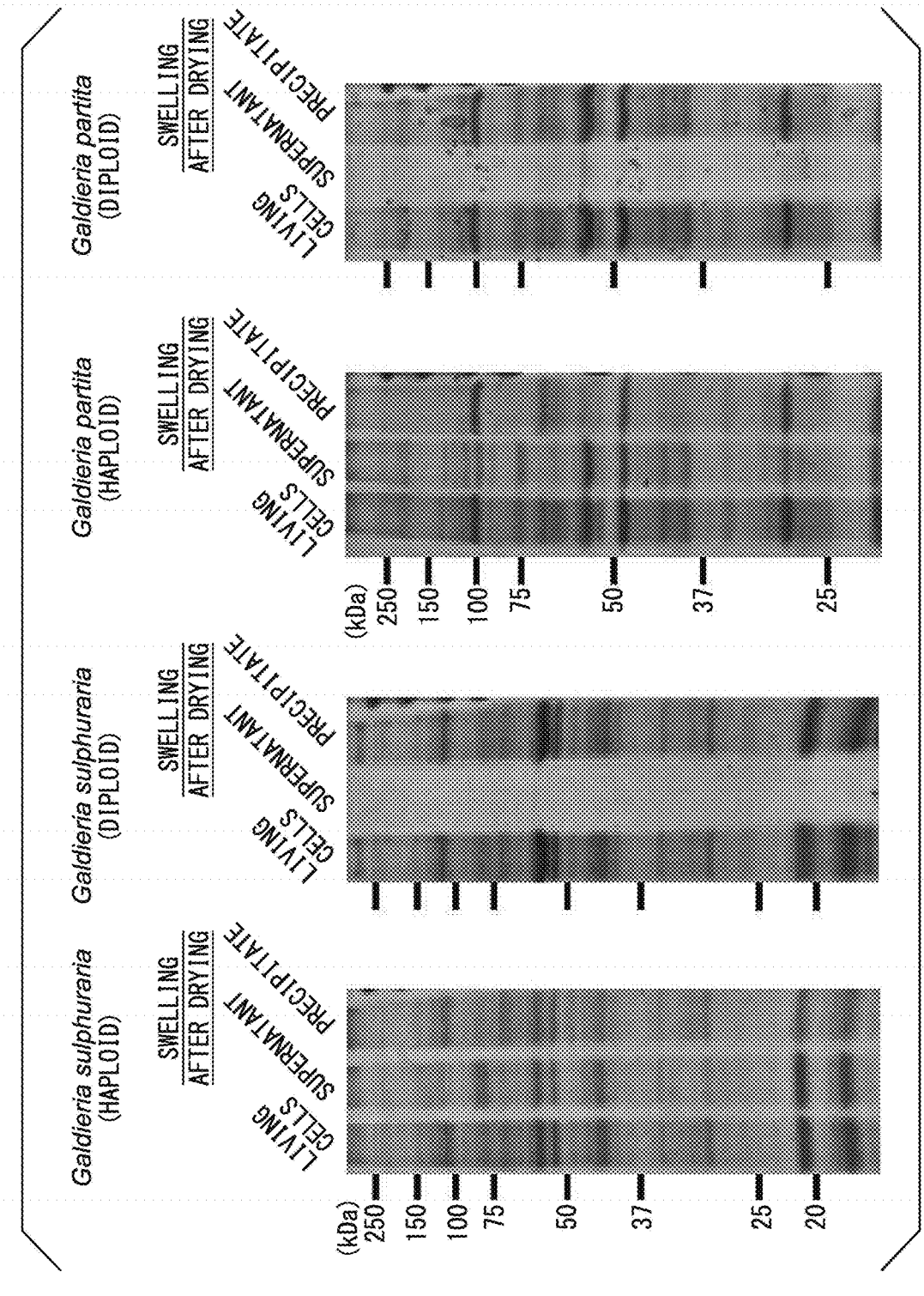
FIG. 20 shows the results of SDS-polyacrylamide electrophoresis performed on centrifugal supernatants and centrifugal precipitates which are obtained by performing a drying and swelling treatment on diploid cells and haploid cells of Galdieria sulphuraria SAG108.79 and Galdieria partita NBRC102759 and performing centrifugation on cell suspensions obtained after the swelling treatment.

The results are shown in FIG. 20. In SAG108.79 (haploid) and the NBRC 102759 strain (haploid), a plurality of kinds of proteins were detected in both the supernatant and the precipitate obtained after the drying and swelling treatment. From these results, it has been confirmed that SAG108.79 (haploid) and the NBRC 102759 strain (haploid) undergo cell rupture by the drying and swelling treatment. On the other hand, in SAG108.79 (diploid) and the NBRC 102759 strain (diploid), no protein was detected in the supernatant obtained after the drying and swelling treatment. This result shows that the cells of SAG108.79 (diploid) and the NBRC 102759 strain (diploid) do not undergo cell rupture by the drying and swelling treatment.

[Example 12]Preparation of Vitamin-Producing Ability-Enhanced Strain (Preparation of Transformant)

Figure 21:
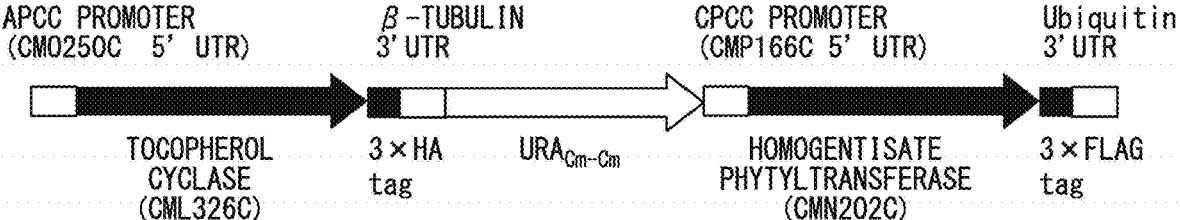
FIG. 21 shows the construct of a fragment for transformation (VE/URA$_{Cm-Cm}$ fragment) used in Example 12.

A pD184-0250-TC-URA$_{Cm-Cm}$ vector was prepared in the same manner as in "<Preparation of EGFP/URA$_{Cm-Cm}$ fragment>" in Example 2 described above, except that instead of EGFP ORF, a DNA fragment was used which was obtained by adding a 3×HA tag to the 3' terminal of Cyanidioschyzon merolae CML326C (Tocopherol cyclase: TC). Furthermore, the upstream sequence of CMP166C (−500 to −1), a fragment obtained by adding a 3×FLAG tag to the 3' terminal of CMN202C (homogentisate phytyltransferase: HPT), and the downstream sequence of CMK296C (+1 to +278) were amplified by PCR, and the resulting fragment was introduced into the downstream of a URA$_{Cm-Cm}$ selection marker of pD184-0250-TC-URA$_{Cm-Cm}$ by using the In-Fusion HD Cloning Kit, thereby preparing a pD184-0250-TC-URA$_{Cm-Cm}$ vector. By using the pD184-0250-VE-URA$_{Cm-Cm}$ vector as a template and using primer set No. 19/20 in Table 7, a VE/URA$_{Cm-Cm}$ fragment was amplified by PCR. The amplified DNA fragment (VE/URA$_{Cm-Cm}$ fragment) was used for transformation. FIG. 21 shows the constitution of the DNA fragment for transformation (VE/URA$_{Cm-Cm}$ fragment). By using the DNA fragment (VE/URA$_{Cm-Cm}$ fragment), Cyanidioschyzon merolae M4 which is a uracil auxotrophic mutant was transformed. The transformation and the culturing after the transformation were performed by the same method as that in Example 2. Then, by using an anti-HA antibody or an anti-FLAG antibody, immunoblotting was performed in the same manner as in Example 2.

Figure 22:
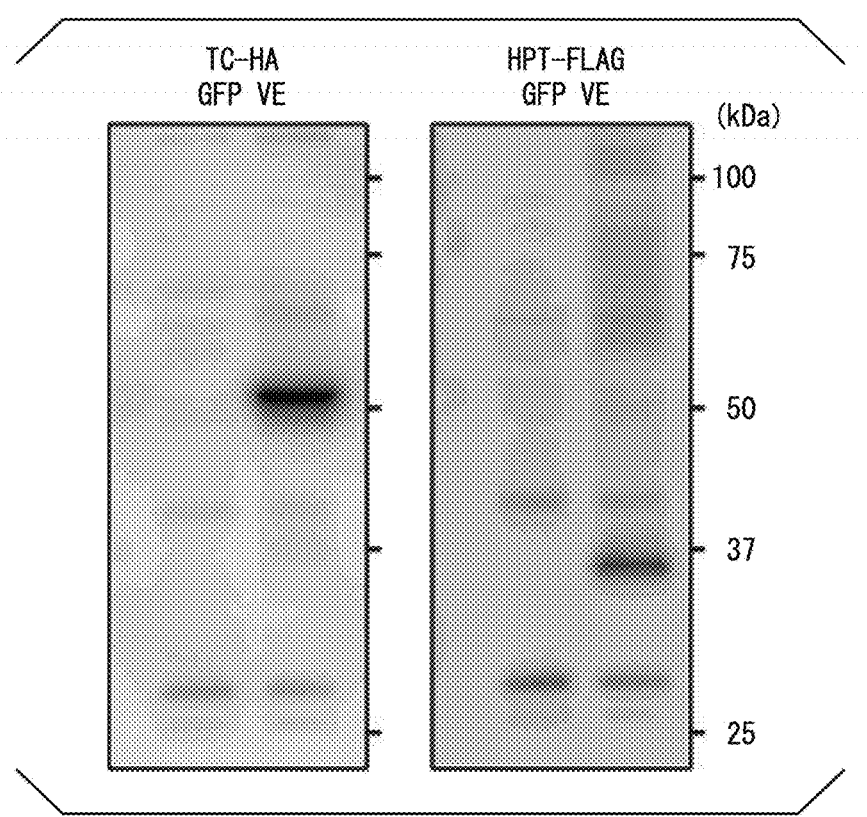
FIG. 22 shows the results of immunoblotting performed using a transformant prepared in Example 12. The left figure (TC-HA) shows the results of immunoblotting using an anti-HA antibody, and the right figure (HPT-FLAG) shows the results of immunoblotting using an anti-FLAG antibody.

The results are shown in FIG. 22. The left figure shows the results of immunoblotting using an anti-HA antibody, and the right figure shows the results of immunoblotting using an anti-FLAG antibody. In FIG. 22, "GFP" represents a cell (EGFP/URA$_{Cm-Cm}$ fragment transformant) transformed using the EGFP/URA$_{Cm-Cm}$ fragment (FIG. 1A). "VE" represents a cell transformed using the VE/URA$_{Cm-Cm}$ fragment (VE/URA$_{Cm-Cm}$ fragment transformant).

From the results in FIG. 22, it has been confirmed that the VE/URA$_{Cm-Cm}$ fragment transformant expresses tocopherol cyclase and homogentisate phytyltransferase.

(Measurement of Intracellular Vitamin E Content in Transformant)

The EGFP/URA$_{Cm-Cm}$ fragment transformant and the VE/URA$_{Cm-Cm}$ fragment transformant were allowed to grow in an MA2 medium. The cells were cultured under the conditions of continuous white light and 40° C. After being cultured, the cells were collected by centrifugation, and a soluble matter was extracted from the collected cells by using 75% ethanol. Vitamin E in the extracted soluble matter was quantified. The Vitamin E quantification was deputed to Japan Food Research Laboratories and performed by high performance liquid chromatography method.

The results are shown in Table 16. Table 16 shows relative values determined under the assumption that the vitamin E concentration (per dry weight of cells) in the EGFP/URA$_{Cm-Cm}$ fragment transformant is 1.0.

TABLE 16

| Transformant | Concentration of Vitamin E (relative value) |
|---|---|
| EGFP/URA$_{Cm-Cm}$ fragment transformant | 1.0 |
| VE/URA$_{Cm-Cm}$ fragment transformant | 1.61 |

As shown in Table 16, the vitamin E concentration was higher in the VE/URA$_{Cm-Cm}$ fragment transformant than in the EGFP/URA$_{Cm-Cm}$ fragment transformant as a negative control. From these results, it has been confirmed that the intracellular concentration of vitamin E in the Cyanidioschyzon merolae can be increased by transformation.

INDUSTRIAL APPLICABILITY

According to the present invention, there are provided novel microalgae which can be used industrially and use of the novel microalgae. The novel microalgae provided by the present invention can be used for a nutrient composition, a nutritional supplement, a composition for supplying nutrients, a method for producing a nutrient, and the like. Furthermore, the novel microalgae provided by the present invention can be used in various foods such as processed foods, functional foods, and dietary supplements, feeds, pet foods, cosmetics, and the like.

In addition, according to the present invention, there is provided a nutrient composition or a nutritional supplement which is rich in nutrients such as amino acids or vitamins. The nutrient composition or nutritional supplement can be used for foods such as various processed foods, functional foods, and dietary supplements, feeds, pet foods, cosmetics, and the like.

Moreover, according to the present invention, there is provided a method for producing a nutrient such as amino acids, vitamins, proteins, lipids, and dietary fiber.

The invention claimed is:

1. A method for producing a haploid alga, comprising:

(a) culturing a diploid cell of an alga belonging to Galdieria or Cyanidium until the alga enters the stationary phase; and (b) isolating a haploid cell which has no rigid cell wall from the culture obtained by (a); and (c) culturing the haploid cell isolated in (b).

2. The method for producing a haploid alga according to claim 1, wherein the culturing in the (a) is performed under a condition of temperature of 30° C. to 50° C., pH of 1.0 to 5.0, and $CO_2$ concentration of 1% to 3%.

3. The method for producing a haploid alga according to claim 1, wherein the haploid cell is ruptured under a condition of pH 7.

4. The method for producing a haploid alga according to claim 3, wherein a ribulose 1,5-bisphosphate carboxylase/oxygenase large subunit gene of the alga has a base sequence shown in SEQ ID NO: 1 or 2.

5. The method for producing a haploid alga according to claim 4, wherein the alga is selected from the group consisting of a Cyanidium sp. YFU3 strain (FERM BP-22334), a Cyanidium sp. HKN1 strain (FERM BP-22333).

6. The method for producing a haploid alga according to claim 1, wherein the alga is a transformant obtained by genetic modification using a genetic engineering technique.

7. The method for producing a haploid alga according to claim 6, wherein the transformant is obtained by using an auxotrophy-related gene as a selection marker.

* * * * *

SEQUENCE LISTING

```
Sequence total quantity: 88
SEQ ID NO: 1           moltype = DNA  length = 856
FEATURE                Location/Qualifiers
source                 1..856
                       mol_type = other DNA
                       organism = Cyanidium sp.
SEQUENCE: 1
ttattaggtt gtacctgtaa acccaaatta ggtctatctg gaaaaaacta tggacgtgtt   60
gtgtatgaag gtttaaaagg tggattagac ttcctaaaag atgacgaaaa tattaattca  120
caacctttca tgcgttggag agaccgtttc ttatacgtaa tggaaggggt gaatagagca  180
tctgcagcat caggtgaagt gaaaggttcc tatttgaacg taacggcagc caccatggag  240
gagatttata agagggctga attcgccaaa gaagtaggta cagtcatcat tatgatagac  300
```

```
cttgtgattg gttatacagc gattcaaagc atggcggttt ggtcacgtga aaataacatg  360
attcttcacc tacacagagc aggcaactcc acatattctc gtcagaaaaa tcatggcatt  420
aacttccgag tgatttctaa gtggatgcgt atggcaggag tggatcatat tcatgcagga  480
acagtggtag gtaaacttga aggtgatcct gttattatca aaggttttta taacacatta  540
ttactaccta aattagagat caatttgcct caaggtttgt tctttgaaat ggattgggca  600
tctatacgta aagtcatgcc agtcgcttca ggtggtatcc atgcaggtca aatgcatcag  660
cttattcatt acttaggtga agacgtcgtg ttgcaattcg gaggaggaac gattggtcac  720
ccagacggaa ttcaagccgg agccactgcc aaccgtgtag ctttagaatc catgatttta  780
gcaagaaatg aaggtcgaga ttatttcaat gaaggacctc aaatcttaag agatgcagcg  840
aaaaattgtg gtcctc                                                  856
```

SEQ ID NO: 2        moltype = DNA  length = 874
FEATURE             Location/Qualifiers
source              1..874
                    mol_type = other DNA
                    organism = Cyanidium sp.
SEQUENCE: 2

```
tcgtccatta ttaggttgta cctgtaaacc caaattaggt ctatctgaaa aaaactatgg  60
acgtgttgtg tatgaaggtt taaaaggtgg attagacttc ctaaaagatg acgaaaatat  120
taattcacaa cctttcatgc gttggagaga ccgtttctta tacgtaatgg aagggggtgaa  180
tagagcatct gcagcatcag gtgaagtgaa aggttcctat ttgaacgtaa cggcagccac  240
catggaggag atttataaga gggctgaatt cgccaaagaa ggtacag tcatcattat  300
gatagacctt gtgattggtt atacagcgat tcaaagcatg gcggtttggt cacgtgaaaa  360
taacatgatt cttcacctac acagagcagg caactccaca tattctcgtc agaaaaatca  420
tggcattaac ttccgagtga tttctaagtg gatgcgtatg gcaggagtgg atcatattca  480
tgcaggaaca gtggtaggta aacttgaagg tgatcctgtt attatcaaag gtttttataa  540
cacattatta ctacctaaat tagagatcaa tttgcctcaa ggtttgttct ttgaaatgga  600
ttgggcatct atacgtaaag tcatgccagt cgcttctggt ggtatccatg caggtcaaat  660
gcatcagctt attcattact taggtgaaga cgtcgtgttg caattcggag gaggaacgat  720
tggtcaccca gacggaattc aagccggagc cactgccaac cgtgtagctt tagaatccat  780
gattttagca agaaatgaag gtcgagatta tttcaatgaa ggacctcaaa tcttaagaga  840
tgcagcaaaa aattgtggtc ctcttcaaac ggct                              874
```

SEQ ID NO: 3        moltype = DNA  length = 1683
FEATURE             Location/Qualifiers
source              1..1683
                    mol_type = other DNA
                    organism = Cyanidioschyzon merolae
SEQUENCE: 3

```
atgcctctac acaagacgaa cgttgaaaaa ggcggtgcga agcgttttca gcatatcgac  60
acaagctcgc tggctttcga gaccggcttt gcaagcttcg cgctcgagga gttccccaag  120
taccagttgc gagccgagcc gatgccgtcg gctgttgccg aaggtatcat tacgcaggag  180
ctggagctag acggtaaccc tgcactaaac ctggcatcct ttgtgacgac gcgctttgat  240
gaaacgacgc acaagctctg tgatcgcatg cttccggtga actggatcga ctttgacgag  300
tatccgcaaa ccgtggagat ccacaaccgc tgcgtcaata tcatagcgaa cctttttcat  360
gctcctctcg aggagggtca gcaggctgtt ggcaccagca ctgtaggctc ctctgaggcg  420
atcatgctgg cggtgctcgc gatgaagtgg cgttggcgag cagctcgcaa ggcagccgag  480
aaggactacg cacgcccgaa catggtgatg ggttcagaag tgcaggtctg ctgggagaaa  540
gcggactgct tactttgatgt ggaaccacgc tacgtaccat gcacgacga tgtatacgtc  600
atgaatccga aaaagctat agagctttgt gatgagaaca ccatcggaat ttgcggcatt  660
ctaggtacca cctacaccgg acaatttgaa gacattgcca ctttggacgc tctcgtgacg  720
cagatgaacg agcagaaggg ttttgatatc ggtatccatg tagacgcagc atcaggaggc  780
ttcatagccc cgttttgtta ccccaatctc aggtgggact tcgtttgaa gaacgtgcgt  840
tctatcaatg tttcggggca caagtacggt ctcgcgccct gtggcatcgg atggctcatt  900
tttcgcagcg ctgcgtatct gccggaggag ctcgtctttc acgtcaatta cctgggcgcg  960
gaccaagcct cattcacctt gaacttttca cgcggttccg ctcagattgt ggcgtcatac  1020
tatttgctgt tgcgcttagg ccgtcgggga taccagaatc taatgcacac cctgaaagaa  1080
ttggcttcgt actttgcaac acgtatcacg gaggatgggc gtttccgcct gcttagtgac  1140
aacgaaagcc tgcccttggt tgcgtttgcg atcccagatg accagcgcac gaaactgggt  1200
tttgatgagt ttgccatagc gggagagtta cgcaaacgtg gatggatcgt tcccgcgtat  1260
acgctggcac cgaacctgca gcaccagaaa ctgctgcggg tggtggtgcg ggtcggtttt  1320
acccgcgatc gggcagatat gctggtccag gatattcggg ccgcatatga tcatttagtc  1380
gccatggctg gactgttgaa cctatttgga cagggcctgg ctgtggacga tacggcgtcg  1440
acaaagaaac cggaaagcga gcataccgcc accgcccctcg gtaagatgct gcacggcaac  1500
aagtcgctac aggaacacgc ggaagagctg cggcgaacgc acgatttacc gggagcccgc  1560
cacctcattc atatgcaaaa ttggggaacc attcatgcga aagagggcac caaggatgcg  1620
gaaccgcgtc gctcgcctgt ggaccgccac caacggcaca agaaacgcag cggtgctgta  1680
tgc                                                                1683
```

SEQ ID NO: 4        moltype = AA  length = 561
FEATURE             Location/Qualifiers
source              1..561
                    mol_type = protein
                    organism = Cyanidioschyzon merolae
SEQUENCE: 4

```
MPLHKTNVEK GGAKRFQHID TSSLAFETGF ASFALEEFPK YQLRAEPMPS AVAEGIITQE  60
LELDGNPALN LASFVTTRFD ETTHKLCDRM LPVNWIDFDE YPQTVEIHNR CVNIIANLFH  120
APLEEGQQAV GTSTVGSSEA IMLAVLAMKW RWRAARKAAG KDYARPNMVM GSEVQVCWEK  180
ATAYFDVEPR YVPLHDDVYV MNPEKAIELC DENTIGICGI LGTTYTGQFE DIATLDALVT  240
```

-continued

```
QMNEQKGFDI GIHVDAASGG FIAPFCYPNL RWDFRLKNVR SINVSGHKYG LAPCGIGWLI   300
FRSAAYLPEE LVFHVNYLGA DQASFTLNFS RGSAQIVASY YLLLRLGRRG YQNLMHTLKE   360
LASYFATRIT EDGRFRLLSD NESLPLVAFA IPDDQRTKLG FDEFAIAGEL RKRGWIVPAY   420
TLAPNLQHQK LLRVVVRVGF TRDRADMLVQ DIRAAYDHLV AMAGLLNLFG QGLAVDDTAS   480
TKKPESEHTA TALGKMLHGN KSLQEHAEEL RRTHDLPGAR HLIHMQNWGT IHAKEGTKDA   540
EPRRSPVDRH QRHKKRSGAV C                                            561

SEQ ID NO: 5            moltype = DNA  length = 1239
FEATURE                 Location/Qualifiers
source                  1..1239
                        mol_type = other DNA
                        organism = Cyanidioschyzon merolae
SEQUENCE: 5
atgttcatcg tttccgcaac atgttgctcc ttggggaaga gacaagcacg ctcctttcta   60
ggacgctgtt ggaaggggac tggtgccgga tgtgcgttcc gcagtgggaa ctgcggcctc   120
agagctgcga cagggtgctc gttgcgggcc tgcagctccg agttggatgc cagctccgac   180
gcagtcaggg ctgggacaa cttcgggcaa cgagccagcg acgctgatca gggccgccct   240
gtgcaccaag taggccgtca aacggaaggc gagcgcttcg cggtccgccg tgcactgcgc   300
gttttttctca agttcactcg cccgcatacg atgttaggaa gtgcggtttc catctgctcg   360
ctttccttga tgggaagcgt atctgccggg caggctctag gtgcagccac tttaccactt   420
tggactcaac tttttccagt ccttcttgtg ggtctcgtgc cagcgctctt gatgaacatt   480
tatatcgtcg gtctgaatca actgtgtgat attccagttg accgtgtgaa caagccttac   540
ttgcccctag caagcggaga gctatccggtt cccgctgcag tttccctcgt aggtatgtgt   600
cttctgggat cgtttagcct aggcttctgg cttccacaga gcaccgcggc cctacgtttt   660
gcacttgtcg caagctgcat cctagggacg ttatactcgt tgccaccgat tcggttgaag   720
cgtttcccac tgctggcgtc gctctgcatt ctagtcgtaa gaggtgcggt cgtgaacatt   780
ggtttttact tgcacgcgcg ctcagctgtc atgtcgctga gaggcccatg gctagcagaa   840
ctttccccac tgatcaagtt cacgacggtg ttctttgctg cgtacgggat cgtgattgcg   900
ttaatgaaag atattcccga tgcgaaaggt gataaccagc atcaactcag cagtttcacg   960
cttcagttcg gagaacggaa catcttccgc ttttgcgtca cgatgttgat cttcatgttc   1020
atcgctggcg gtatattttg catgtcgtcg gcgctcgcga cggtcccgcg gcatcgagca   1080
tttgcggcag gcggttttca cttcgttgct gctgcttggc tgcggtggag atcgagagcc   1140
tccatgatga aagcgcatcg tagcgaggtg gtgtacaact tttacatgga catttggaag   1200
ctctttttatc tcgaatatgt agttctacct ctactgctt                        1239

SEQ ID NO: 6            moltype = AA  length = 413
FEATURE                 Location/Qualifiers
source                  1..413
                        mol_type = protein
                        organism = Cyanidioschyzon merolae
SEQUENCE: 6
MFIVSATCCS LGKRQARSFL GRCWKGTGAG CAFRSGNCGL RAATGCSLRA CSSELDASSD   60
AVRAGDNFGQ RASDADQGRP VHQVGRQTEG ERFAVRRALR VFLKFTRPHT MLGSAVSICS   120
LSLMGSVSAG QALGAATLPL WTQLFPVLLV GLVPALLMNI YIVGLNQLCD IPVDRVNKPY   180
LPLASGELSV PAAVSLVGMC LLGSFSLGFW LPQSTAALRF ALVASCILGT LYSLPPIRLK   240
RFPLLASLCI LVVRGAVVNI GFYLHARSAV MSLRGPWLAE LSPLIKFTTV FFAAYGIVIA   300
LMKDIPDAKG DNQHQLSSFT LQFGERNIFR FCVTMLIFMF IAGGIFCMSS ALATVPRHRA   360
FAAGGFHFVA AAWLRWRSRA SMMEAHRSEV VYNFYMDIWK LFYLEYVVLP LLL           413

SEQ ID NO: 7            moltype = DNA  length = 1701
FEATURE                 Location/Qualifiers
source                  1..1701
                        mol_type = other DNA
                        organism = Cyanidioschyzon merolae
SEQUENCE: 7
atgcgagaaa agctccagtg tagaggttcg gggttcgagg tccaacggga gctccgaagc   60
ggcaaggttg ccgtaaacgc agcggcagcg tgggtgtcgc cgtcgtctcc gctgtcctct   120
gttgttgtgt acgcgtacca ggagcacgct ggtcgttgca gggcactccc agagccacca   180
tggagaaagc ataggcaccg ggctcggtcg ctgctcgttt caagctggta caacgatac    240
ccaggaacgg ggccgctgc agttctcacg ggacgccggc ggagcgcttc gtcgctggat   300
gcgagccccg ttcgacagca tgtgctatct gggggttctc gtggcagtct gcgtaccctg   360
aagcgggtct caggtgcgag gcgacgcaga gacgaacgtt gttgtcatca tgaggcgacc   420
aaggagaccg cagatcccct ggaacttccc cacgccggtg ttcatatgcc gagcgtagat   480
cgtggattct tcgagggctg gtacgtccga atcgtgctgc ccacagaggc gacttcgcatt   540
gcgttcatgt acagcttgga agacggtcgc aggggtcgaa tacaggtttt gagctctgga   600
gtgcaggacg agctgcttgt ttcgcgagaa atgatggatg ctttttttcc ggcgctgcgg   660
cacctgccaa cgtcgacgtt acgcattggt cagtggggtc gaacgagtga cctcctcagc   720
gacgaacgag cagagcacgc gcgctccctg gcccctagtc ttttccgaga acacgtgcat   780
acgggatatc agctctctgc tcagtggcat cagggctcga tccaagcaga cgatgtgcat   840
cgagagcgtt ccatggtagc gcacctgagc ccagacataa gttgcgcttt cgatatgcga   900
atcgagccgc tcttatcgtg ggggtcggat ggtgcgcgct cgactggaac ctggctcacg   960
cgttttcaag tctttgaacc aggctggcag atactctctg ctttcgctcg atccactggt   1020
atatttcggg actggcatgg tcgcgtttt cgcttcgagc gtgcacccac gtatatcgag   1080
aagaactggg gcagtgcgtt cccatcgcga tggttctgtca cgtctttgac   1140
gtgctccgga aggacgcatc atcgctggag ctgtcgtccg cagacatcga tgcaccgttg   1200
actttgacct gtgtgggagc gcgtcgagag ctctgctggc cccagcgacc gaataaggtt   1260
gtagctcggg aaaccattgg tatcatcgcg ttccactgga agggatattt gtgggagttc   1320
gctgcttgga actgccgccg catatcctgg agtgtccagt ggggcaactg gcagatggaa   1380
gcgcacggca cgcgctatag cgtaaaggtc tccgctgaga ccgctgaacc agggggcgtat   1440
```

```
gtactgggtc cgacccgtca cggcatgcag tttgtggtaa gagacggtgc gcgtggtacg   1500
cttcgtttgc agctgcgaga cgagcaggca aacgttgtga ttttggacgc actctgtcgc   1560
aacgctgctg ctgtcgagct tggtggcgag ctggcgtcgg acccaaatgg aacgagttgg   1620
acggcggagc gcggagcctt tcccccaccg gtaaaggcat tgtttcttat tggcgaacga   1680
cccgggcgag ccgttcgcgt c                                             1701

SEQ ID NO: 8             moltype = AA   length = 567
FEATURE                  Location/Qualifiers
source                   1..567
                         mol_type = protein
                         organism = Cyanidioschyzon merolae SEQUENCE: 8
MREKLQCRGS GFEVQRELRS GKVAVNAAAA WVSPSSPLSS VVVYAYQEHA GRCRALPEPP    60
WRKHRHRARS LLVSSWYNDH PGTGPRAVLT GRRRSASSLD ASPVRQHVLS GGSRGSLRTL    120
KRVSGARRRR DERCCHHEAT KETADPLELP HAGVHMPSVD RGFFEGWYVR IVLPTEATSL    180
AFMYSLEDGR RGRIQVLSSG VQDELLVSRE MMDGFFPALR HLPTSTLRIG QWGRTSDLLS    240
DERAEHARSL APSLFREHVH TGYQLSAQWH QGSIQADDVD RERSMVAHLS PDISCAFDMR    300
IEPLLSWGSD GARSTGTWLT RFQVFEPGWQ ILSAFARSTG IFRDWHGRVF RFERAPTYIE    360
KNWGSAFPSR WFWLQCHVFD VLREDASSLE LSSADIDAPL TLTCVGARRE LCWPQRPNKV    420
VARETIGIIA FHWKGYLWEF AAWNCRRISW SVQWGNWQME AHGTRYSVKV SAETAEPGAY    480
VLGPTRHGMQ FVVRDGARGT LRLQLRDEQA NVVILDALCR NAAAVELGGE LASDPNGTSW    540
TAERGAFPPP VKALFLIGER PGRAVRV                                       567

SEQ ID NO: 9             moltype = DNA   length = 600
FEATURE                  Location/Qualifiers
source                   1..600
                         mol_type = other DNA
                         organism = Cyanidioschyzon merolae SEQUENCE: 9
cgacgagaac gtataaggag tgcgcacggc gttttgttac aataccgata gatgagtttc    60
gaacatcgca ttcacaccat gagcgggggc gcacgctcca gagagtggag atggaaaagt    120
gccagcggag ccctgaggat gcaaaaaagt acggaccgct gacggaagag caaatggaaa    180
ggagggcgaa acttcgaggg ctacttgcat tagtaagtac aaccaacgat ggtaagaaac    240
gtatggagtt tgcgaaccga gactttaacg ctgccatcaa tatcaggaga tgtgcggtgc    300
tggagacgag acctccagag tgaacaagaa ggtacttttt tggacaacct tctaaggtcg    360
aactatatga gataaaattg gaagaagtag ttggtggccg gtccaaaaag acggggaggc    420
gtctgcacat cagttggaga cgtttttgtcc aaggcgcgcc gatcgccact actgtacacg    480
gccggcgaga acgtggcgag aatacgcaag cgagctcgcc ggctgcgctc gctgcaccac    540
cgtcttttga ctcacaactt cgcgatatct ttgttctctg tgtttcttcg ttcgttgacc    600

SEQ ID NO: 10            moltype = DNA   length = 599
FEATURE                  Location/Qualifiers
source                   1..599
                         mol_type = other DNA
                         organism = Cyanidioschyzon merolae SEQUENCE: 10
gcctcgaggg cctctctgcg tcgtcgccga agagctgaca gaaagcgttc caggtgcgcg    60
agcctcactt gggcatatac cagtgagtgg gtgcgggcac cactagtccg gtgaactcgg    120
ccggtcagcc aaatcctcca cccggaaggt tcgcaccgtc actgcagcga gcgcagtcca    180
agcttctagg cgcggtaggc gtgcaggatg cgcgtccaat tcggcaagat gcgctgccgg    240
catgcccgcc catgtgtcgg acccattccg tgcaagcgac gcacgtcgag cgatttgggg    300
cgcgtgcata ggcccgcgca cgatgaatga tctggttgca tgcgtacaca aacaggactt    360
ttctgaccat gatatcccta ttcggacatg acgcatcgcg cacttccgca cacctcgtt    420
gctgggcgca gccggccgcg gcacctcgcg agcacgccgg cctcggcagc gcgagcgcat    480
tagcgagatc tccgacgacg gacgtgggtc gagattcgat ttcggaggcc gcacgacgca    540
aaaaggtcat tcgagtttgt gtctgcggac tctgaacgtt cctcgtaaag cacttctga    599

SEQ ID NO: 11            moltype = DNA   length = 500
FEATURE                  Location/Qualifiers
source                   1..500
                         mol_type = other DNA
                         organism = Cyanidioschyzon merolae SEQUENCE: 11
ccctcactgg catggcaaag ccgttctgtc tccgtgccgc atctgctcca ggggtgtaag    60
cgcgattgcg aatgctcaag gaaggttacg tgcacagtgg aatgcacgaa ataaccagta    120
catccgaaag gaagtacaag taatggaacc tgaaggtagg gtccagcagc atgatgggcg    180
ctttcccgaa tgtcaatacc gatctatcgc gcaatctggc ctccatggtc catagaagcg    240
ctttggcatc ggcgggagaa ccgggcgtcg ccccgcgctg cgctccatgg aacaatgctc    300
aaatcacgaa taaattgtac tttattaaat ctgtatgtac tatgatgtac aaaatagcat    360
tccaggaatc ccgagatcac acacgcgctc gagacgtgaa ctgtctcgtc actctcggct    420
acggcttcat cttcctcgta tttcttcgcc attagatacg agtgcggtaa gattctgggc    480
tgaagttttc aatattagtg                                               500

SEQ ID NO: 12            moltype = DNA   length = 100
FEATURE                  Location/Qualifiers
source                   1..100
                         mol_type = other DNA
                         organism = Cyanidium sp.

SEQUENCE: 12
```

-continued

```
attttgtcac ctgaacctat ggatggtaaa caatgggttc tggtttcacc aaatggatgg   60
atggaaccct tcatggagcg gtgtctctcg taggtttggt                        100

SEQ ID NO: 13           moltype = DNA   length = 100
FEATURE                 Location/Qualifiers
source                  1..100
                        mol_type = other DNA
                        organism = Cyanidium sp.
SEQUENCE: 13
attttgtgac ctgaacctat ggatgataaa caatgggttc tggtttcacc aaatggatgg   60
atggtaccct tcagggagcg gtgtctctcg taggtttggt                        100

SEQ ID NO: 14           moltype = DNA   length = 100
FEATURE                 Location/Qualifiers
source                  1..100
                        mol_type = other DNA
                        organism = Cyanidium sp.
SEQUENCE: 14
attttgtcac ctgaacctat ggatggtaaa caatgggttc tggtttcacc aaatggatgg   60
atggtaccct tcagggagcg gtgtctctcg taggtttggt                        100

SEQ ID NO: 15           moltype = DNA   length = 21
FEATURE                 Location/Qualifiers
source                  1..21
                        mol_type = other DNA
                        organism = synthetic construct
SEQUENCE: 15
tagaggaagg agaagtcgta a                                             21

SEQ ID NO: 16           moltype = DNA   length = 24
FEATURE                 Location/Qualifiers
source                  1..24
                        mol_type = other DNA
                        organism = synthetic construct
SEQUENCE: 16
ttgcgttcaa agactcgatg attc                                          24

SEQ ID NO: 17           moltype = DNA   length = 20
FEATURE                 Location/Qualifiers
source                  1..20
                        mol_type = other DNA
                        organism = synthetic construct
SEQUENCE: 17
aaaactttcc aaggrccwgc                                               20

SEQ ID NO: 18           moltype = DNA   length = 23
FEATURE                 Location/Qualifiers
source                  1..23
                        mol_type = other DNA
                        organism = synthetic construct
SEQUENCE: 18
gcwgttggtg tytchacwaa atc                                           23

SEQ ID NO: 19           moltype = DNA   length = 39
FEATURE                 Location/Qualifiers
source                  1..39
                        mol_type = other DNA
                        organism = synthetic construct
SEQUENCE: 19
cttcgttcgt tgaccatgtt cgttcagacc agtttcttt                          39

SEQ ID NO: 20           moltype = DNA   length = 20
FEATURE                 Location/Qualifiers
source                  1..20
                        mol_type = other DNA
                        organism = synthetic construct
SEQUENCE: 20
atcattcgca acgccagatg                                               20

SEQ ID NO: 21           moltype = DNA   length = 34
FEATURE                 Location/Qualifiers
source                  1..34
                        mol_type = other DNA
                        organism = synthetic construct
SEQUENCE: 21
taaactagct atttatctgg tacatatcat tcat                               34

SEQ ID NO: 22           moltype = DNA   length = 44
FEATURE                 Location/Qualifiers
```

```
source                   1..44
                         mol_type = other DNA
                         organism = synthetic construct
SEQUENCE: 22
tcgctgagcg gtttcacact ttttgcctgc acaagttttc gtac                    44

SEQ ID NO: 23            moltype = DNA  length = 48
FEATURE                  Location/Qualifiers
source                   1..48
                         mol_type = other DNA
                         organism = synthetic construct
SEQUENCE: 23
ggcgttgcga atgatatgaa ctttaataaa attgatttag acaattgg               48

SEQ ID NO: 24            moltype = DNA  length = 39
FEATURE                  Location/Qualifiers
source                   1..39
                         mol_type = other DNA
                         organism = synthetic construct
SEQUENCE: 24
taaatagcta gtttataaaa gccagtcatt aggcctatc                         39

SEQ ID NO: 25            moltype = DNA  length = 36
FEATURE                  Location/Qualifiers
source                   1..36
                         mol_type = other DNA
                         organism = synthetic construct
SEQUENCE: 25
ggtcaacgaa cgaagaaaca cagagaacaa agatat                            36

SEQ ID NO: 26            moltype = DNA  length = 24
FEATURE                  Location/Qualifiers
source                   1..24
                         mol_type = other DNA
                         organism = synthetic construct
SEQUENCE: 26
gaaaccgctc agcgaccaag cgac                                         24

SEQ ID NO: 27            moltype = DNA  length = 20
FEATURE                  Location/Qualifiers
source                   1..20
                         mol_type = other DNA
                         organism = synthetic construct
SEQUENCE: 27
acacgaatca cacggtgctg                                              20

SEQ ID NO: 28            moltype = DNA  length = 21
FEATURE                  Location/Qualifiers
source                   1..21
                         mol_type = other DNA
                         organism = synthetic construct
SEQUENCE: 28
ttgccgataa cgcagaagag a                                            21

SEQ ID NO: 29            moltype = DNA  length = 28
FEATURE                  Location/Qualifiers
source                   1..28
                         mol_type = other DNA
                         organism = synthetic construct
SEQUENCE: 29
cgacgagaac gtataaggag tgcgcacg                                     28

SEQ ID NO: 30            moltype = DNA  length = 30
FEATURE                  Location/Qualifiers
source                   1..30
                         mol_type = other DNA
                         organism = synthetic construct
SEQUENCE: 30
acactttttg cctgcacaag ttttcgtacg                                   30

SEQ ID NO: 31            moltype = DNA  length = 24
FEATURE                  Location/Qualifiers
source                   1..24
                         mol_type = other DNA
                         organism = synthetic construct
SEQUENCE: 31
atgttcgttc agaccagttt cttt                                         24

SEQ ID NO: 32            moltype = DNA  length = 22
```

-continued

```
FEATURE              Location/Qualifiers
source               1..22
                     mol_type = other DNA
                     organism = synthetic construct
SEQUENCE: 32
taaaagccag tcattaggcc ta                                          22

SEQ ID NO: 33        moltype = DNA   length = 19
FEATURE              Location/Qualifiers
source               1..19
                     mol_type = other DNA
                     organism = synthetic construct
SEQUENCE: 33
gaactgaggg gcgaacgca                                              19

SEQ ID NO: 34        moltype = DNA   length = 20
FEATURE              Location/Qualifiers
source               1..20
                     mol_type = other DNA
                     organism = synthetic construct
SEQUENCE: 34
ccctagcagc tgactgtatc                                             20

SEQ ID NO: 35        moltype = DNA   length = 35
FEATURE              Location/Qualifiers
source               1..35
                     mol_type = other DNA
                     organism = synthetic construct
SEQUENCE: 35
caccatcacc atcacgcgtg agtcagttca ctgac                           35

SEQ ID NO: 36        moltype = DNA   length = 34
FEATURE              Location/Qualifiers
source               1..34
                     mol_type = other DNA
                     organism = synthetic construct
SEQUENCE: 36
aagctcagct aattacagct tgctgacctt accc                            34

SEQ ID NO: 37        moltype = DNA   length = 20
FEATURE              Location/Qualifiers
source               1..20
                     mol_type = other DNA
                     organism = synthetic construct
SEQUENCE: 37
gtgatggtga tggtgatggg                                             20

SEQ ID NO: 38        moltype = DNA   length = 24
FEATURE              Location/Qualifiers
source               1..24
                     mol_type = other DNA
                     organism = synthetic construct
SEQUENCE: 38
taattagctg agcttggact cctg                                       24

SEQ ID NO: 39        moltype = DNA   length = 33
FEATURE              Location/Qualifiers
source               1..33
                     mol_type = other DNA
                     organism = synthetic construct
SEQUENCE: 39
tatacgttct cgtcgcgtca ccctcgggac ttg                             33

SEQ ID NO: 40        moltype = DNA   length = 33
FEATURE              Location/Qualifiers
source               1..33
                     mol_type = other DNA
                     organism = synthetic construct
SEQUENCE: 40
gcaggcaaaa agtgtgaaac cgctcagcga cca                             33

SEQ ID NO: 41        moltype = DNA   length = 37
FEATURE              Location/Qualifiers
source               1..37
                     mol_type = other DNA
                     organism = synthetic construct
SEQUENCE: 41
aagctcagct aattacgacg agaacgtata aggagtg                         37
```

```
SEQ ID NO: 42            moltype = DNA   length = 37
FEATURE                  Location/Qualifiers
source                   1..37
                         mol_type = other DNA
                         organism = synthetic construct
SEQUENCE: 42
gcccttgctc accatggtca acgaacgaag aaacaca                                      37

SEQ ID NO: 43            moltype = DNA   length = 18
FEATURE                  Location/Qualifiers
source                   1..18
                         mol_type = other DNA
                         organism = synthetic construct
SEQUENCE: 43
atggtgagca agggcgag                                                           18

SEQ ID NO: 44            moltype = DNA   length = 20
FEATURE                  Location/Qualifiers
source                   1..20
                         mol_type = other DNA
                         organism = synthetic construct
SEQUENCE: 44
cttgtacagc tcgtccatgc                                                         20

SEQ ID NO: 45            moltype = DNA   length = 47
FEATURE                  Location/Qualifiers
source                   1..47
                         mol_type = other DNA
                         organism = synthetic construct
SEQUENCE: 45
gacgagctgt acaagtaaac tagctattta tctggtacat atcattc                          47

SEQ ID NO: 46            moltype = DNA   length = 36
FEATURE                  Location/Qualifiers
source                   1..36
                         mol_type = other DNA
                         organism = synthetic construct
SEQUENCE: 46
caccatcacc atcacacact ttttgcctgc acaagt                                      36

SEQ ID NO: 47            moltype = DNA   length = 22
FEATURE                  Location/Qualifiers
source                   1..22
                         mol_type = other DNA
                         organism = synthetic construct
SEQUENCE: 47
cgacgagaac gtataaggag tg                                                      22

SEQ ID NO: 48            moltype = DNA   length = 21
FEATURE                  Location/Qualifiers
source                   1..21
                         mol_type = other DNA
                         organism = synthetic construct
SEQUENCE: 48
acactttttg cctgcacaag t                                                       21

SEQ ID NO: 49            moltype = DNA   length = 36
FEATURE                  Location/Qualifiers
source                   1..36
                         mol_type = other DNA
                         organism = synthetic construct
SEQUENCE: 49
ttcgcccctc agttcacact ttttgcctgc acaagt                                      36

SEQ ID NO: 50            moltype = DNA   length = 32
FEATURE                  Location/Qualifiers
source                   1..32
                         mol_type = other DNA
                         organism = synthetic construct
SEQUENCE: 50
gtcagctgct aggggaaacc gctcagcgac ca                                          32

SEQ ID NO: 51            moltype = DNA   length = 20
FEATURE                  Location/Qualifiers
source                   1..20
                         mol_type = other DNA
                         organism = synthetic construct
SEQUENCE: 51
acacgaatca cacggtgctg                                                         20
```

-continued

```
SEQ ID NO: 52            moltype = DNA   length = 21
FEATURE                  Location/Qualifiers
source                   1..21
                         mol_type = other DNA
                         organism = synthetic construct
SEQUENCE: 52
ttgccgataa cgcagaagag a                                        21

SEQ ID NO: 53            moltype = DNA   length = 17
FEATURE                  Location/Qualifiers
source                   1..17
                         mol_type = other DNA
                         organism = synthetic construct
SEQUENCE: 53
aggtcgctga tgcggaa                                             17

SEQ ID NO: 54            moltype = DNA   length = 36
FEATURE                  Location/Qualifiers
source                   1..36
                         mol_type = other DNA
                         organism = synthetic construct
SEQUENCE: 54
gaatacgttg aatgattcct aatgggcaga agcaag                       36

SEQ ID NO: 55            moltype = DNA   length = 32
FEATURE                  Location/Qualifiers
source                   1..32
                         mol_type = other DNA
                         organism = synthetic construct
SEQUENCE: 55
ccgcatcagc gaccttgtcg gaacactccg cc                           32

SEQ ID NO: 56            moltype = DNA   length = 27
FEATURE                  Location/Qualifiers
source                   1..27
                         mol_type = other DNA
                         organism = synthetic construct
SEQUENCE: 56
tcattcaacg tattcttcaa gtcgttg                                 27

SEQ ID NO: 57            moltype = DNA   length = 18
FEATURE                  Location/Qualifiers
source                   1..18
                         mol_type = other DNA
                         organism = synthetic construct
SEQUENCE: 57
tggtgcgggt cggtttta                                           18

SEQ ID NO: 58            moltype = DNA   length = 21
FEATURE                  Location/Qualifiers
source                   1..21
                         mol_type = other DNA
                         organism = synthetic construct
SEQUENCE: 58
ccgaatatcc tggaccagca t                                       21

SEQ ID NO: 59            moltype = DNA   length = 20
FEATURE                  Location/Qualifiers
source                   1..20
                         mol_type = other DNA
                         organism = synthetic construct
SEQUENCE: 59
cgctgatcaa cctgggactt                                         20

SEQ ID NO: 60            moltype = DNA   length = 21
FEATURE                  Location/Qualifiers
source                   1..21
                         mol_type = other DNA
                         organism = synthetic construct
SEQUENCE: 60
gtcaaagcca agctcgatga g                                       21

SEQ ID NO: 61            moltype = DNA   length = 100
FEATURE                  Location/Qualifiers
source                   1..100
                         mol_type = other DNA
                         organism = Galdieria sulphuraria
SEQUENCE: 61
```

```
gtttgtaaac tcggattcgg atgcaagtac tttggaattg accatgaaag atcctctcac    60
aaaagtggaa gttgtggtaa gaatagccag ttctccttgt                          100

SEQ ID NO: 62              moltype = DNA   length = 100
FEATURE                    Location/Qualifiers
source                     1..100
                           mol_type = other DNA
                           organism = Galdieria sulphuraria
SEQUENCE: 62
gtttgaaaac tcggattcgg atgcaagtac tttggaattg accatgaaag atcctctcac    60
aaaagtggaa gttgtggtaa gaaaagacag ttctcattgt                          100

SEQ ID NO: 63              moltype = DNA   length = 38
FEATURE                    Location/Qualifiers
source                     1..38
                           mol_type = other DNA
                           organism = synthetic construct
SEQUENCE: 63
cggtacccgg ggatcgtctc ctctcgaaaa atgattac                            38

SEQ ID NO: 64              moltype = DNA   length = 37
FEATURE                    Location/Qualifiers
source                     1..37
                           mol_type = other DNA
                           organism = synthetic construct
SEQUENCE: 64
cgactctaga ggatctgtga agactatgtc ggtgttc                             37

SEQ ID NO: 65              moltype = DNA   length = 36
FEATURE                    Location/Qualifiers
source                     1..36
                           mol_type = other DNA
                           organism = synthetic construct
SEQUENCE: 65
cggtacccgg ggatccattc ccctatttca tgaatg                              36

SEQ ID NO: 66              moltype = DNA   length = 22
FEATURE                    Location/Qualifiers
source                     1..22
                           mol_type = other DNA
                           organism = synthetic construct
SEQUENCE: 66
gactctttcg gcgttatttg cg                                             22

SEQ ID NO: 67              moltype = DNA   length = 40
FEATURE                    Location/Qualifiers
source                     1..40
                           mol_type = other DNA
                           organism = synthetic construct
SEQUENCE: 67
aacgccgaaa gagtcgatat catggttagc aagggcgaag                          40

SEQ ID NO: 68              moltype = DNA   length = 48
FEATURE                    Location/Qualifiers
source                     1..48
                           mol_type = other DNA
                           organism = synthetic construct
SEQUENCE: 68
ccatgaaatg caagtgcggc cgctcactta tacagttcat ccataccc                 48

SEQ ID NO: 69              moltype = DNA   length = 21
FEATURE                    Location/Qualifiers
source                     1..21
                           mol_type = other DNA
                           organism = synthetic construct
SEQUENCE: 69
acttgcattt catggcgagg c                                              21

SEQ ID NO: 70              moltype = DNA   length = 37
FEATURE                    Location/Qualifiers
source                     1..37
                           mol_type = other DNA
                           organism = synthetic construct
SEQUENCE: 70
cgactctaga ggatctcaag ctcggaagag aagcttc                             37

SEQ ID NO: 71              moltype = DNA   length = 39
FEATURE                    Location/Qualifiers
source                     1..39
```

```
                              mol_type = other DNA
                              organism = synthetic construct
SEQUENCE: 71
cggtacccgg ggatctcaca gcatatgtca agagcctgc                              39

SEQ ID NO: 72          moltype = DNA   length = 27
FEATURE                Location/Qualifiers
source                 1..27
                       mol_type = other DNA
                       organism = synthetic construct
SEQUENCE: 72
gtttgcagtg tttccgatca gagttag                                          27

SEQ ID NO: 73          moltype = DNA   length = 35
FEATURE                Location/Qualifiers
source                 1..35
                       mol_type = other DNA
                       organism = synthetic construct
SEQUENCE: 73
ggaaacactg caaacatgcg gttaggcgta gggtc                                 35

SEQ ID NO: 74          moltype = DNA   length = 31
FEATURE                Location/Qualifiers
source                 1..31
                       mol_type = other DNA
                       organism = synthetic construct
SEQUENCE: 74
cttgttaaag ttcatagccg aacggcgggc g                                     31

SEQ ID NO: 75          moltype = DNA   length = 25
FEATURE                Location/Qualifiers
source                 1..25
                       mol_type = other DNA
                       organism = synthetic construct
SEQUENCE: 75
atgaacttta acaagattga cctgg                                            25

SEQ ID NO: 76          moltype = DNA   length = 35
FEATURE                Location/Qualifiers
source                 1..35
                       mol_type = other DNA
                       organism = synthetic construct
SEQUENCE: 76
agcgcacata caaactcaca ggagccagtc gttgg                                 35

SEQ ID NO: 77          moltype = DNA   length = 24
FEATURE                Location/Qualifiers
source                 1..24
                       mol_type = other DNA
                       organism = synthetic construct
SEQUENCE: 77
gtttgtatgt gcgcttcgta aagc                                             24

SEQ ID NO: 78          moltype = DNA   length = 39
FEATURE                Location/Qualifiers
source                 1..39
                       mol_type = other DNA
                       organism = synthetic construct
SEQUENCE: 78
cgactctaga ggatctctga cctaagacca cacacctag                             39

SEQ ID NO: 79          moltype = DNA   length = 32
FEATURE                Location/Qualifiers
source                 1..32
                       mol_type = other DNA
                       organism = synthetic construct
SEQUENCE: 79
tgattcagaa agaaacattc ccctatttca tg                                    32

SEQ ID NO: 80          moltype = DNA   length = 37
FEATURE                Location/Qualifiers
source                 1..37
                       mol_type = other DNA
                       organism = synthetic construct
SEQUENCE: 80
tgacatatgc tgtgatcaag ctcggaagag aagcttc                               37

SEQ ID NO: 81          moltype = DNA   length = 24
FEATURE                Location/Qualifiers
```

-continued

```
source               1..24
                     mol_type = other DNA
                     organism = synthetic construct
SEQUENCE: 81
tcacagcata tgtcaagagc ctgc                                            24

SEQ ID NO: 82        moltype = DNA   length = 39
FEATURE              Location/Qualifiers
source               1..39
                     mol_type = other DNA
                     organism = synthetic construct
SEQUENCE: 82
actgtatttc gaatgtctga cctaagacca cacacctag                           39

SEQ ID NO: 83        moltype = DNA   length = 23
FEATURE              Location/Qualifiers
source               1..23
                     mol_type = other DNA
                     organism = synthetic construct
SEQUENCE: 83
cattcgaaat acagtgtttc gtg                                             23

SEQ ID NO: 84        moltype = DNA   length = 24
FEATURE              Location/Qualifiers
source               1..24
                     mol_type = other DNA
                     organism = synthetic construct
SEQUENCE: 84
tttctttctg aatcaaacga gacg                                           24

SEQ ID NO: 85        moltype = DNA   length = 17
FEATURE              Location/Qualifiers
source               1..17
                     mol_type = other DNA
                     organism = synthetic construct
SEQUENCE: 85
gtaaaacgac ggccagt                                                   17

SEQ ID NO: 86        moltype = DNA   length = 17
FEATURE              Location/Qualifiers
source               1..17
                     mol_type = other DNA
                     organism = synthetic construct
SEQUENCE: 86
caggaaacag ctatgac                                                   17

SEQ ID NO: 87        moltype = DNA   length = 22
FEATURE              Location/Qualifiers
source               1..22
                     mol_type = other DNA
                     organism = synthetic construct
SEQUENCE: 87
cattgcacag caatgaaaag cg                                             22

SEQ ID NO: 88        moltype = DNA   length = 25
FEATURE              Location/Qualifiers
source               1..25
                     mol_type = other DNA
                     organism = synthetic construct
SEQUENCE: 88
atcgaaactg cgtagatagt gtcgg                                          25
```